US009504591B2

(12) United States Patent
Burnett et al.

(10) Patent No.: US 9,504,591 B2
(45) Date of Patent: Nov. 29, 2016

(54) DEVICE FOR INTERMITTENTLY OBSTRUCTING A GASTRIC OPENING AND METHOD OF USE

(71) Applicant: BAROnova, Inc., Goleta, CA (US)

(72) Inventors: Daniel R. Burnett, San Francisco, CA (US); Hugh Narciso, Santa Barbara, CA (US); Paul Paspa, Los Gatos, CA (US); David Wiser, Ventura, CA (US); Stephen Meade, Camarillo, CA (US)

(73) Assignee: BAROnova, Inc., San Carlos, CA (US)

( * ) Notice: Subject to any disclaimer, the term of this patent is extended or adjusted under 35 U.S.C. 154(b) by 165 days.

(21) Appl. No.: 14/495,371

(22) Filed: Sep. 24, 2014

(65) Prior Publication Data

US 2015/0011969 A1    Jan. 8, 2015

Related U.S. Application Data

(62) Division of application No. 12/205,403, filed on Sep. 5, 2008, now Pat. No. 8,888,797.

(60) Provisional application No. 60/970,619, filed on Sep. 7, 2007.

(51) Int. Cl.
*A61F 5/00* (2006.01)
*A61B 5/06* (2006.01)
(Continued)

(52) U.S. Cl.
CPC ............ *A61F 5/0079* (2013.01); *A61B 5/065* (2013.01); *A61B 17/1219* (2013.01);
(Continued)

(58) Field of Classification Search
CPC .................... A61B 17/12022; A61B 17/1204; A61B 17/12099; A61B 17/12136; A61B 17/12159; A61B 17/12163; A61B 17/12172; A61B 17/1219; A61B 2017/00119; A61B 2017/00221; A61B 2017/22069; A61B 5/065; A61F 5/0079; A61M 31/002
See application file for complete search history.

(56) References Cited

U.S. PATENT DOCUMENTS

| 2,499,045 A | 2/1950 | Ray et al. |
| 3,154,077 A | 10/1964 | Cannon |

(Continued)

FOREIGN PATENT DOCUMENTS

| AU | 2004258968 | 2/2012 |
| DE | 4012642 | 10/1991 |

(Continued)

OTHER PUBLICATIONS

U.S. Appl. No. 10/671,191, filed Sep. 24, 2003.
(Continued)

*Primary Examiner* — Bhisma Mehta
*Assistant Examiner* — Brandy S Lee
(74) *Attorney, Agent, or Firm* — Levine Bagade Han LLP

(57) ABSTRACT

The present invention relates to a device for intermittently obstructing a bodily opening, such as a gastric opening, and includes a proximal member connected to a distal member by a tether. The proximal member includes an apron member surrounding a first occluding member, which is formable from an elongated and narrower configuration to a contracted or expanded but wider configuration. When employed in the stomach, the device of the present invention is arranged transluminally, with the distal member disposed in the duodenum and the proximal member disposed against the pyloric valve, intermittently occluding the pyloric valve and preventing or delaying the flow of gastric contents through the pyloric valve. In certain embodiments, a reservoir may be included for releasing a substance of interest, for example for releasing insulin from a reservoir disposed in the distal member. Sensors, actuators, and data transmission devices may also be included.

25 Claims, 41 Drawing Sheets

(51) Int. Cl.
*A61M 31/00* (2006.01)
*A61B 17/12* (2006.01)
*A61B 17/00* (2006.01)
*A61B 17/22* (2006.01)

(52) U.S. Cl.
CPC .. *A61B 17/12099* (2013.01); *A61B 17/12136* (2013.01); *A61B 17/12159* (2013.01); *A61B 17/12163* (2013.01); *A61B 17/12172* (2013.01); *A61M 31/002* (2013.01); *A61B 17/1204* (2013.01); *A61B 17/12022* (2013.01); *A61B 2017/00119* (2013.01); *A61B 2017/00221* (2013.01); *A61B 2017/22069* (2013.01)

(56) References Cited

U.S. PATENT DOCUMENTS

| | | |
|---|---|---|
| 3,915,171 A | 10/1975 | Shermeta |
| 4,133,315 A | 1/1979 | Berman et al. |
| 4,240,412 A | 12/1980 | James |
| 4,246,893 A | 1/1981 | Berson |
| 4,315,509 A | 2/1982 | Smit |
| 4,368,739 A | 1/1983 | Nelson |
| 4,416,267 A | 11/1983 | Garren et al. |
| 4,485,805 A | 12/1984 | Foster, Jr. |
| 4,517,979 A | 5/1985 | Pecenka |
| 4,598,699 A | 7/1986 | Garren et al. |
| 4,648,383 A | 3/1987 | Angelchik |
| 4,657,020 A | 4/1987 | Lifton |
| 4,694,827 A | 9/1987 | Weiner et al. |
| 4,735,214 A | 4/1988 | Berman |
| 4,762,128 A | 8/1988 | Rosenbluth |
| 4,836,204 A | 6/1989 | Landymore et al. |
| 4,878,905 A | 11/1989 | Blass |
| 4,925,446 A | 5/1990 | Garay et al. |
| 4,930,496 A | 6/1990 | Bosley |
| 4,946,440 A | 8/1990 | Hall |
| 5,011,488 A | 4/1991 | Ginsburg |
| 5,067,957 A | 11/1991 | Jervis |
| 5,108,420 A | 4/1992 | Marks |
| 5,129,915 A | 7/1992 | Cantenys |
| 5,192,301 A | 3/1993 | Kamiya et al. |
| 5,246,445 A | 9/1993 | Yachia et al. |
| 5,282,829 A | 2/1994 | Hermes |
| 5,306,300 A | 4/1994 | Berry |
| 5,312,343 A | 5/1994 | Krog et al. |
| 5,423,872 A | 6/1995 | Cigaina |
| 5,509,888 A | 4/1996 | Miller |
| 5,514,091 A | 5/1996 | Yoon |
| 5,514,178 A | 5/1996 | Torchio |
| 5,540,701 A | 7/1996 | Sharkey et al. |
| 5,545,210 A | 8/1996 | Hess et al. |
| 5,634,936 A | 6/1997 | Linden et al. |
| 5,674,192 A | 10/1997 | Sahatjian et al. |
| 5,676,688 A | 10/1997 | Jaker et al. |
| 5,707,355 A | 1/1998 | Zimmon |
| 5,750,585 A | 5/1998 | Park et al. |
| 5,752,971 A | 5/1998 | Rosenbluth et al. |
| 5,782,800 A | 7/1998 | Yoon |
| 5,820,584 A | 10/1998 | Crabb |
| 5,853,422 A | 12/1998 | Huebsch et al. |
| 5,947,991 A | 9/1999 | Cowan |
| 5,976,174 A * | 11/1999 | Ruiz ................ A61B 17/0057 606/151 |
| 6,067,991 A | 5/2000 | Forsell |
| 6,102,928 A | 8/2000 | Bonutti |
| 6,112,703 A | 9/2000 | Handelsman |
| 6,117,159 A | 9/2000 | Huebsch et al. |
| 6,152,144 A | 11/2000 | Lesh et al. |
| 6,159,219 A | 12/2000 | Ren |
| 6,162,201 A | 12/2000 | Cohen |
| 6,183,520 B1 | 2/2001 | Pintauro et al. |
| 6,245,090 B1 | 6/2001 | Gilson et al. |
| 6,270,515 B1 | 8/2001 | Linden et al. |
| 6,371,974 B1 | 4/2002 | Brenneman et al. |
| 6,409,656 B1 | 6/2002 | Sangouard et al. |
| 6,454,785 B2 | 9/2002 | De Hoyos Garza |
| 6,488,962 B1 | 12/2002 | Berner et al. |
| 6,503,264 B1 | 1/2003 | Birk |
| 6,527,701 B1 | 3/2003 | Sayet et al. |
| 6,527,739 B1 | 3/2003 | Bigus et al. |
| 6,540,789 B1 | 4/2003 | Silverman et al. |
| 6,544,291 B2 | 4/2003 | Taylor |
| 6,558,400 B2 | 5/2003 | Deem et al. |
| 6,579,301 B1 | 6/2003 | Bales et al. |
| 6,600,953 B2 | 7/2003 | Flesler et al. |
| 6,652,578 B2 | 11/2003 | Bailey et al. |
| 6,675,809 B2 | 1/2004 | Stack et al. |
| 6,689,046 B2 | 2/2004 | Sayet et al. |
| 6,702,846 B2 | 3/2004 | Mikus |
| 6,740,121 B2 | 5/2004 | Geitz |
| 6,755,869 B2 | 6/2004 | Geitz |
| 6,802,868 B2 | 10/2004 | Silverman et al. |
| 6,860,895 B1 | 3/2005 | Akerfeldt et al. |
| 6,994,095 B2 | 2/2006 | Burnett |
| 7,011,621 B2 | 3/2006 | Sayet et al. |
| 7,037,344 B2 | 5/2006 | Kagan et al. |
| 7,054,690 B2 | 5/2006 | Imran et al. |
| 7,087,072 B2 | 8/2006 | Marino et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,160,312 B2 | 1/2007 | Saadat |
| 7,167,750 B2 | 1/2007 | Knudson et al. |
| 7,186,251 B2 | 3/2007 | Malecki et al. |
| 7,320,696 B2 | 1/2008 | Gazi et al. |
| 7,588,584 B2 | 9/2009 | Fogarty et al. |
| 7,803,195 B2 | 9/2010 | Levy et al. |
| 7,842,053 B2 | 11/2010 | Chanduszko et al. |
| 8,048,169 B2 | 11/2011 | Burnett et al. |
| 8,257,389 B2 | 9/2012 | Chanduszko et al. |
| 2002/0013601 A1 | 1/2002 | Nobles et al. |
| 2002/0038100 A1 | 3/2002 | Okada |
| 2002/0091395 A1 | 7/2002 | Gabbay |
| 2002/0165589 A1 | 11/2002 | Imran et al. |
| 2002/0188354 A1 | 12/2002 | Peghini |
| 2002/0198470 A1 | 12/2002 | Imran et al. |
| 2002/0198479 A1 | 12/2002 | Talish |
| 2003/0023150 A1 | 1/2003 | Yokoi et al. |
| 2003/0040804 A1 | 2/2003 | Stack et al. |
| 2003/0078611 A1 | 4/2003 | Hashiba et al. |
| 2003/0093117 A1 | 5/2003 | Saadat |
| 2003/0109931 A1 | 6/2003 | Geitz |
| 2003/0109935 A1 | 6/2003 | Geitz |
| 2003/0120328 A1 | 6/2003 | Jenkins et al. |
| 2003/0144708 A1 | 7/2003 | Starkebaum |
| 2003/0152601 A1 | 8/2003 | Kanayama |
| 2003/0153806 A1 | 8/2003 | Miller |
| 2003/0158601 A1 | 8/2003 | Silverman et al. |
| 2004/0034408 A1 | 2/2004 | Majercack |
| 2004/0059368 A1 | 3/2004 | Maryanka |
| 2004/0107004 A1 | 6/2004 | Levine et al. |
| 2004/0117031 A1 | 6/2004 | Stack et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0213825 A1 | 10/2004 | Levy |
| 2004/0230222 A1 | 11/2004 | van der Burg et al. |
| 2004/0236357 A1 | 11/2004 | Kraemer et al. |
| 2004/0267378 A1 | 12/2004 | Gazi et al. |
| 2005/0033331 A1 | 2/2005 | Burnett et al. |
| 2005/0033332 A1 | 2/2005 | Burnett |
| 2005/0038460 A1 | 2/2005 | Jayaraman |
| 2005/0038470 A1 | 2/2005 | Van Der Burg et al. |
| 2005/0055039 A1 | 3/2005 | Burnett et al. |
| 2005/0064009 A1 | 3/2005 | Bates |
| 2005/0090873 A1 | 4/2005 | Imran et al. |
| 2005/0096673 A1 | 5/2005 | Stack et al. |
| 2005/0149142 A1 | 7/2005 | Starkebaum |
| 2005/0192627 A1 | 9/2005 | Whisenant et al. |
| 2005/0192629 A1 | 9/2005 | Saadat et al. |
| 2005/0251154 A1 * | 11/2005 | Chanduszko ...... A61B 17/0057 |

(56) References Cited

U.S. PATENT DOCUMENTS

| | | |
|---|---|---|
| 2005/0273060 A1 | 12/2005 | Levy et al. |
| 2005/0288786 A1 | 12/2005 | Chanduszko |
| 2006/0020278 A1 | 1/2006 | Burnett et al. |
| 2006/0178691 A1 | 8/2006 | Binmoeller |
| 2006/0217763 A1 | 9/2006 | Abbott et al. |
| 2006/0259074 A1 | 11/2006 | Kelleher et al. |
| 2006/0282107 A1 | 12/2006 | Hashiba et al. |
| 2006/0293742 A1 | 12/2006 | Dann et al. |
| 2007/0016262 A1 | 1/2007 | Gross et al. |
| 2007/0027548 A1 | 2/2007 | Levine et al. |
| 2007/0056591 A1 | 3/2007 | McSwain |
| 2007/0083224 A1 | 4/2007 | Hively |
| 2007/0135831 A1 | 6/2007 | Burnett et al. |
| 2007/0178160 A1 | 8/2007 | Burnett |
| 2007/0198082 A1 | 8/2007 | Kapadia et al. |
| 2007/0239284 A1 | 10/2007 | Skerven et al. |
| 2007/0250132 A1 | 10/2007 | Burnett |
| 2009/0118757 A1 | 5/2009 | Burnett et al. |
| 2009/0118758 A1 | 5/2009 | Burnett et al. |
| 2009/0177288 A1 | 7/2009 | Wallsten |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |
| 2009/0299486 A1 | 12/2009 | Shohat et al. |

FOREIGN PATENT DOCUMENTS

| | | |
|---|---|---|
| JP | 2007-500538 | 1/2007 |
| WO | WO 88/00027 | 1/1988 |
| WO | WO 90/00369 | 1/1990 |
| WO | WO 00/48672 | 8/2000 |
| WO | WO 02/091961 | 11/2002 |
| WO | WO 03/017882 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

606/151

OTHER PUBLICATIONS

U.S. Appl. No. 10/833,950, filed Apr. 27, 2004.
U.S. Appl. No. 10/915,716, filed Aug. 9, 2004.
U.S. Appl. No. 11/215,430, filed Aug. 29, 2005.
U.S. Appl. No. 11/602,620, filed Nov. 20, 2006.
U.S. Appl. No. 11/702,840, filed Feb. 5, 2007.
U.S. Appl. No. 11/702,888, filed Feb. 5, 2007.
U.S. Appl. No. 12/351,705, filed Jan. 9, 2009.
U.S. Appl. No. 12/351,686, filed Jan. 9, 2009.
U.S. Appl. No. 12/351,665, filed Jan. 9, 2009.
U.S. Appl. No. 12/351,644, filed Jan. 9, 2009.
U.S. Appl. No. 12/434,594, filed May 1, 2009.
U.S. Appl. No. 14/618,868, filed Feb. 10, 2015.
U.S. Appl. No. 12/205,403, filed Sep. 5, 2008.
U.S. Appl. No. 12/352,497, filed Jan. 12, 2009.
U.S. Appl. No. 12/352,508, filed Jan. 12, 2009.
U.S. Appl. No. 14/849,450, filed Sep. 9, 2015.
Lopasso, Fabio P. et al., "A Pilot Study to Evaluate the Safety, Tolerance, and Efficacy of a Novel Stationary Antral Balloon (SAB) for Obesity," Journal of Clinical Gastroenterology, vol. 42, No. 1, Jan. 2008, 48-53.

* cited by examiner

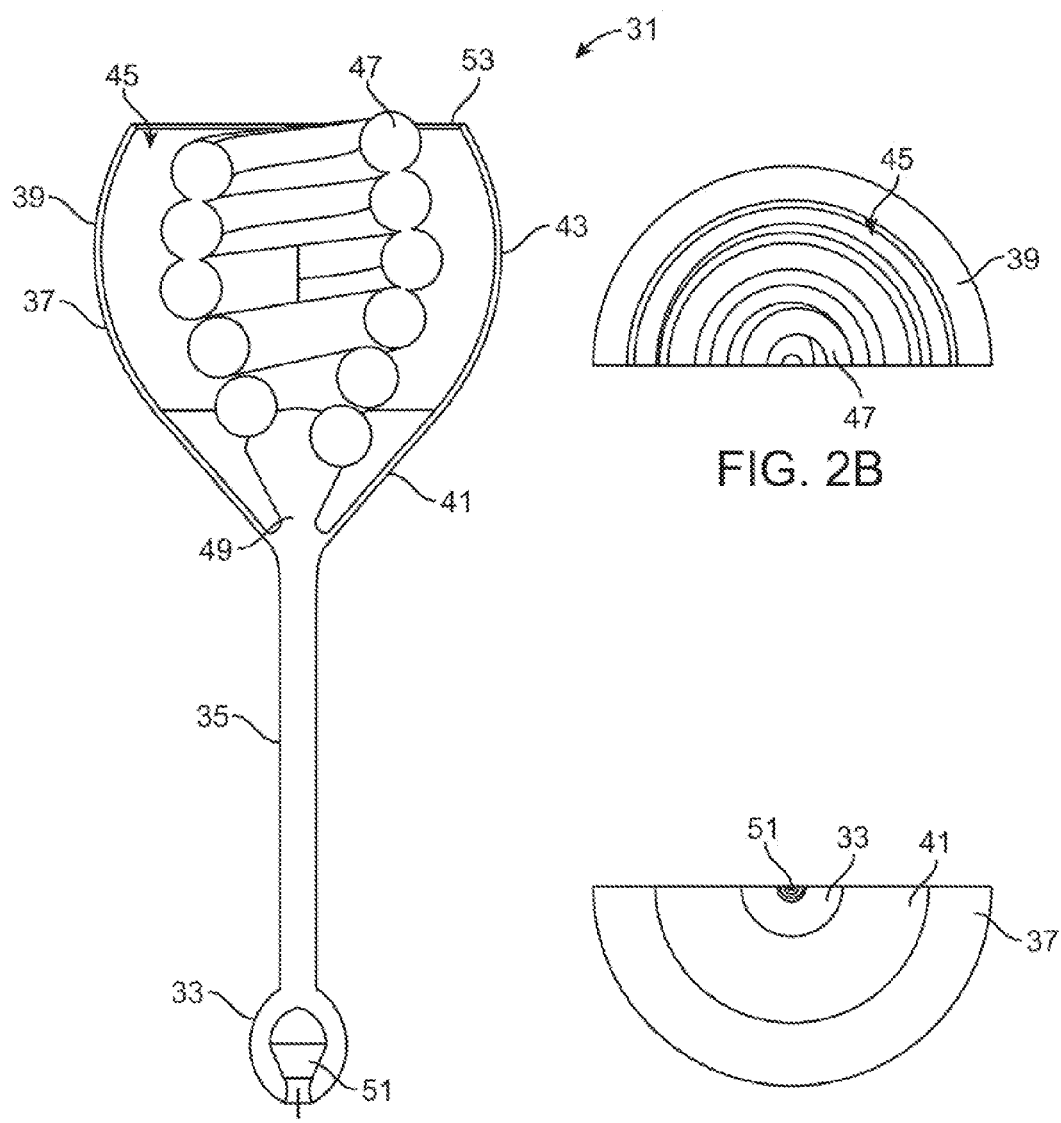

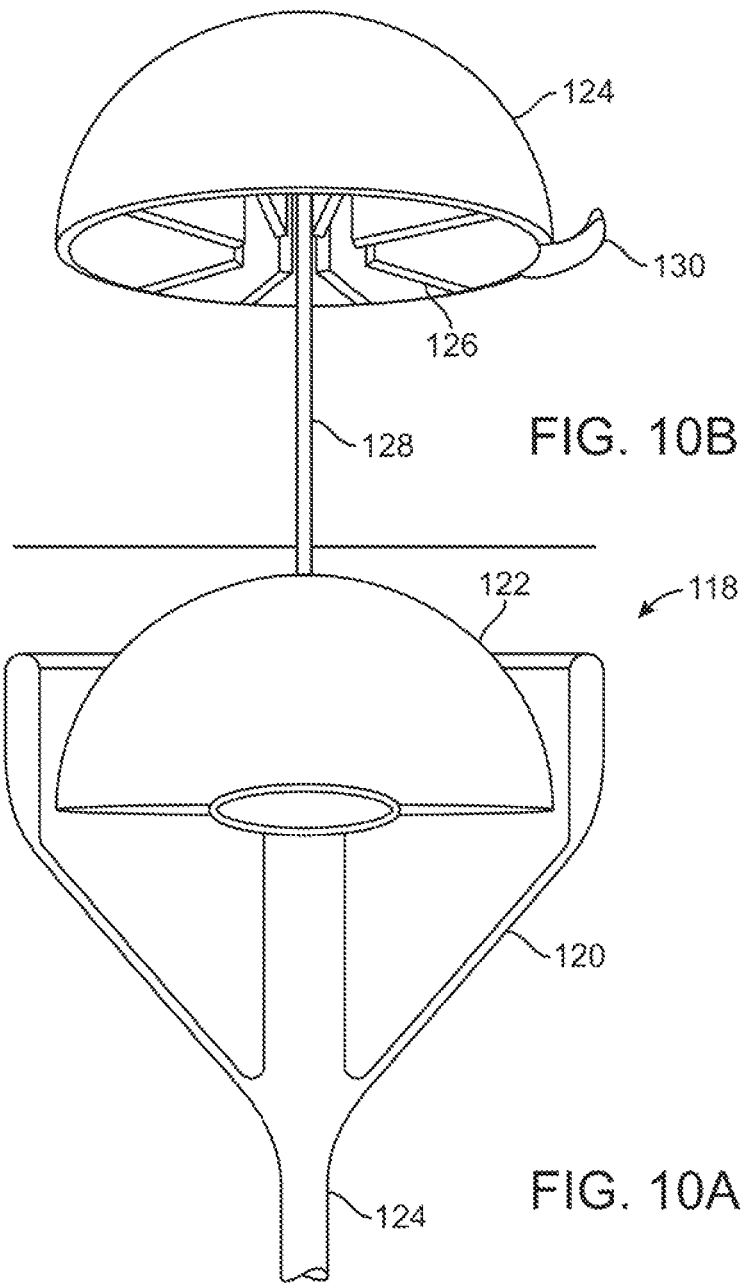

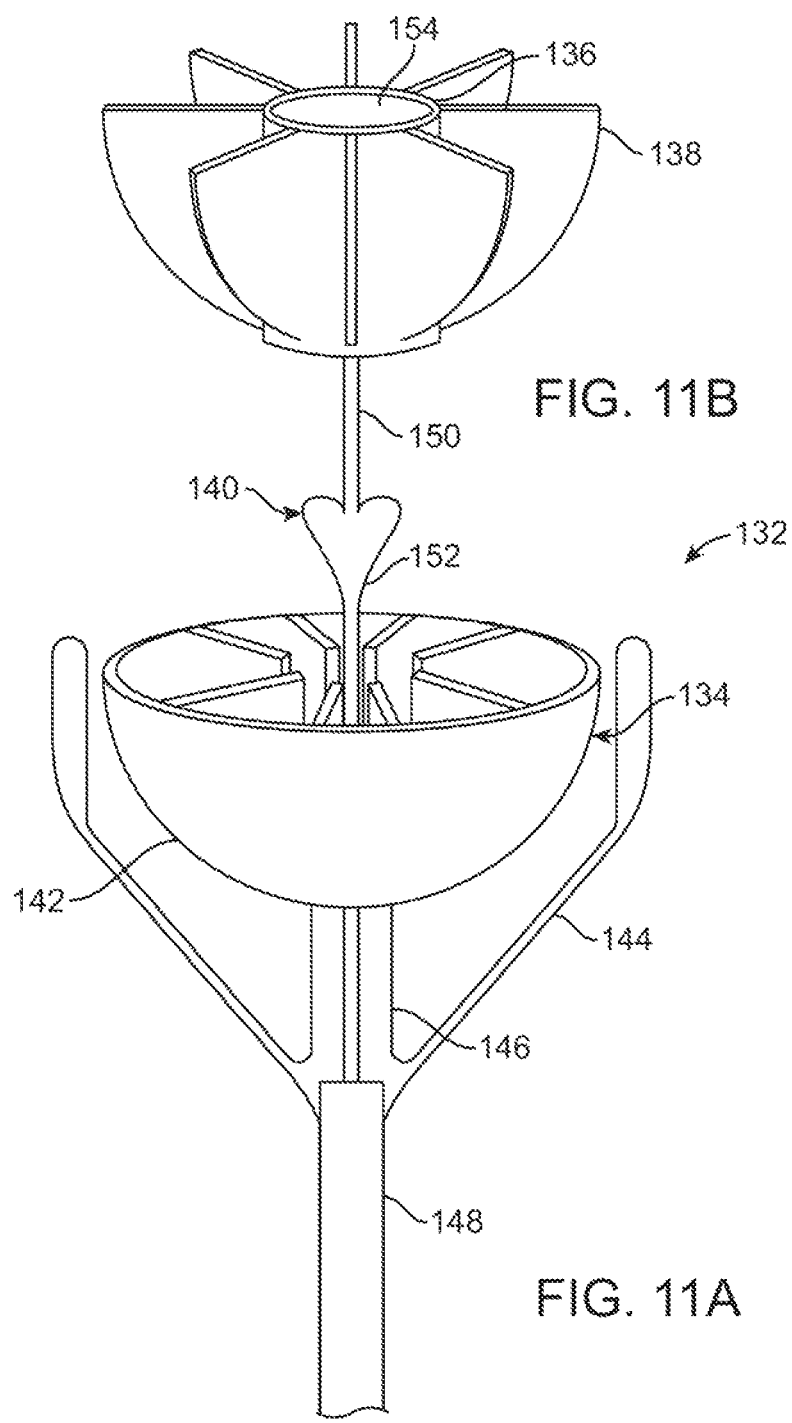

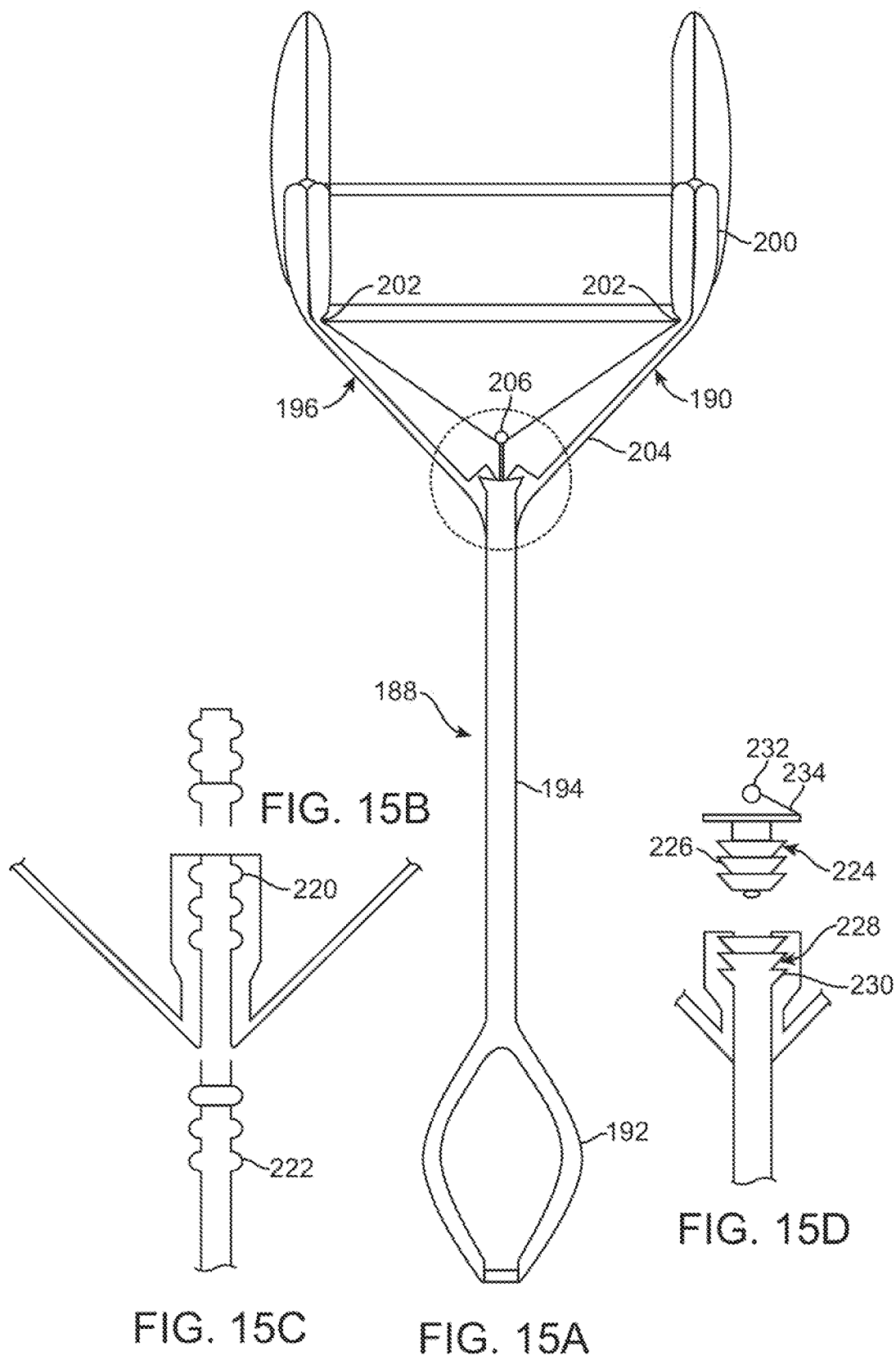

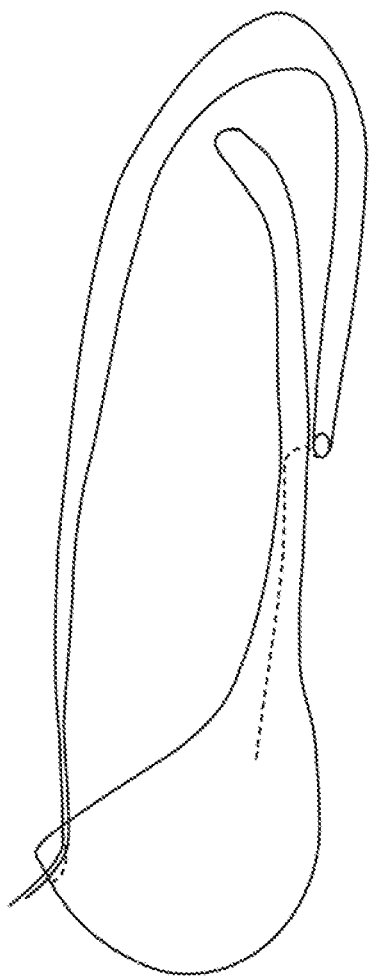
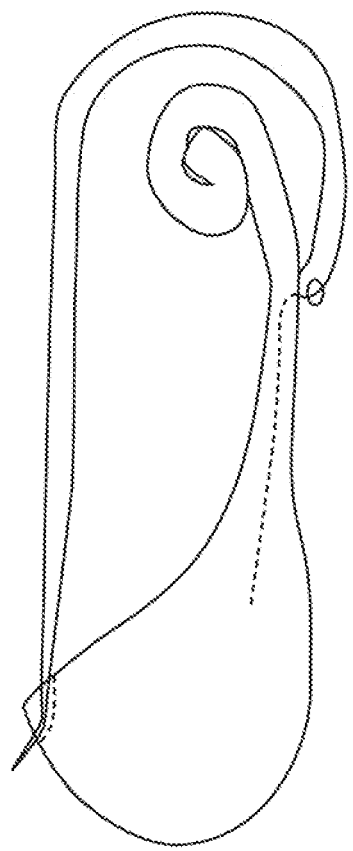
FIG. 20A    FIG. 20B
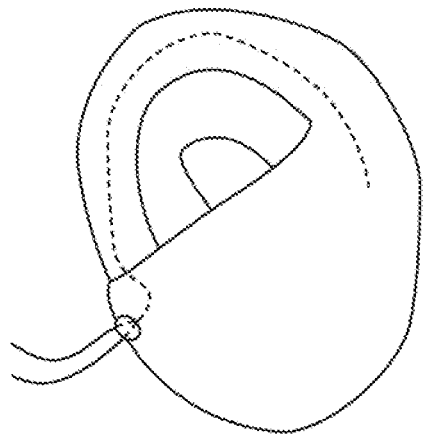
FIG. 20C

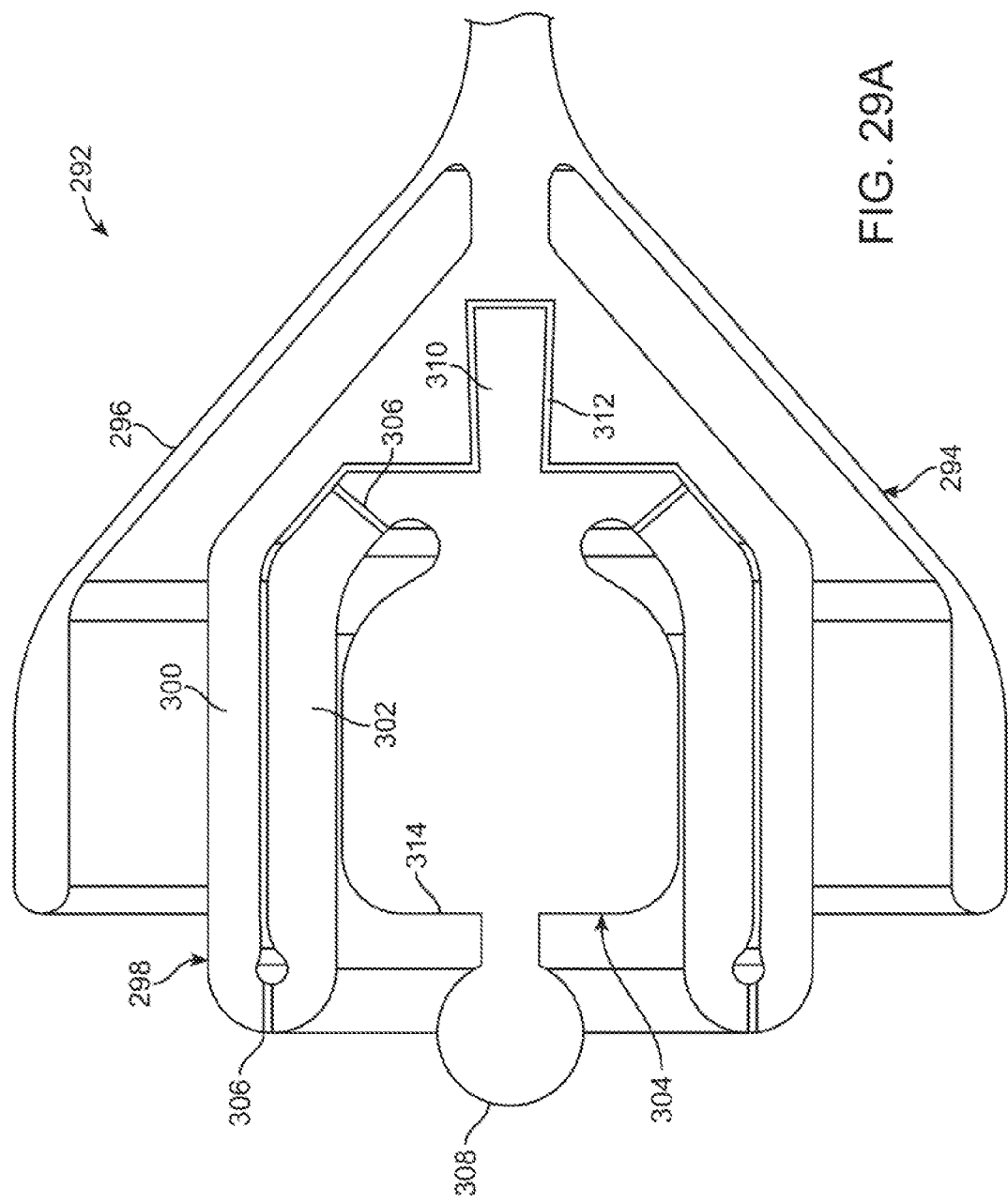

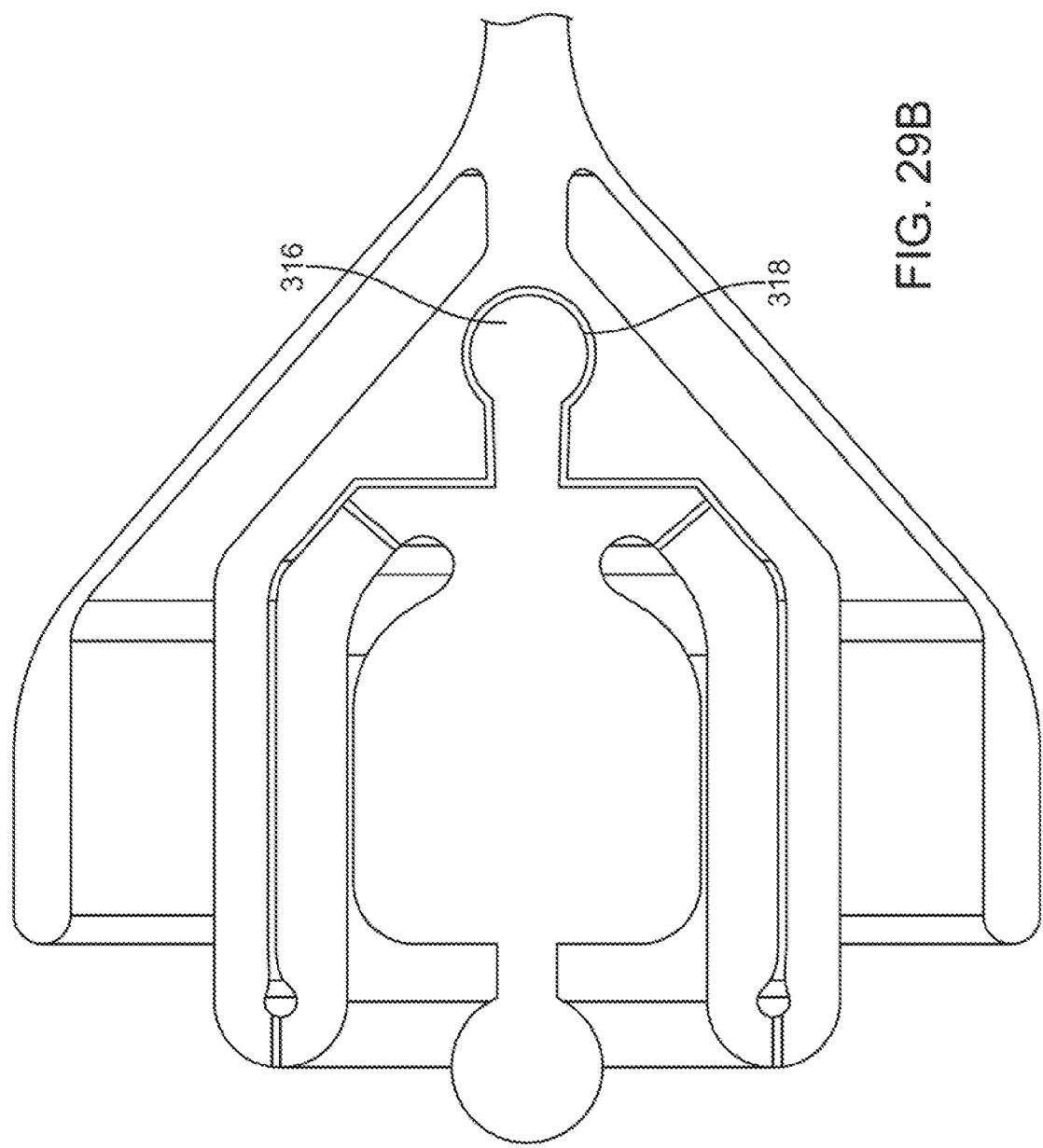

DEVICE FOR INTERMITTENTLY OBSTRUCTING A GASTRIC OPENING AND METHOD OF USE

CROSS-REFERENCE TO RELATED APPLICATIONS

This application is a divisional of U.S. patent application Ser. No. 12/205,403 filed Sep. 5, 2008, which claims the benefit of priority to U.S. Prov. Pat. App. 60/970,619 filed Sep. 7, 2007, each of which is incorporated herein by reference in its entirety.

FIELD OF THE INVENTION

The present invention relates to a gastro-intestinal device for treating obesity and other medical conditions. More particularly, the present invention relates to a device that is positioned transluminally in a patient's gastro-intestinal tract to intermittently obstruct or reduce the flow of gastric contents.

BACKGROUND OF THE INVENTION

Obesity is a condition of epidemic proportions in the United States. Recent government studies have indicated that up to 40% of Americans are obese and that, among those, almost 20% are morbidly obese. Obesity is not the problem in and of itself, but is the source of multiple pathological conditions, including cardiovascular disease, heart disease, stroke, diabetes, and obstructive sleep apnea. Recent studies have indicated that obesity can reduce a person's lifespan by an average of three years in adults and twenty years in children.

Many attempts have been made in the prior art to provide medications, devices, and surgical procedures for the treatment of obesity, all of which either have serious side effects or are basically ineffective. For example, various diets, supplements and pharmaceuticals have been developed and marketed, but none have shown any significant benefits to date in the treatment of obesity with the exception of some pharmaceuticals, which have unfortunately been found to cause a number of serious, life-threatening medical conditions. To date, there are no commercially available supplements or drugs that have been proven to be effective in promoting significant weight loss and at the same time that are free from serious collateral side effects.

Recognizing that no cure has been developed to date that is both effective and safe, the medical industry has introduced more extreme procedures, an example of which is the Roux-En-Y gastric bypass. This extensive and invasive surgery is highly effective but is also potentially lethal, with a 1-2% mortality rate, a six month recovery period, and a cost of tens of thousands of dollars, yet it is becoming increasingly popular because other available treatments do not produce the desired results. Gastric reduction, or simply removing a large segment of the stomach, is another procedure that is similar to gastric bypass and that, like gastric bypass, has also been associated with potentially lethal complications. Data from recent studies have indicated that even in the lowest risk groups, obesity surgery causes an average one-year mortality rate of nearly 5%.

In another attempt to treat obesity, devices have also been developed in the prior art that are aimed at providing a sense of fullness to a patient, so to cause the patient to reduce food intake. Such devices may be configured as stents that support the stomach or the pyloric valve to or that may be configured as permanent occluders. Unfortunately, these devices are implanted in the patient on an essentially permanent basis and typically include complex mechanical or electrical features that may stop working properly over time or that may require maintenance from time to time. Examples of such devices in the prior art can be found in U.S. Pat. Nos. 5,509,888; 6,067,991; 6,527,701; 6,689,046; 7,011,621; 7,737,344; 7,120,498; 7,122,058 and 7,167,750, and in U.S. Patent Application Publications Nos. 2004/0172142; 2005/0273060; 2007/0016262; 2007/0027548; and 2007/0083224.

Evidence has been developed showing that benefits can be derived from reducing gastroduodenal flow. In unpublished, but recently presented data at the American Society for Bariatric Surgery conference of June 2003, stimulation of the gastric vagus nerve with subsequent reduction in gastric motility resulted in a loss of over 20% of excess weight over a nine month period. Furthermore, there is data suggesting that gastric vagotomy is also effective in the treatment of obesity trough a similar mechanism. Unfortunately, these therapies require highly invasive, sometimes irreversible, surgical procedures, making them undesirable for a large segment of the obese population.

BRIEF SUMMARY OF THE INVENTION

It is an object of the present invention to provide a device for the treatment of obesity and related conditions that intermittently obstructs a transluminal passage, such as a gastric opening.

It is also an object of the present invention to provide a device for the treatment of obesity and related conditions that is well tolerated by the stomach and in general, by the gastro-intestinal tact.

It is a further object of the present invention to provide a device for the treatment of obesity and related conditions that can be implanted and removed with medical procedures that are safe and relatively simple to perform.

Briefly, the device of the present invention operates as a transluminal device that obstructs the pylorus or other organ on an intermittent basis and that causes a reduced flow of gastric contents into the intestinal tract. The device of the present invention may just occupy space in the stomach and occlude the pyloric valve from time to time, or also may partially obstruct the duodenum or the small intestine, reducing overall gastrointestinal transit. The intermittent blockage of the gastrointestinal tract results in weight loss and also in an increased or sustained feeling of fullness by the patient.

The device of the present invention can be placed and removed with simple endoscopic procedures and is completely reversible. In particular, the device of the present invention can be inserted and removed orally, nasally or transcutaneously and, in certain embodiments, can be triggered externally or can be caused to expand or can self-expand once in the gastrointestinal space.

In one embodiment, a device according to the present invention includes a proximal member oriented in the direction of the stomach after implantation and a distal member oriented in the direction of the duodenum after implantation that are connected by a tether.

The proximal member is composed of a first occluding member surrounded by an apron member. The first occluding member is formable from an elongated, narrower configuration to a contracted, wider configuration, while the apron member has an essentially cylindrical portion that surrounds the first occluding member and an essentially conical portion that connects the apron member to the tether, providing the apron member with a funnel-like shape. In one embodiment, the cylindrical portion is spaced from the first occluding member by an interstice, and the cylindrical and conical portions may have different wall thickness.

The first occluding member may be formable from the narrower configuration to the wider configuration by injecting a substance within the first occluding member, or may have a solid structure that can be compressed to assume an expanded shape, in order to transition form the elongated configuration to the wider configuration.

In one embodiment, the elongated configuration exhibits a helical contour with a plurality of turns, and the wider configuration is formed from the helical configuration by nesting the turns one adjacent to the other to provide a bulbous body. The wider configuration is then locked in place by engaging a connecting member at the proximal end of the first occluding member with a mating cavity at the distal end of the first occluding member. This may be achieved by having a clinician pull on a string coupled to the connecting member in the direction of the mating cavity.

In one embodiment, such coupling string extends outside of the device along its entire length and then enters a lumen running from the first occluding member to the second occluding members through the tether. When entering the first occluding member, the string is looped through the connecting member and is removable from the device after the connecting member has engaged the matching cavity. The proximal end of the first occluding member may be reinforced to increase its resistance to tear during the compression of the first occluding member by including a reinforcing material in at least part of the structure of the proximal end.

The transformation process from the elongated configuration to the wider configuration is reversible, so that the device can be implanted in the stomach in the elongated configuration, reside in the stomach and/or gastro-intestinal tract in the wider configuration, and be removed from the stomach through the esophagus in the elongated configuration. In one embodiment, the wider configuration reverses to the elongated configuration by severing the connecting member from the proximal end, for example, by having a clinician cut a string coupling the connecting member to the proximal end or to a release member in the proximal end.

A device according to the present material is manufactured from a material that is biocompatible, that is able to withstand the gastrointestinal environment, and that prevents or anyways minimizes abrasion of the walls of the stomach and duodenum, particularly of the pyloric valve. In one embodiment, the device is manufactured from a resilient plastic material, for example, from a silicone material, and the apron member may be constructed to be flexible enough to reverse from a position surrounding a portion of the tether to a position surrounding the first occluding member, in order to facilitate insertion in the stomach according to one method of use.

The second occluding member also may have a bulbous shape, like a pod, and include an insert having a heavier weight than the remainder of the second occluding member, so to facilitate disposition and retention in the duodenum.

The device of the present invention is suited not only for the treatment of obesity, but also for treating other ailments, such as improper glucose tolerance in a diabetic or prediabetic subject and the progression of diabetes itself by inhibiting fasting insulin secretion or glucose-stimulated insulin secretion. The resent device is also suited for treating other ailments deriving from obesity, including hyperphagia, dyslipidemia, Prader Willi syndrome, Froelich's syndrome, Cohen syndrome, Summit syndrome, Alstrom syndrome, Borjesen syndrome, Bardet-Biedl syndrome, or hyperlipoproteinemia, types I, II, III, and IV.

The device of the present invention may also include sensors or transmitters to provide feedback and other data to an intra-corporeal or extra-corporeal processor, or may carry one or more compounds stored in a reservoir within the device or coated on the device. In one embodiment, insulin is released into the gastro-intestinal tract by disposing an insulin reservoir in the distal member of the device. Such a release of insulin may be controlled by the size of the orifice between the reservoir and the outer environment, or by a time-controlled actuator, or by an actuator controlled by one or more sensors, for example in response to detection of sugar in the gastro-intestinal tract.

Other embodiments of the present invention, methods of use of a device manufactured according to the present invention, and methods of treatment of a variety of ailments using the device of the present invention are discussed in detail in the following sections.

BRIEF DESCRIPTION OF THE SEVERAL
VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIGS. 2A-2C illustrate respectively a cross-sectional side view and top and bottom end views of another embodiment.

FIG. 6A is a partial cross-sectional side view of a third embodiment of the invention, while

FIG. 10A is a partial cross-sectional side view of a detail of a fifth embodiment of the invention, while FIG. 10B is a perspective view of the first occluding member of the embodiment of FIG. 10A.

FIG. 11A is a cross-sectional side view of a detail of a sixth embodiment of the invention, while FIG. 11B is a perspective view of the first occluding member of the embodiment of FIG. 11A.

FIG. 14A-14B are cross-sectional side views of a ninth embodiment of the invention, in the deployed state (FIG. 14A) and undeployed state (FIG. 14B), while FIG. 14C illustrates a detailed view of the connecting and retaining members in the embodiment of FIGS. 14A-14B.

FIG. 15A is a further cross-sectional view of the embodiment of FIG. 14A, while FIGS. 15B-15D illustrate detailed views if the coupling of the connecting member with the mating cavity.

FIG. 16A is a cross-sectional side view of a tenth embodiment of the invention, while FIG. 16B is a detailed view of the connecting element of the embodiment of FIG. 16B.

Figure 19:
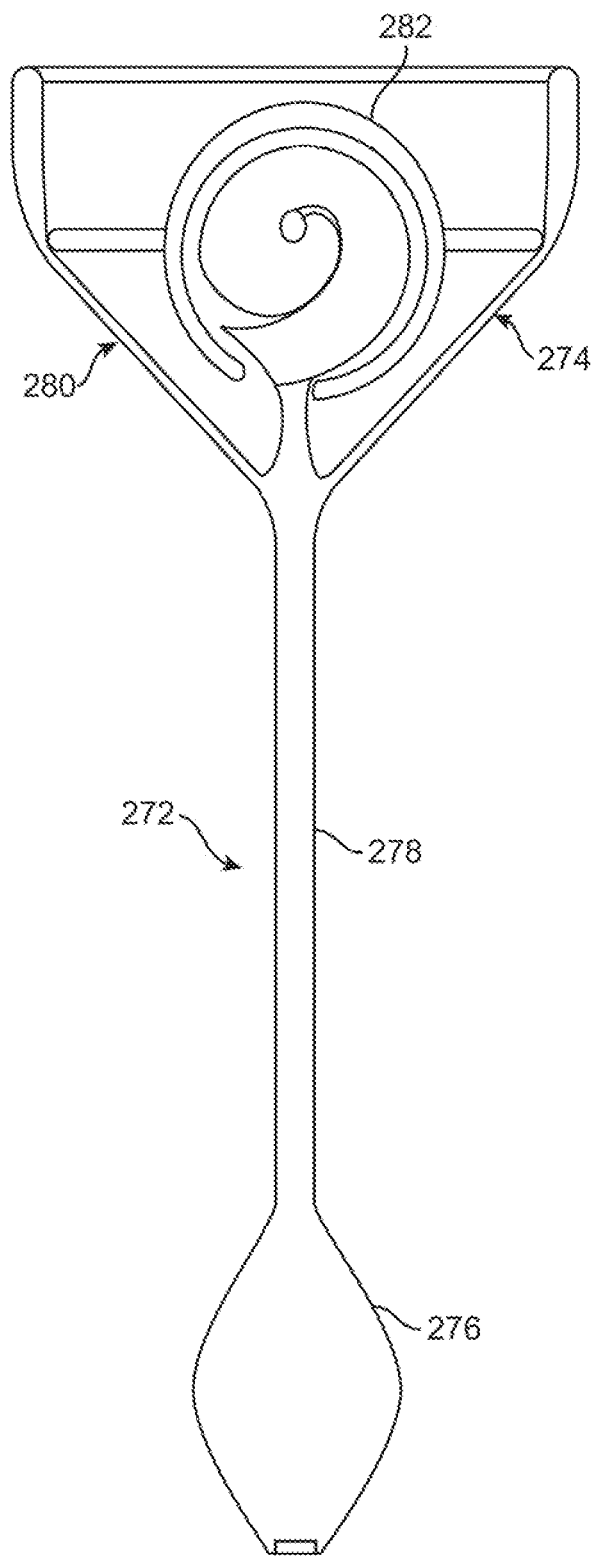
FIG. 19 is a cross-sectional view of a twelfth embodiment of the invention.

FIGS. 20A-20C; 21A-21B; and 22A-22C are side views of different embodiments of the first occluding member in the embodiment of FIG. 19 and of their mode of deployment.

Figure 23A:
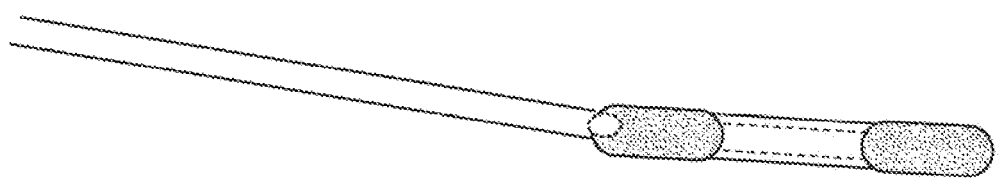
Figure 23B:
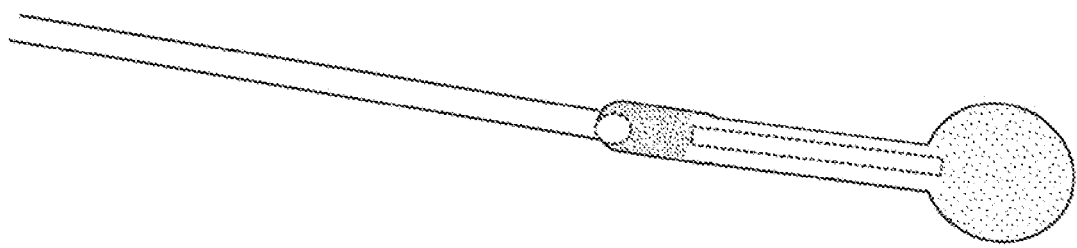
Figure 23C:
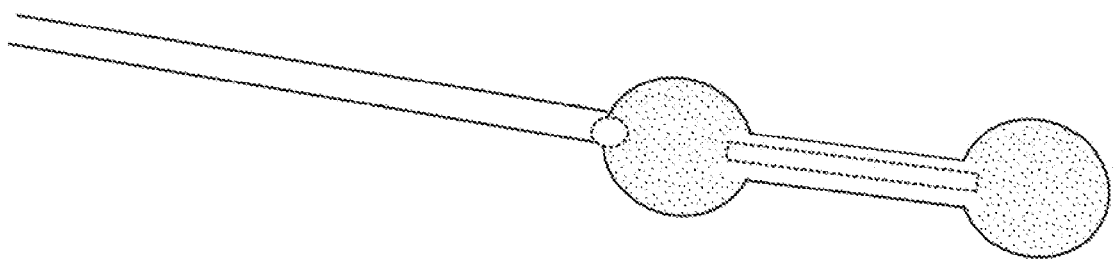

FIGS. 23A-23C illustrate a device introduced in the stomach or other part of the gastro-intestinal tract in an elongated configuration (FIG. 23A), expanded to an intermediate configuration (FIG. 23B) and to a final configuration (FIG. 23C) by injecting a foam with an appropriate catheter.

Figure 24A:
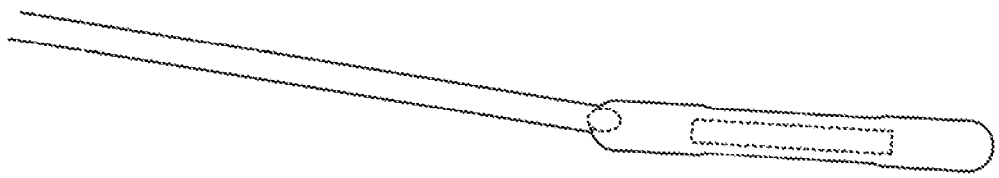
Figure 24B:
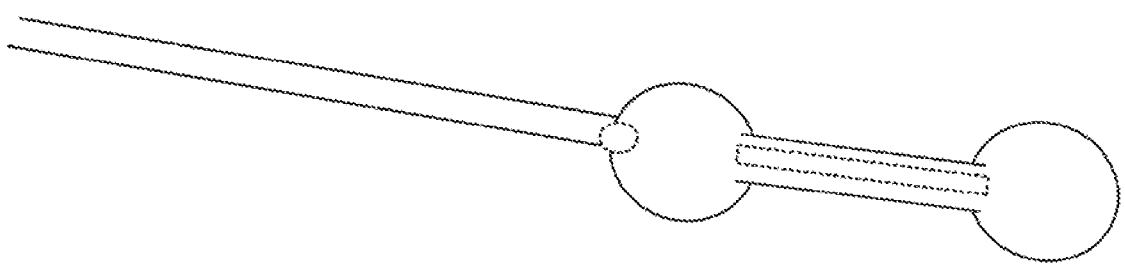
Figure 24C:
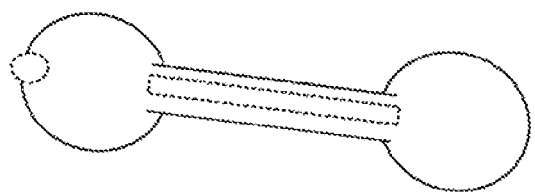

FIGS. 24A-24C illustrate a process similar to that of FIGS. 23A-23C, except that a substance such as water, a reagent and/or a catalyst is injected through the catheter.

Figure 25A:
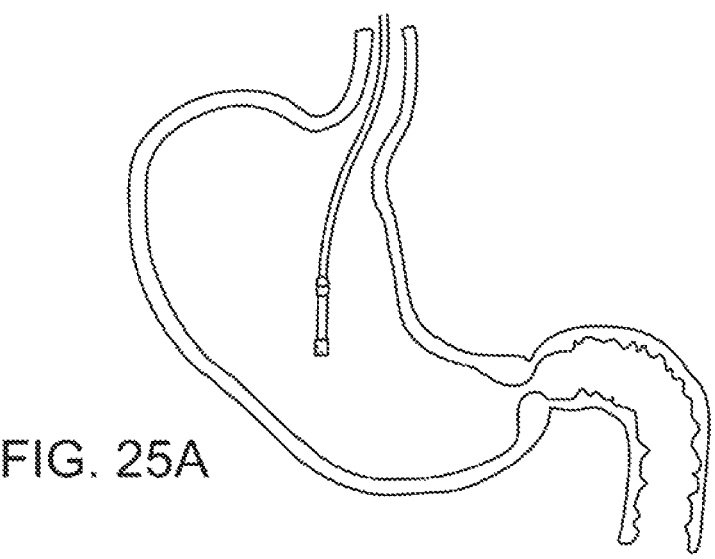
Figure 25B:
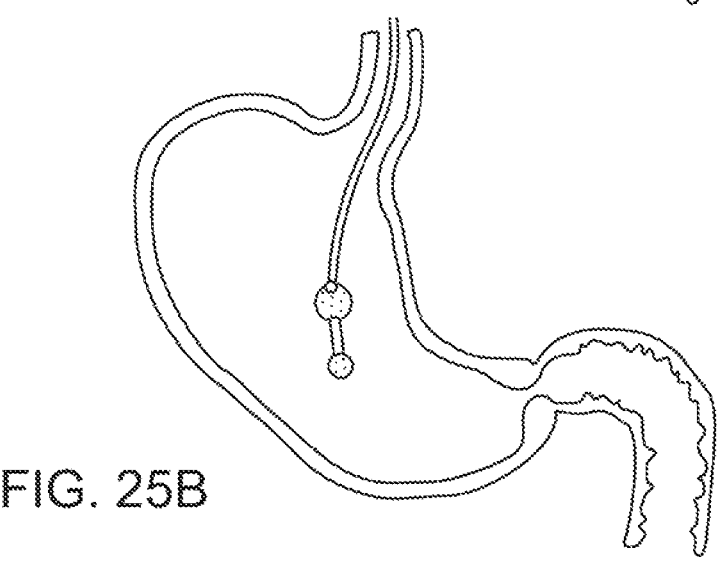
Figure 25C:
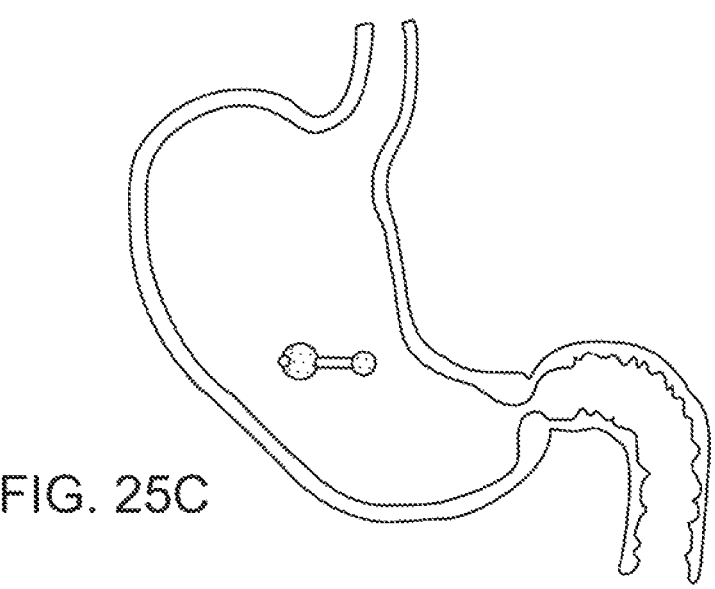

FIGS. 25A-25C illustrate schematically a mode of placement of the devices of FIGS. 23A-23C and 24A-24C through a catheter introduced through the esophagus (FIG. 25A), then used for infusing foam or a growth substance (FIG. 25B) and eventually causing the device to become fully inserted (FIG. 25C).

Figure 26A:
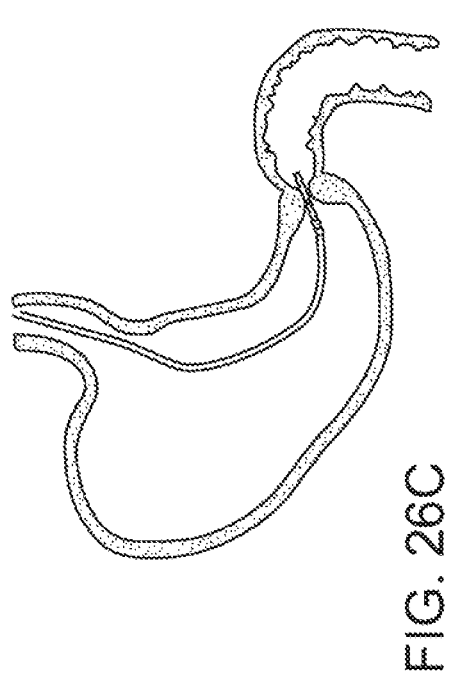
Figure 26B:
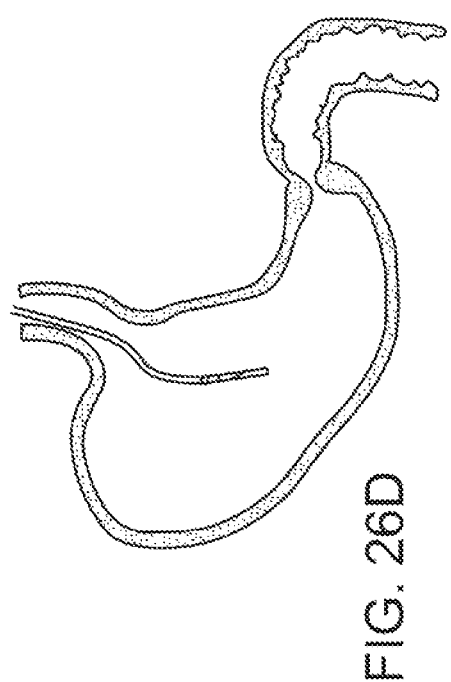
Figure 26C:
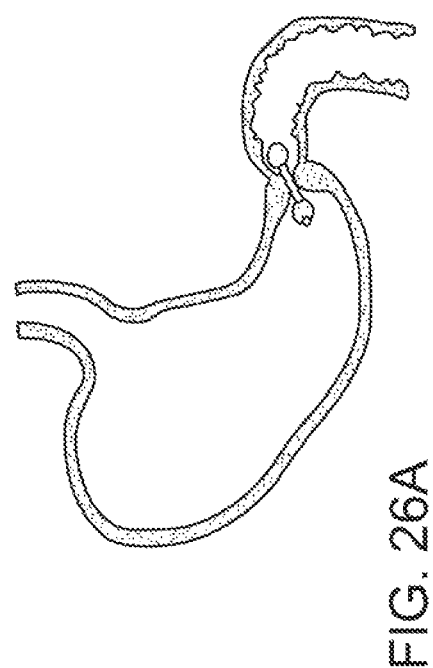
Figure 26D:
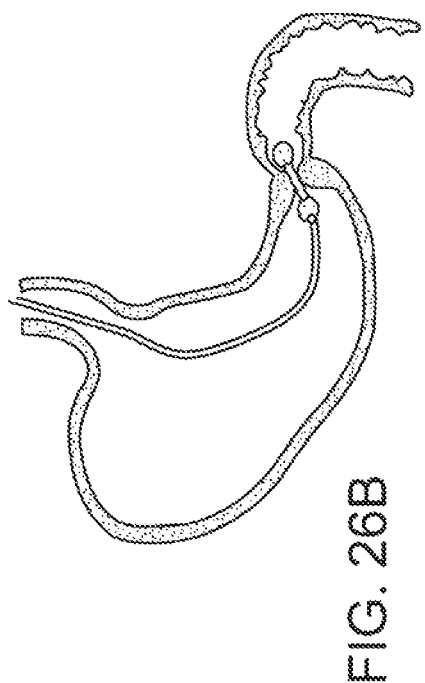

Conversely, FIGS. 26A-26D illustrate the removal of such a device by showing the device in its placed state (FIG. 26A), the attachment of a device extractor (FIG. 26B), the activation of predetermined failure points (FIG. 26C), and the extraction of the device (FIG. 26D).

Figure 27A:
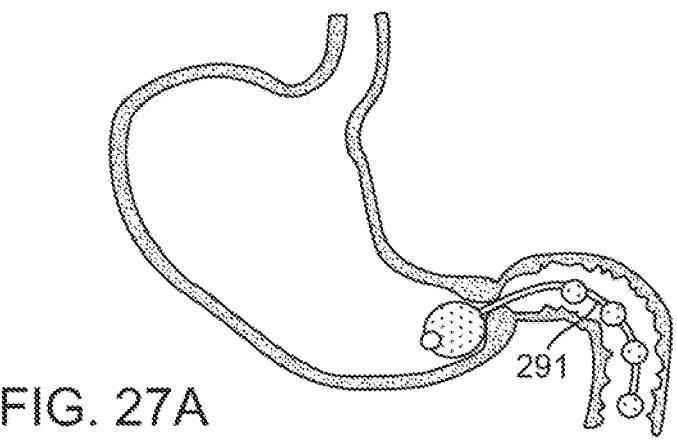
Figure 27B:
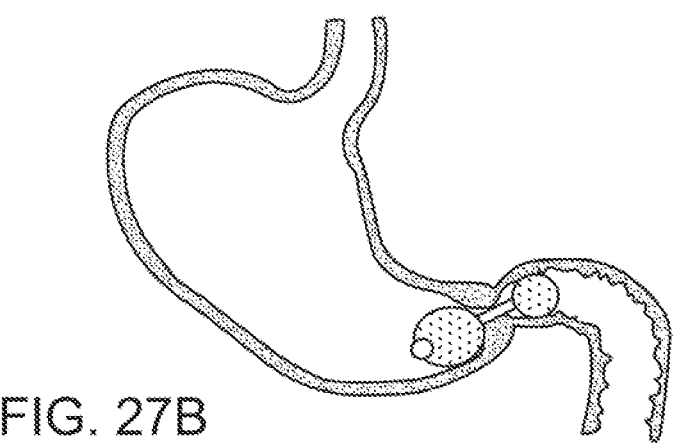
Figure 27C:
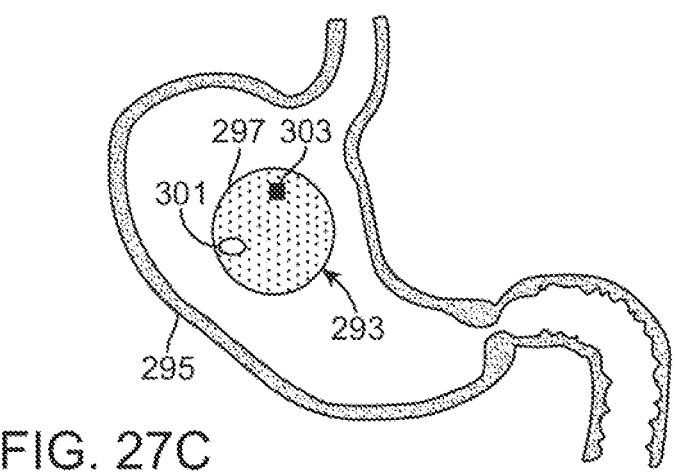

FIGS. 27A-27C illustrate other embodiments, in which multiple distal bulbs (FIG. 27A) or a larger distal bulb (FIG. 27B) may be present to slow transit of food in the gastro-intestinal tract, or in which no distal bulb may be present and the device can act as a space filler (FIG. 27C).

Figure 28A:
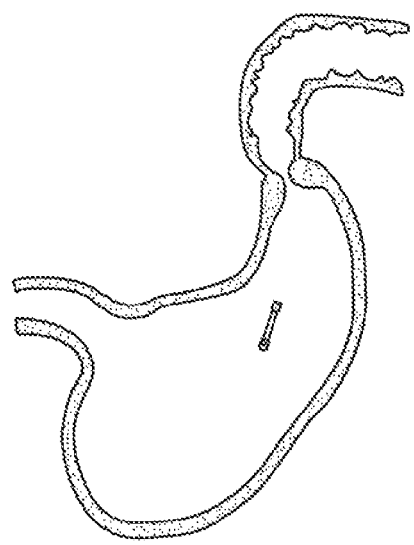
Figure 28B:
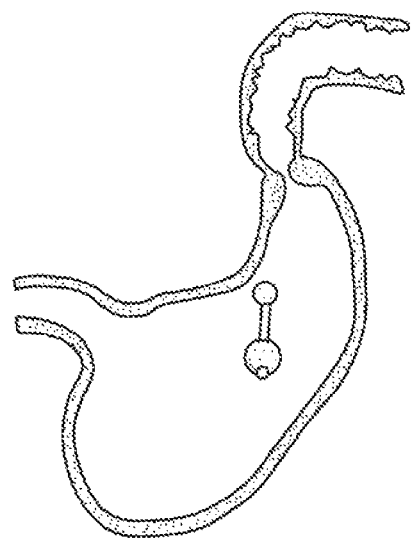
Figure 28C:
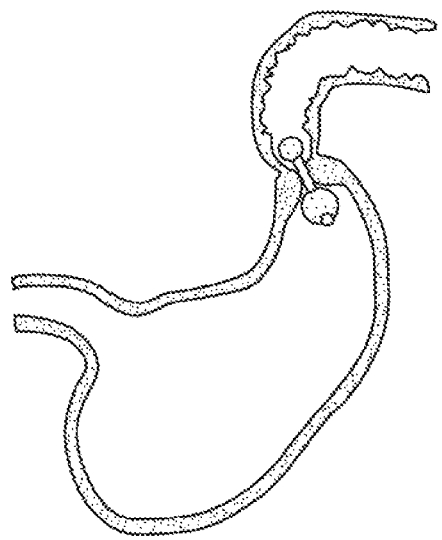
Figure 28D:
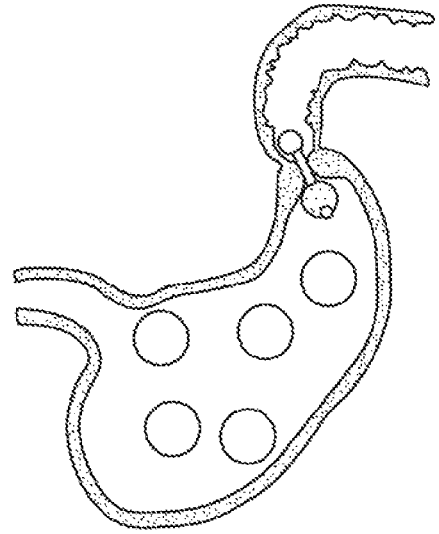

FIGS. 28A-28C illustrate a mode by showing insertion (FIG. 28A), inflation of the bulbs (FIG. 28B), and the intestinal migration of the distal bulb (FIG. 28C). FIG. 28D illustrates the obesity treatment enhanced by adding gastric fillers in the stomach.

FIG. 29A illustrates a cross-sectional side view of an embodiment where an occluding member may be folded within a receiving channel such that a distal protrusion is mated in a secured manner within a mating cavity.

FIG. 29B illustrates a cross-sectional side view of another embodiment where the distal protrusion is configured in a shape which resists or inhibits withdrawal from the mating cavity.

Figure 29C:
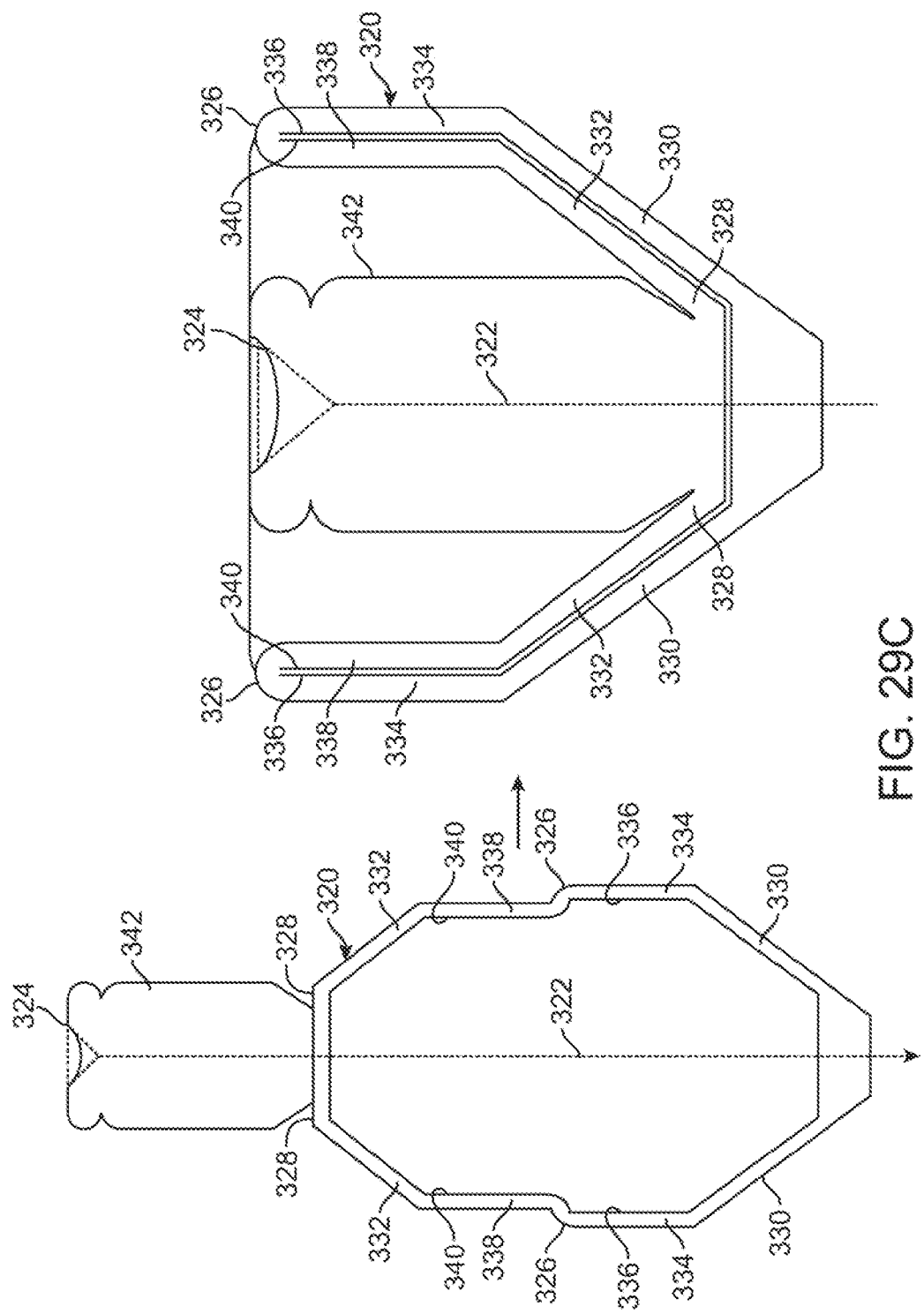

FIG. 29C illustrates cross-sectional side views of yet another embodiment where the device may be collapsed by actuation of a tensioning wire or string.

Figure 30A:
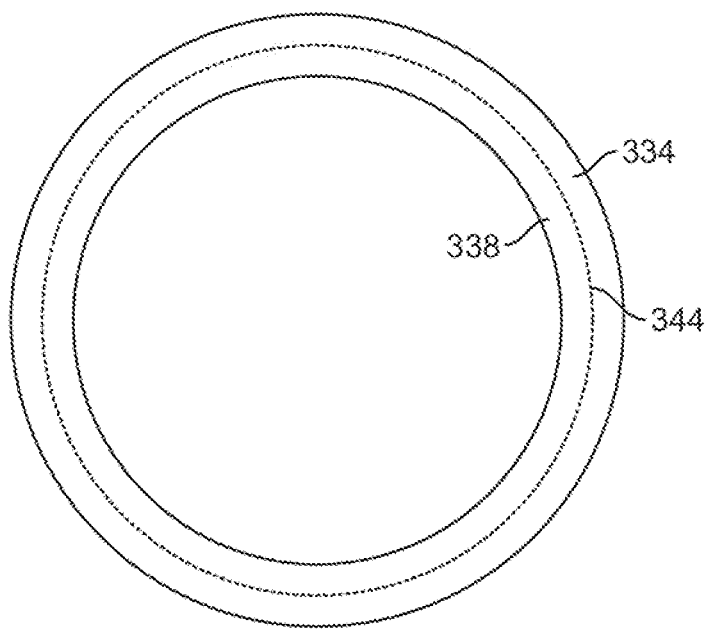
Figure 30B:
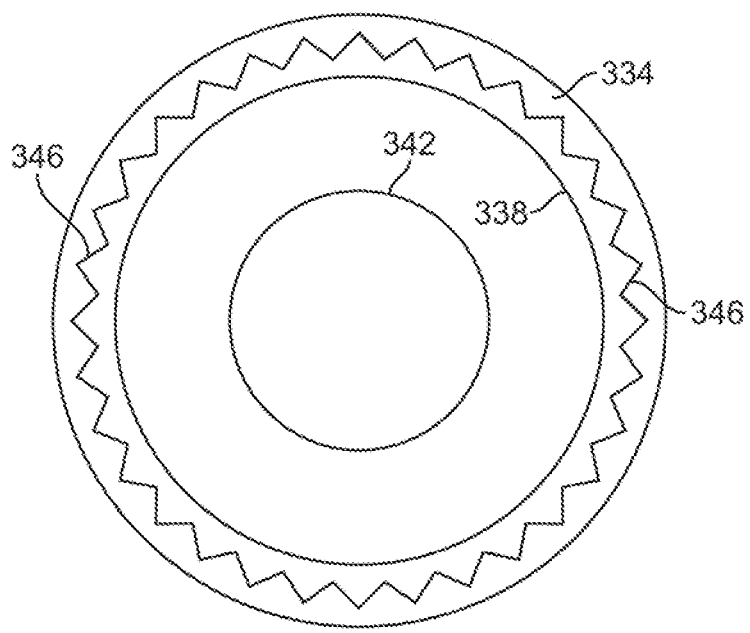

FIGS. 30A and 30B illustrate cross-sectional end views of alternative variations of the device of FIG. 29C where respective mating surfaces of the collapsed device may incorporate adhesion or interlocking surface features for securing the device in its collapsed configuration.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1A:
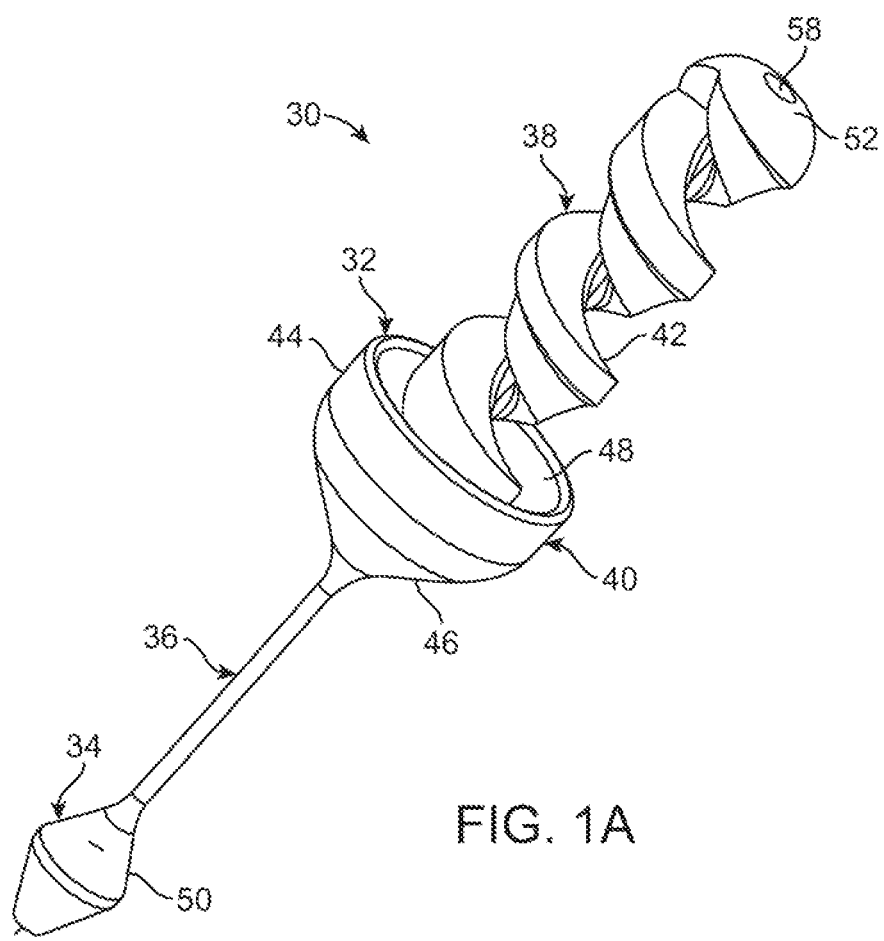
FIG. 1A illustrates a perspective view of a first embodiment of the invention in the elongated, narrower configuration.

FIG. 1A depicts a first embodiment of the invention, which is configured for insertion into a patient's organ, typically the stomach. Device 30 includes a proximal member 32 and a distal member 34, which are connected one to the other by a tether 36. The relative sizes of proximal member 32 and of distal member 24 are such that, after insertion into the stomach of a patient, the natural contractions of the stomach and, in general, the movements of the patient induce distal member 34 to enter the pyloric part of the gastro-intestinal tract and the duodenum, while proximal member 32 is retained in the stomach and cannot move beyond the pyloric valve because its diameter is larger than the pyloric valve opening.

Figure 1B:
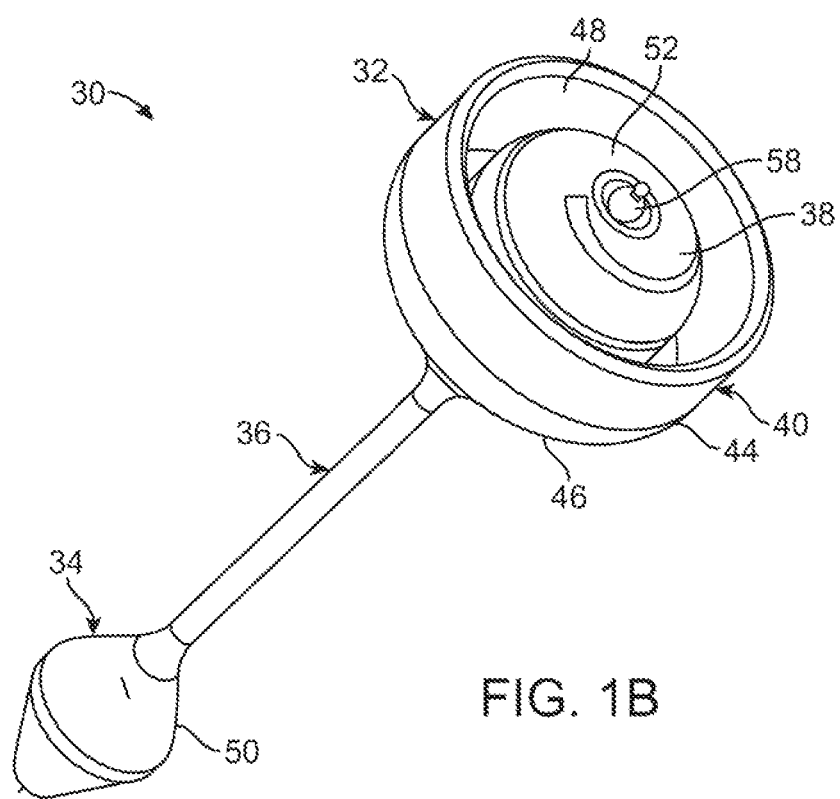
FIG. 1B illustrates a perspective view of the embodiment of FIG. 1A in the contracted, wider configuration.

More particularly, proximal member 32 includes a first occluding member 38, disposed in a central position within an apron member 40. First occluding member 38 may be formed from an elongated, narrower configuration as shown in FIG. 1A to a contracted, wider configuration as shown in FIG. 1B. In the embodiment illustrated in FIG. 1A, first occluding member 38 has a helical design with a plurality of turns 42, which are configured to nest one adjacent to the other to assume the compact, bulbous shape illustrated in FIG. 1B.

Apron member 40 wraps around first occluding member 38, providing proximal member 32 with a enlarged diameter and preventing the passage of proximal member 32 through the pyloric valve. In one variant of the present embodiment, apron member 40 includes an essentially cylindrical proximal portion 44 connected to an essentially conical distal portion 46 that extends from tether 36 to proximal portion 44. This configuration of apron member 40 is designed to provide an intermittent plugging effect on the pyloric valve and to avoid or anyways minimize abrasive contact with the wall of the pyloric valve during such plugging effect, so to prevent or minimize patient discomfort and irritations or even lacerations to the mucosa of the stomach and, in general, to the gastro-intestinal tract.

Distal portion 46 may have a smaller wall thickness than proximal portion 44, both providing a gentler, suppler contact with the pyloric valve, and also facilitating the reversal of apron member 44 during insertion into a patient's stomach from a position substantially aligned with tether 36 to the position that wraps around first occluding member 38, as explained in greater detail below.

In different variants of the present embodiment, apron member 40 may extend proximally for various lengths, surrounding first occluding member 38 partially or completely. Further, in different variants of the present embodiment, apron member 40 may be spaced from first occluding member 38 at various distances to create an interstice 48 of different amplitudes between first occluding member 38 and apron member 40.

Second occluding member 34 may exhibit a variety of contours and in general, is shaped to facilitate its transition out of the stomach and into the duodenum, and to avoid or minimize abrasive contact with the walls of the stomach and of the pylorus. In one embodiment, second occluding member 34 has a bulbous shape, essentially formed by two rounded, frusto-conical portions 50 connected at their wider bases.

Device 30 may be manufactured from a variety of materials, for example, from a resilient plastic such as a silicone or urethane plastic, which may be reinforced in selected portions. In general, the selected material should be biocompatible, resistant to the stomach environment, for example to stomach acids, and soft to the contact with the stomach and duodenal walls. The desired material should also provide device 30 with the desired shape while retaining sufficient flexibility for the insertion process in the stomach, for later reverting to the desired position within the gastro-intestinal tract, and for adapting to the various movements of the stomach and, in general, of the body of the patient.

Inserts may be integrally included within the body of device 30 to increase certain mechanical properties in certain areas. For example, an insert (such as a metallic cylinder) may be embedded within second occluding member 34 to increase weight and to facilitate retention by gravity within the pylorus. Another insert (such as a fabric piece) may also be embedded in proximal end 52 of first occluding member 38, increasing resistance to tear when proximal end 52 is pulled outwards to extend first occluding member to the configuration of FIG. 1, or inwards to stabilize first occluding member in its contracted, wider configuration, as explained in greater detail below.

Figure 1C:
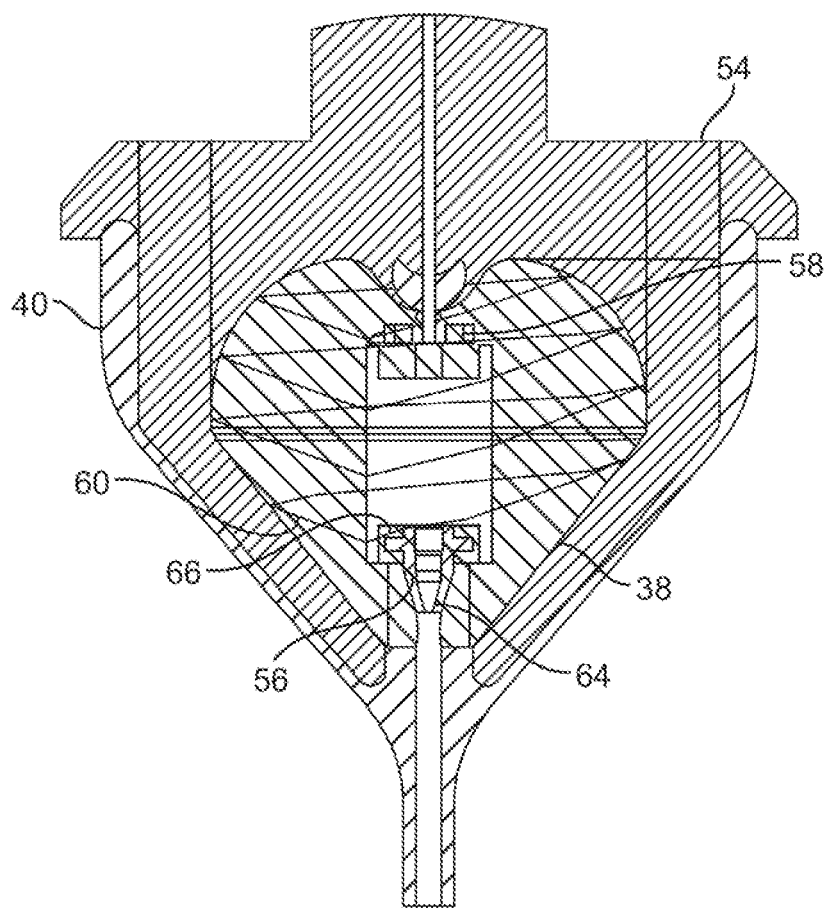
FIGS. 1C-1E illustrate respectively a cross-sectional view of the proximal member of the embodiment of FIG. 1B, to which a protective cap has been added (FIG. 1C); a side view of the embodiment of FIG. 1B with the protective cap (FIG. 1D); and a cross-sectional view of the embodiment of FIG. 1D (FIG. 1E).
Figure 1D:
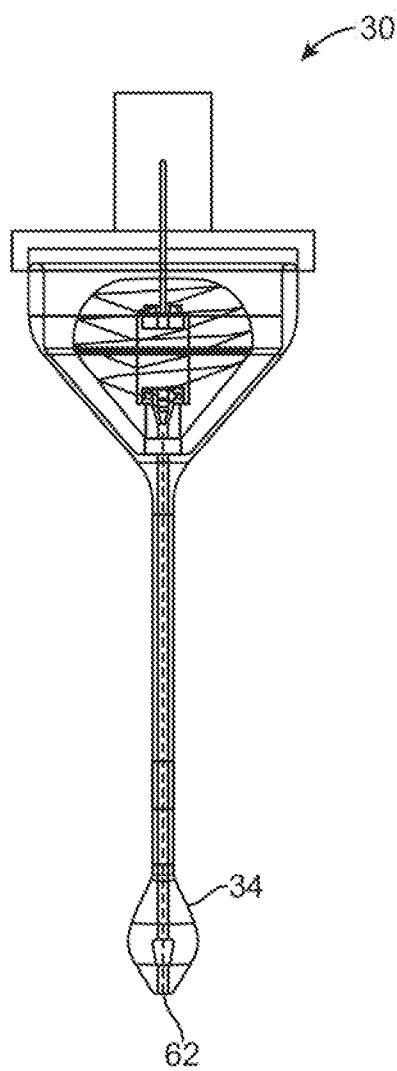
Figure 1E:
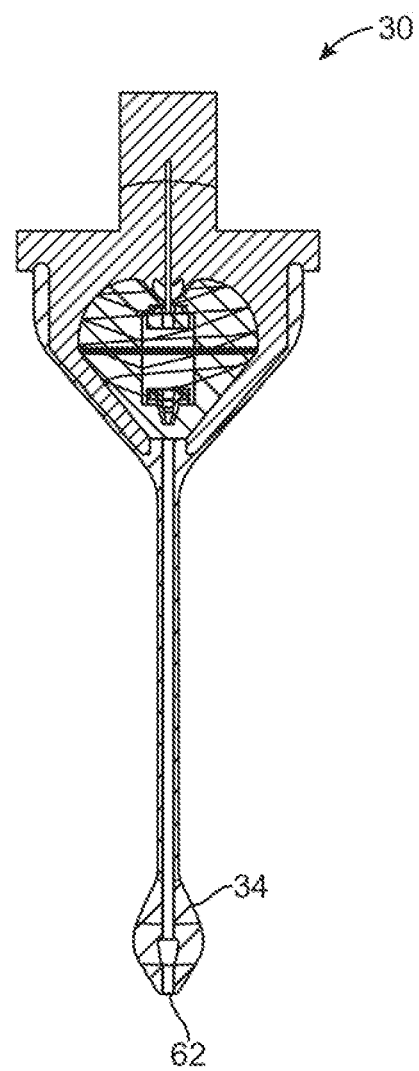
Figure 1F:
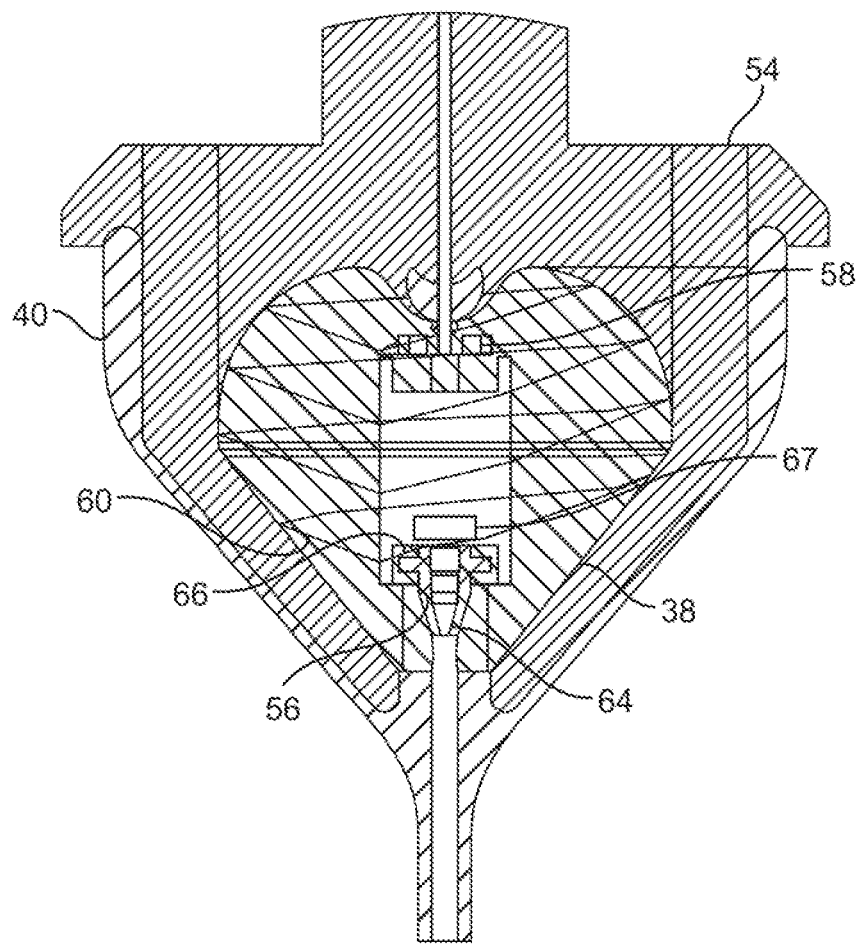
FIG. 1F illustrates a cross-sectional side view of one example of a device having a sensor incorporated within for confirming or detecting whether the occluding member has been locked into its deployment configuration.

The insertion of device 30 in a patient's stomach will now be described with reference to FIG. 1C. It should be noted that FIG. 1C illustrates, among other things, one variant of the embodiment of FIGS. 1A and 1B, in which a stabilizing cap 54 is added to maintain first occluding member 38 in the contracted, wider configuration, and also to increase bulk and to prevent the introduction of food or other gastric products within interstice 48.

In one method of use, device 30 is introduced in a patient's stomach in the elongated, narrower configuration of FIG. 1A, with apron member 40 oriented in the opposite direction to that shown in FIG. 1A, that is, to cover tether 36 while the free end of distal portion 46 is oriented proximally, in the direction of second occluding member 34. When in this configuration, device 30 is disposed within a tube (not shown) and is caused to exit the tube with proximal end 52 first, followed by the rest of the device. When device 30 has partially exited the tube (or alternatively, the tube has been retracted from device 30) so to leave apron member 40 outside of the tube, device 30 is pulled inside the tube, but because apron member 40 surrounds and wraps around the end of the tube, such a pulling of device 30 inwards into the tube, causing apron member 40 to flip over and change orientation, so to wrap around first occluding member 38. After such a flipping around of apron member 40 has been achieved, device 30 is completely ejected from the tube and becomes disposed in the stomach. Alternatively, device 30 may be introduced in a patient's stomach with apron member 40 already oriented proximally, making unnecessary the previously described flipping operation.

While the configuration of first occluding member 38 makes it recoil and assume the contracted configuration, similar to that shown in FIG. 1B, the fully contracted, wider configuration of first occluding member 38 is achieved and maintained as follows. A connecting member 56 is coupled (for example, by a first string) to a release member 58. A second string 60 is looped around device 30, running outside and along device 30 starting from a first free end, and then extending within connecting member 56 through lumen 66, and then (within a lumen or a tube) within turns 42, successively entering a lumen 62 in tether 36 and second occluding member 34 (see also FIGS. 1D and 1E), and eventually exiting device 30 with a second free end.

After device 30 has been introduced in the stomach, a clinician can hold both ends of second string 60 and, by pulling on second string 60 while device 30 is constrained within the stomach, the clinician causes connecting member 56 to travel in the direction of mating cavity 64, shaped so to constrain connecting member 56 (for example, by interference fit) and to prevent connecting member 56 from being released. Therefore, first occluding member 38 is locked into its contracted, wider condition on a permanent basis.

After device 30 has been shaped as described, second string 60 is removed by pulling on one free end and by having second string 60 slide through the lumens within device 30, eventually exiting device 30 entirely. Device 30 is now free to move freely within the stomach, and the natural contractions of the stomach, in addition to any other movements of the patient's body, cause distal member 34 to move into the pylorus, while the size of proximal member 32 prevents it from moving into the pylorus and forces it to reside in the stomach. Therefore, distal member 34 will eventually be disposed in the pylorus, and any inserts of a heavier weight will facilitate retention of distal member 34 in the pylorus, while proximal member 32 will act as an intermittent plug against the pyloric valve, because stomach contractions and other body movements will cause proximal member 32 to move towards and away from the pyloric valve, acting as an intermittent plug and allowing the passage of some food from time to time.

Figure 2D:
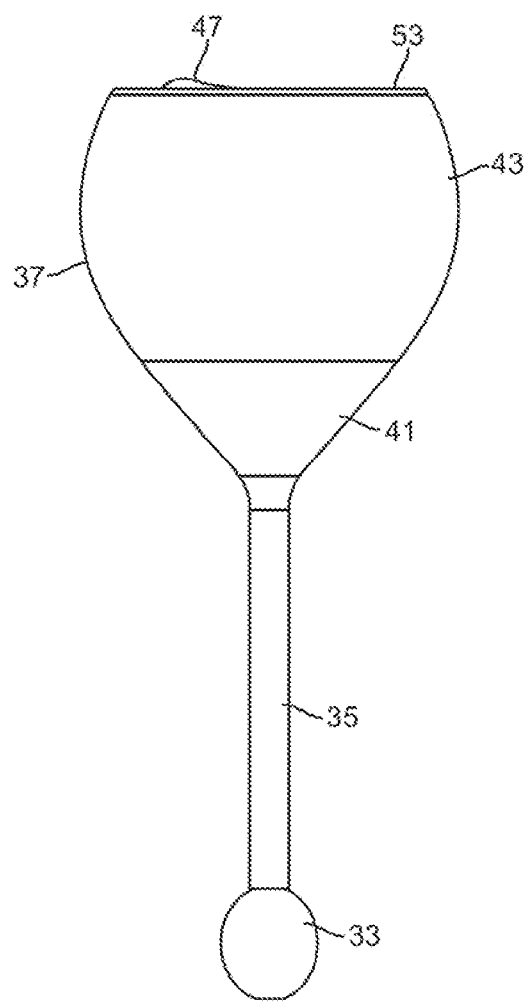
FIGS. 2D-2E illustrate respective side and cross-sectional perspective views of the embodiment of FIGS. 2A-2C.
Figure 2E:
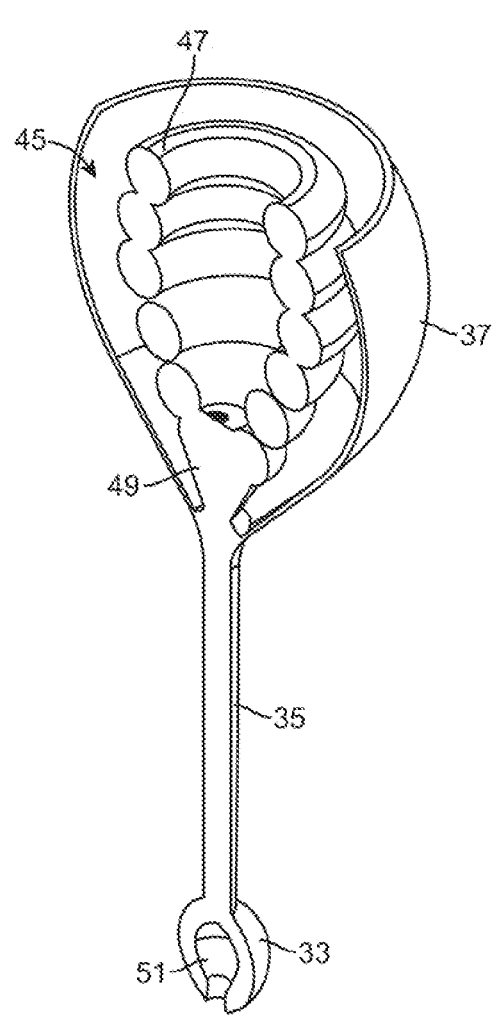

Another embodiment is illustrated in the cross-sectional side view of FIG. 2A and the top and bottom end views, respectively, of FIGS. 2B and 2C. In this embodiment, device 31 may also include a distal member 33 connected or attached via tether 35 to proximal member 37. As described above, proximal member 37 may comprise an apron member 39 which defines a curved or otherwise arcuate surface which tapers radially from tether 35 at a distal portion 41 (which typically contacts the stomach interior surface when in use) to a curved proximal portion 43 which has a relatively larger diameter and which may define a circumferential lip or edge 53 which is atraumatic to surrounding tissue. Apron member 39 may define a channel or interstice 45 within which first occluding member 47 may reside when occluding member 47 is in its contracted deployment configuration, as illustrated. With occluding member 47 contracted, apron member 47 may be configured to entirely or at least partially encircle or enclose occluding member 47, as illustrated in FIGS. 2D and 2E which respectively show side and cross-sectional perspective views. Moreover, interstice 47 may be left open when in use in the patient body or an additional cap member or covering may be optionally attached to fully enclose apron member 39 and occluding member 47 within, if so desired.

Occluding member 47 may be formed into a coiled or wound structure having a plurality of turns and a distal end which is attached, coupled, or otherwise formed integrally with device 31 at connecting portion 49. Because of its coiled or wound helical structure, occluding member 47 may be extended in a low-profile configuration, as above, for delivery into the patient body and then allowed to compress or contract into its coiled structure which forms a diameter or cross-sectional area which is relatively larger than a diameter of distal member 33 to inhibit or prevent the passage of proximal member 37 through the pylorus when in use. As in the aforementioned embodiment, occluding member 47 may be biased or configured to self-contract. Alternatively, a string member or other locking mechanism, as described herein, may be actuated to compress and/or lock the structure such that the expanded configuration is maintained and prevented from releasing and reconfiguring back into its low-profile configuration. Distal member 33 may further define a lumen or channel 51 to facilitate the placement and/or positioning of device 31 within the patient body.

Figure 3A:
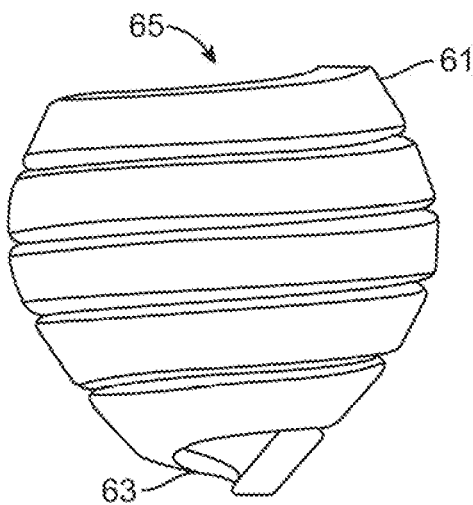
FIGS. 3A-3B illustrate side and cross-sectional side views, respectively, of yet another embodiment where an occluding member is separately fabricated and removably attachable within an apron member.
Figure 3B:
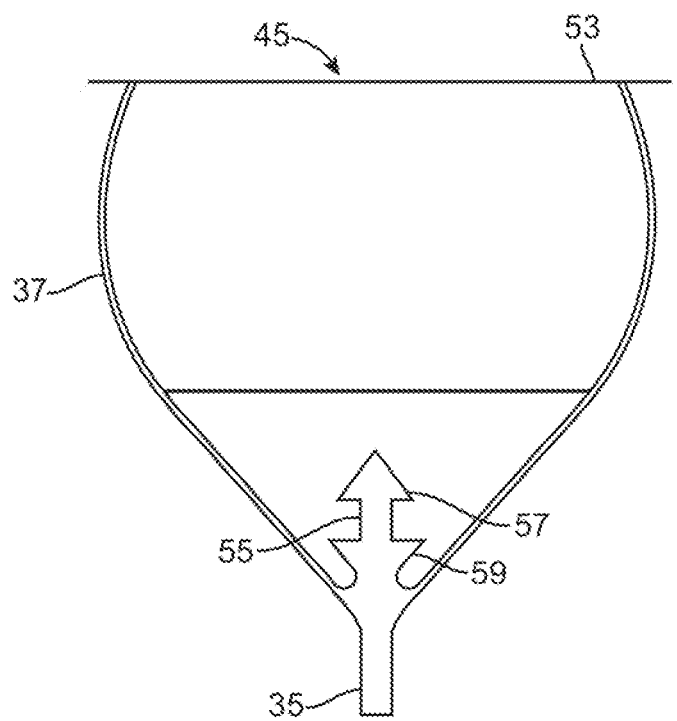

In yet another embodiment, the occluding member may be fabricated as a separate component and attached or coupled within the apron member at a later time rather than forming the occluding member as a continuous integral component. This particular embodiment allows for the size and shape of the occluding member to be varied and altered according to any patient-specific parameters and attached within a common apron member. As shown in the side view of FIG. 3A and the cross-sectional side view of FIG. 3B, occluding member 61 may be formed as a coiled or wound helical structure which defines a channel 65 and a receiving portion 63 when in its collapsed deployed configuration. As previously described, occluding member 61 may be advanced into the patient body in an extended low-profile configuration and then collapsed into its expanded and optionally locked configuration, as shown, either via actuation or by allowing for self-reconfiguration.

Because the coiled portion of occluding member 61 may form a receiving portion 63 in its collapsed configuration, portion 63 may be coupled to a complementary securement mechanism positioned within apron member 37. In this example, the securement mechanism may be comprised of a connecting portion 55 which extends distally within apron member 37. Connecting portion 55 may have a securement member 57, such as a tapered portion, and a stop member 59 which each limit the movement of portion 63 relative to connecting portion 55.

Figure 3C:
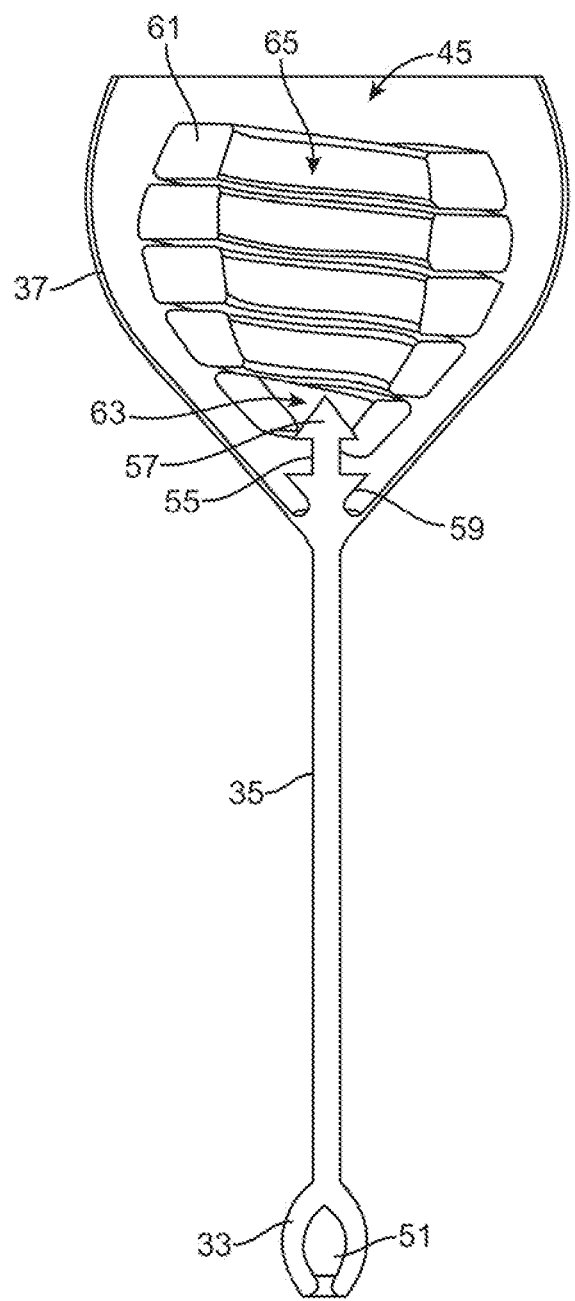
FIG. 3C illustrates a cross-sectional side view of an assembled device from FIGS. 3A and 3B.

As illustrated in the cross-sectional side view of FIG. 3C, occluding member 61 is shown in its collapsed and locked configuration while secured within interstice 45 and encircled by apron member 37. As shown, securement member 57 may be advanced at least partially within channel 65 formed by the wound occluding member 61 to prevent the relative movement or release of occluding member 61 from connecting portion 55. The connecting portion 55 is illustrated as an example and is not intended to be limiting. Other known securement mechanisms may be utilized as practicable.

In these and other embodiments described herein, because the device may be introduced into the patient body in a minimally invasive manner, e.g., per-orally and through the esophagus into the patient's stomach, the device may be delivered in its low-profile configuration, e.g., where the occluding member is in its uncoiled or unwound elongate configuration. Alternatively, the device may be delivered in a partially locked configuration. Once within the stomach, for instance, the device may be coiled or wound into its deployment configuration and the occluding member may be affirmatively locked into position relative to the device such that its enlarged profile inhibits or prevents the passage of the device through the pylorus. In ensuring that the occluding member is locked into its expanded configuration, various mechanisms may be utilized to confirm its securement.

One example includes having the string for locking the occluding member be color-coded such that one portion of the string is of a different color, e.g., red, than the remainder of the string. As the string is tensioned to lock the occluding member, once the color-coded portion is exposed from the device the user may visually confirm that the occluding member is locked into its deployment configuration. Alternatively, the amount of tension required to lock the device may be calibrated to increase to a preset level once the device is locked such that the user may confirm by tactile feedback that the device is indeed locked.

Other alternative mechanisms for locking confirmation or detection of the occluding device may additionally include sensors incorporated within the device. An example is illustrated in the cross-sectional side view of FIG. 1F, which shows sensor 67 positioned within the device. Sensor 67 may incorporate any number of detection modalities, e.g., acoustic, ultrasonic, electrical, electromagnetic, optical (for instance, detecting changes in color, wavelength, frequency, etc.), chemical, etc. which may sense changes in the occluding member from its coiled deployment configuration or changes in the string tension, connecting member 56, or release member 58.

Based on the foregoing, device 30 (and variations thereof) assists in the treatment of obesity by limiting the passage of food from the stomach into the intestine, and at the same time by reducing the intake of food by the patient due to the sense of fullness generated by the retention of food in the stomach for a longer time and also by to the presence of device 30 in the stomach.

Figure 4:
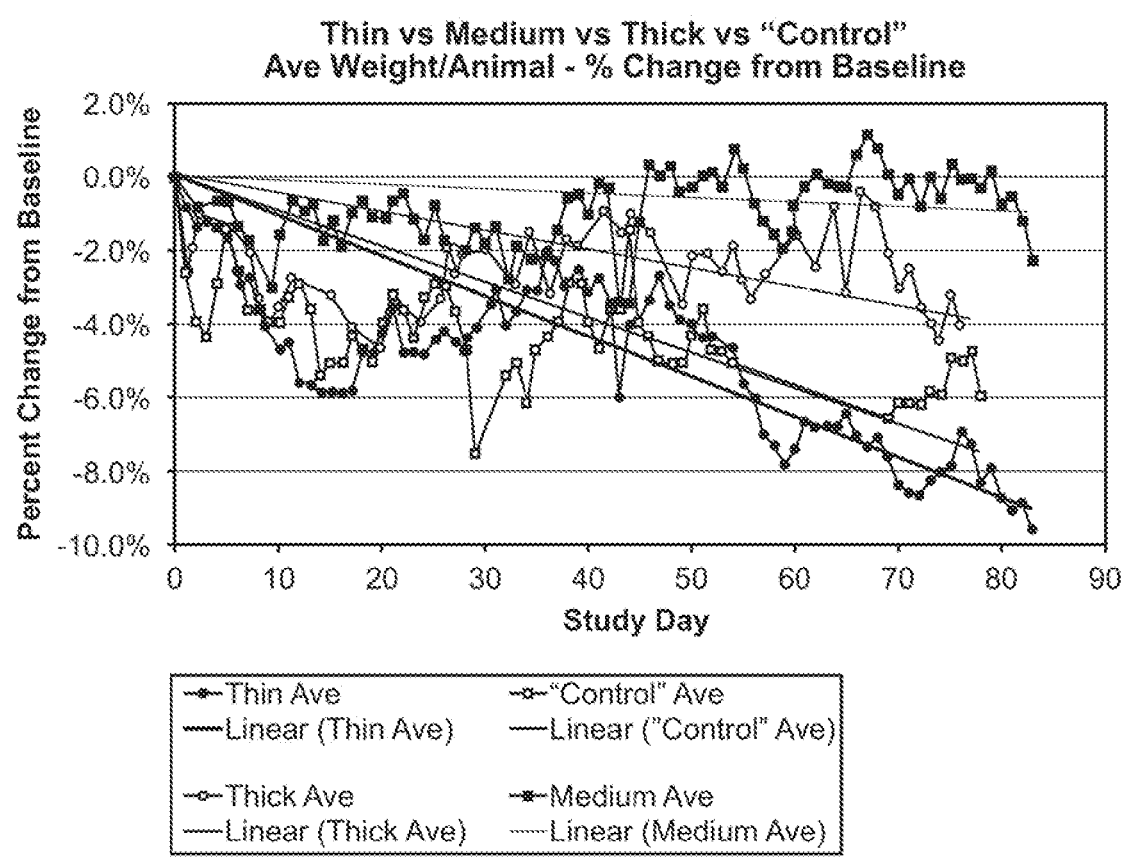
FIG. 4 is a graph depicting the efficacy of the first embodiment of the invention in different variants.

Experiments performed with the above-described embodiments indicate a "dose-response" relationship between the thickness of the wall of distal portion 46 and weight loss of the patient. For example, a series of experiments performed on dogs and summarized in FIG. 4 indicate that the greater the thickness of the wall of distal portion 46, the greater the rate of weight loss.

In one version of the present embodiment, apron member 40 has a total length of 38 mm, with the proximal (cylindrical) portion having a length of 15 mm and an outer diameter of 53 mm, and the distal (conical) portion having a length of 23 mm. The first occluding member 38 has, in its contracted configuration, both a length and a width of 35 mm, while distal member 34 has a length of 25 mm and a diameter of 15 mm, with device 30 having a total length of 142 mm. In this version, the wall of the distal portion 46 of apron member 40 may have a thickness of 1.3 mm for a maximum rate of weight loss, of 0.9 mm for a medium rate of weight loss, and of 0.5 mm for a lower rate of weight loss.

After device 30 has achieved its desired result, or when it becomes desirable to remove device 30 for any reasons, different removal options are available to a clinician. One removal option is surgical removal, for example, laparoscopic surgical removal. Another option involves removal through the esophagus and the throat by causing first occluding member 38 to reverse from its contracted, wider configuration to its elongated, narrower configuration. To achieve such change of configuration, proximal end 52 of first occluding member 38 must become disengaged from connecting member 56, which is also engaged in cavity 64. As previously described, connecting member 56 is coupled (for example, with the first string) to release member 58, making it possible to disengage proximal end 52 from connecting member 56 by severing the coupling (for example, the first string) between connecting member 56 and release member 58. This can be achieved through a procedure performed by introducing an appropriate surgical catheter (as known to a person skilled in the art) in the stomach of the patient through the esophagus, with the assistance of an endoscope, by severing the coupling between connecting member 56 and release member 58, and by successively removing device 30 through the esophagus.

While the present embodiment has been described in relation to obesity treatments, it must be noted that treatments of other ailments through device 30 are also possible. Examples of such treatments include treatments to restore normal glucose tolerance to a diabetic or prediabetic subject, or to delay or prevent the progression of diabetes in a subject, by inhibiting fasting insulin secretion or glucose-stimulated insulin secretion. Other examples of such treatments include the treatments of patients suffering from one or more diseases characterized by obesity including hyperphagia, dyslipidemia, Prader Willi syndrome, Froelich's syndrome, Cohen syndrome, Summit syndrome, Alstrom syndrome, Borjesen syndrome, Bardet-Biedl syndrome, and hyperlipoproteinemia, types I, II, III, and IV.

In different variants of the present embodiment, various ancillary components may be included, such as sensors, miniature motors, or reservoirs. In one variant, a sensor may be placed in line with the locking string to provide feedback information about the unexpected unlocking of the first occluding member from its contracted configuration, indicating a failure of the locking mechanism. In another variant, a miniature eccentric motor may be included that generates a vibrating sensation, for example, when a patient ingests an excessive amount of food and food in excess of a predetermined threshold has accumulated towards the pyloric valve. In still another variant, a reservoir containing a therapeutic substance may be included that releases that substance over time, or a reservoir of a mildly irritating substance, that may be temporarily opened for release into the stomach when a sensor perceives the ingestion of an undesired substance, such as sugar, so to generate an unpleasant reaction in the patient and break the habit of ingesting the undesired substance. The motor or the reservoir may be refilled with power, and/or the reservoir may be refilled with the desired substance, through a catheter introduced in the esophagus and into the stomach or in the case of the motor, through telemetric energy transmission. Communication devices, data receivers, data storage modules, microprocessors and rechargeable power sources also may be included in device 30. A therapeutic substance may also be impregnated into the walls of device 30 to be eluted over time.

Figure 5:
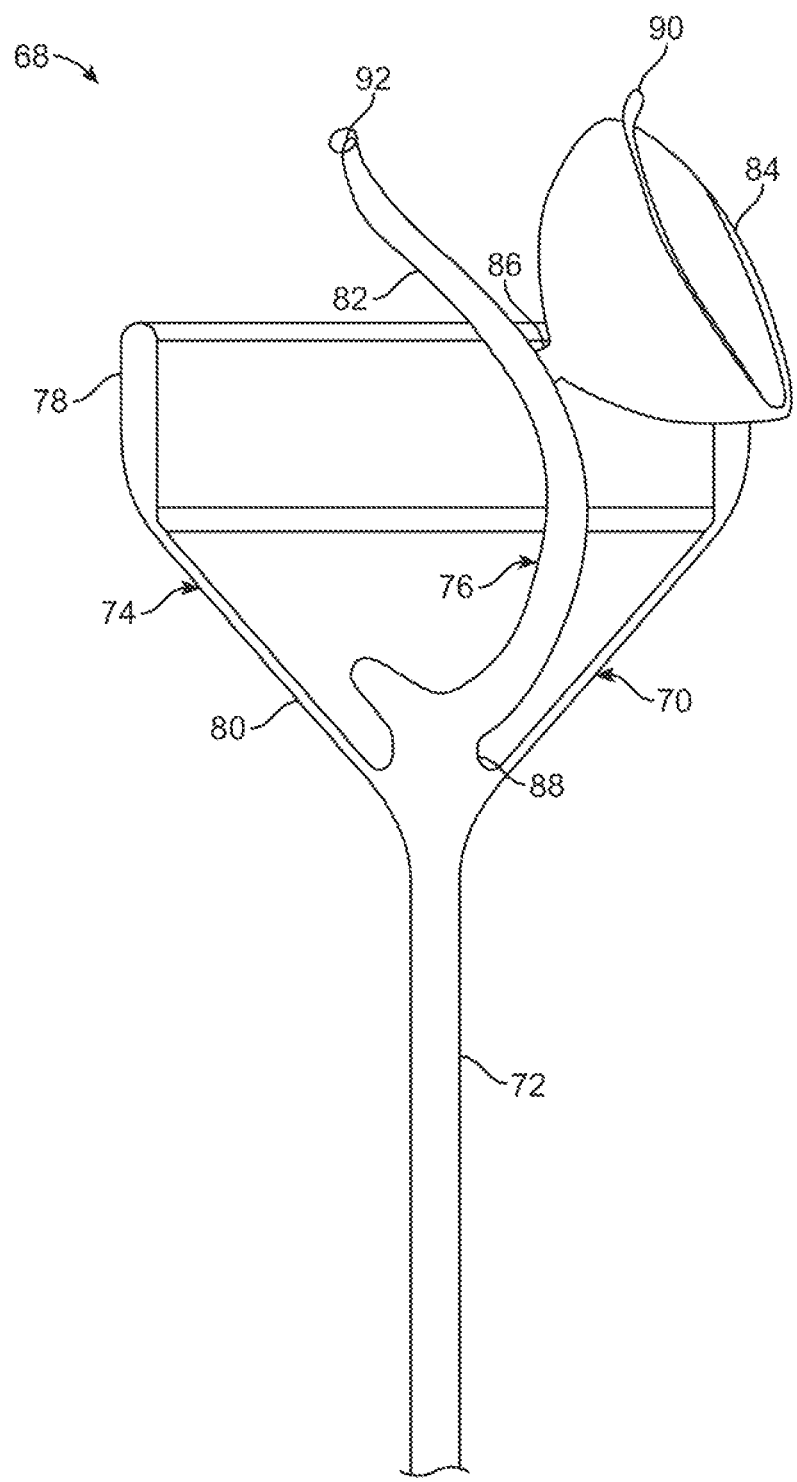
FIG. 5 is a partial cross-sectional side view of the proximal portion of a second embodiment of the invention.

Another embodiment of the present invention is depicted in FIG. 5. The basic components of device 68 include a proximal member 70, a tether 72 and a distal member (not shown) at the end of tether 72 opposite to proximal member 70. Parts of this embodiment and of the embodiments described hereinafter are common with the previously described embodiments, and will not be described again here for the sake of brevity.

Proximal member 70 includes apron member 74, which surrounds first occluding member 76 and which is composed of a proximal, cylindrically shaped portion 80 and of a distal, conically-shaped portion 78 that connects proximal portion 80 to tether 72. First occluding member 76 includes a support member that extends from the tip of distal portion 78 (which corresponds to the proximal end of tether 72) into the inner portion of apron member 74, and a cup-shaped member 84 that is connected to support member 82 approximately midway and that has a concavity facing proximally, with cup-shaped member 84 being joined to support member 82 by first joint 86. In turn, support member 82 is joined to the distal end of distal portion 78 (which corresponds to the proximal end of tether 72) by second joint 88.

FIG. 5 illustrates the elongated, narrower configuration of device 68 prior to introduction in the stomach or other organ of a patient. In this elongated, narrower configuration, device 68 has apron member 74 oriented distally (towards the second occluding member), which requires that apron member 74 be reversed to change orientation and to become directed proximally, as shown in FIG. 5 and as described in relation to embodiment 30. Alternatively, apron member 74 may be oriented proximally even during introduction into the stomach of the patient.

After introduction in the stomach, first occluding member 76 is caused to assume a contracted, wider configuration through the use of a string, as described in relation to embodiment 30, that runs outside of device 68 then through first ring 90 on an edge of cup-shaped member 84 and further through second ring 92 at a proximal extremity of support member 82, and still further through a lumen within tether 72 and within the second occluding member. By pulling on the free ends of that string, support member 82 is caused to arch in the direction of second joint 88, acquiring and essentially closed shape, and cup-shaped member 84 is caused to flip around, reversing orientation and overlaying the essentially closed shape of support member 82.

Therefore, first occluding member 76 is caused to acquire a convex, layered structure, with the cusp oriented proximally. As in embodiment 30, second ring 92 or a connecting member are caused to engage a cavity or other structure in the area of second joint 88, becoming permanently engaged. Also as in embodiment 30, removal of device 68 from the stomach may be achieved through surgical intervention, or alternatively through the esophagus by causing device 68 to revert to the narrower, elongated configuration by severing a string or other retainer that connects the connecting member to a release member.

Figure 6A:
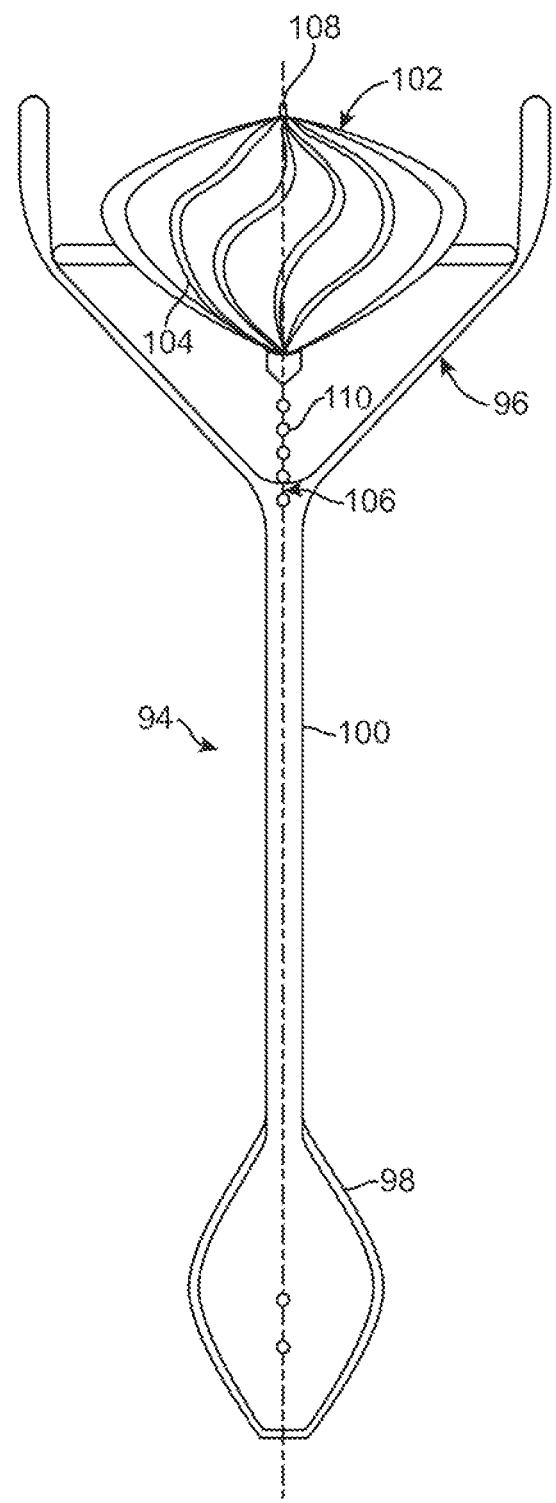

A third embodiment of the invention is depicted in FIGS. 6A-6B, FIG. 7 and FIG. 8. Device 94 includes, as in the previous embodiments, a proximal member 96 and a distal member 98 connected by a tether 100. In device 94, first occluding member 102 includes a plurality of struts 104, that may be formed as individual struts connecting the proximal and distal ends of first occluding member 102, in the fashion of the ribs of a cage, or that may be formed as sheets extending from the longitudinal axis of first occluding member 102, in the fashion of pages of a book. In one version of device 94, struts 104 are manufactured from a silicone material, that is biocompatible and that can withstand the gastric environment. A silicone material also can also enable changes of curvature ranging between the elongated, narrower configuration of FIG. 8, the intermediate configuration of FIG. 7, and the contracted, wider configuration of FIG. 6A. Like in the previous embodiments, first occluding member 102 is structured to be inserted in, and removed from, an organ such as the stomach when it is configured in the elongated, narrower configuration of FIG. 8 and after it has been placed in the stomach or other organ, to be reconfigured into the contracted, wider configuration of FIG. 6A. This change of configuration is achieved by having a string 106 disposed around and through device 94, in particular, through first occluding member 102 and through lumens in tether 100 and in distal member 98. Alternatively, string 106 may be connected to the proximal end of first occluding member 102 and run through lumens in tether 100 and distal member 98. By pulling on string 106 when first occluding member 102 is in the elongated, narrower configuration of FIG. 8, struts 104 are caused to flex and to provide first occluding member 102 with the rounder configuration of FIG. 7 and then with the more bulbous configuration of FIG. 6A. The configuration of first occluding member 102 shown in FIG. 6A is maintained thanks to a connecting member (not shown) that provides for a secure coupling between the proximal and distal ends of first occluding member 102.

Figure 8:
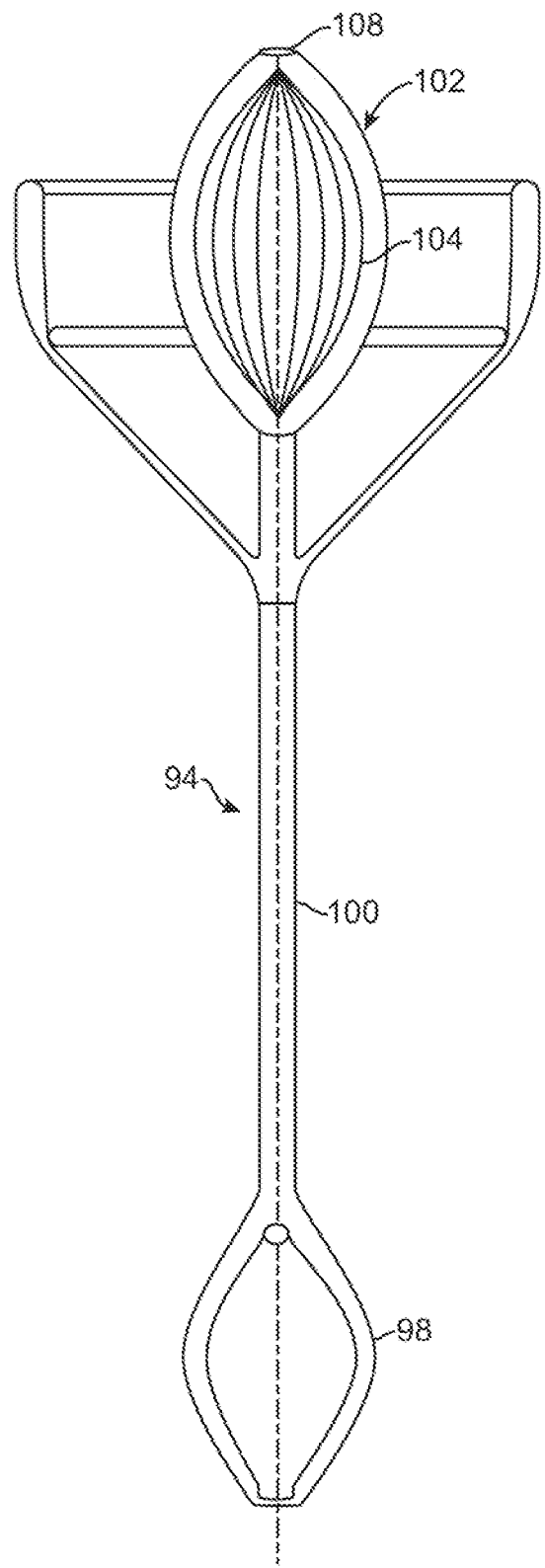
FIG. 8 is a partial cross-sectional side view of the embodiment of FIG. 6A in the elongated, narrower configuration.

Conversely, to revert from the configuration of FIG. 6A to that of FIG. 8, a retainer (such as a string) coupling the connecting member with a release member 108 is severed, in a manner similar to that described in relation to the previous embodiments. In one variant of the present embodiment, string 106 carries a number of spheres 110 or attachments of other shapes that translate through an area having walls where interference is present between such spheres 110 and those walls. Such interference is overcome by the force applied to string 106 when it is pulled, but when such force is not present, the interference is sufficient to block the translation of string 106 and stabilize the configuration of first occluding member 102. In other variants of the present embodiment, spheres 110 on string 106 engage one or more mating locking devices, for example, one or more of mating locking devices 107, 109, or 111 disposed in a longitudinal lumen through device 94 proximally, in the middle, or distally of tether 100.

One skilled in the art will appreciate that struts 104 may be manufactured from a variety of materials, including metallic and plastic materials, for example, silicones and shape memory materials. One skilled in the art will further appreciate that the materials may be impregnated with a therapeutic material that is released in the stomach and/or gastro-intestinal tract over time, and that ancillary components, such feedback and radio transmitters or reservoirs of therapeutic materials, may also be included in device 94, as described with respect to the first embodiment.

Figure 6B:
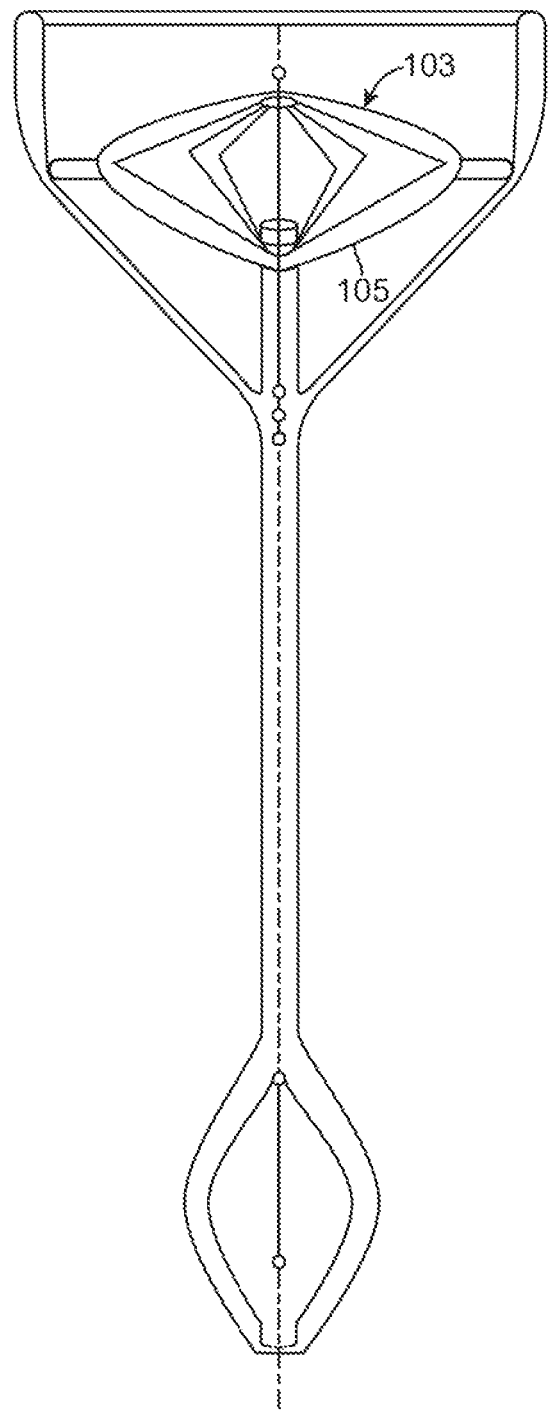
FIG. 6B is a side view of a variant of the embodiment of FIG. 6A.
Figure 7:
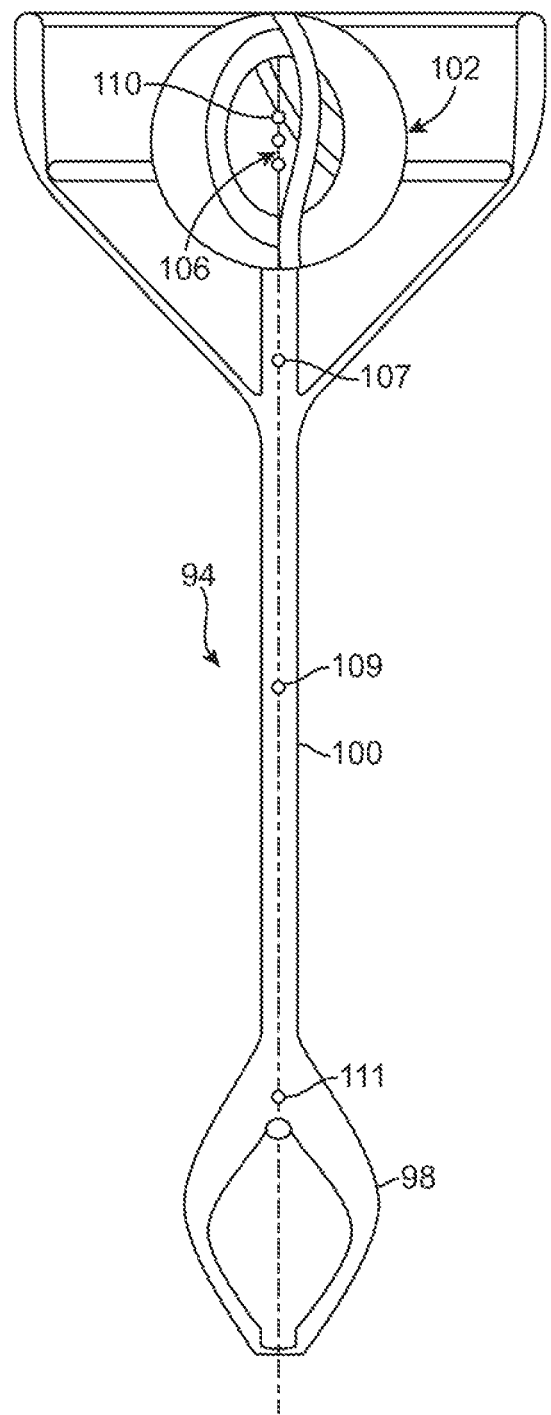
FIG. 7 is a partial cross-sectional side view of the embodiment of FIG. 6A in partially deployed state.

FIG. 6B depicts a variant of the present embodiment, in which first occluding member 103 includes outer surface 105 (in the fashion of a skin) that provides a smoother surface to the gastric mucosa.

Figure 9:
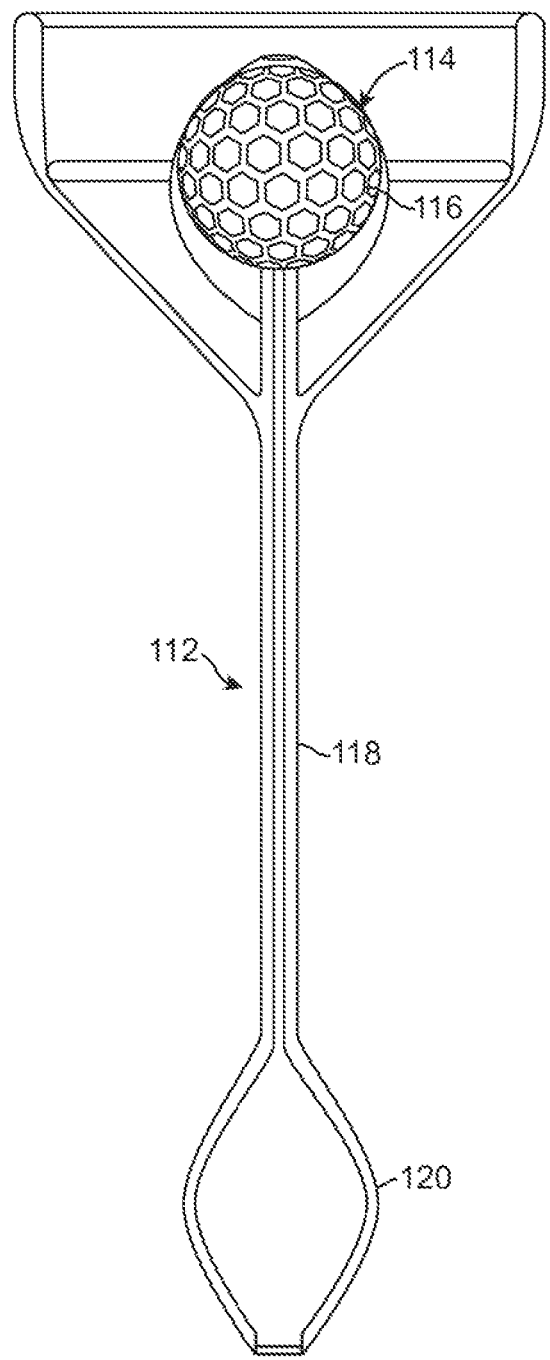
FIG. 9 is a partial cross-sectional side view of a fourth embodiment of the invention.

A fourth embodiment of the invention is illustrated in FIG. 9. A key difference between device 112 of the fourth embodiment and the previously described embodiments is that first occluding member 114 is shaped like a hollow ball having a plurality of openings 116, so that it can be contracted longitudinally, to provide an elongated, narrower configuration suitable for insertion and removal of device 112 into and from the stomach of a patient, or can be expanded laterally by pulling on a string running longitudinally through first occluding member 114, tether 118 and second occluding member 120, so to provide first occluding member 14 with a contracted, wider configuration.

One skilled in the art will appreciate that first occluding member 114 may have a variety of other shapes equally appropriate for the intended purpose, for example, an ellipsoid shape, and that openings 116 also may have a variety of shapes, for example, hexagonal (as shown), polygonal, round or oval.

FIG. 10A depicts a fifth embodiment of the invention. Device 118 is represented only in its proximal portion, which includes apron member 120, first occluding member 122 and the proximal portion of tether 124. First occluding member 122 is illustrated in greater detail in FIG. 10B and has an essentially semispherical outer surface 124, directed proximally (away from the pyloric valve after installation in the stomach) and a plurality of struts 126 that may be shaped as individual rods like the spokes of an umbrella, or as sheets, like the skins of slices within an orange or the blades of a rotary fan. One of the advantages of the present embodiment is the very smooth surface presented by outer surface 124 to the gastric mucosa.

While maintaining the descriptive similarity of first occluding member with an umbrella, it will be noted that first occluding member 124 may be contracted to an elongated, narrower configuration in the fashion of a closed umbrella during insertion of device 118 in the stomach or other organ, and may expanded to an expanded, wider configuration in the fashion of an open umbrella after installation to perform its food blocking function at the pyloric valve. The transition from the elongated, contracted state to the expanded, wider state and vice versa is achieved with the use of a string or equivalent joining product, for example, by having a string 128 extend through one or more loops 130 (or rings or like extensions) on outer surface 124, then with both ends through a lumen (not shown) disposed in the axial direction of first occluding member 122, and then into a lumen within tether 124 that continues within a second occluding member, in a manner similar to the previously described embodiments. Also like in the previously described embodiments, the wider, expanded configuration of FIGS. 10A-10B may be retained by providing a connecting member that engages a corresponding cavity after first occluding member 122 has been fully expanded, and the wider, expanded configuration may be reverted to the narrower, elongated configuration by severing the connection between the connecting member and a release member coupled to the connecting member.

One skilled in the art will appreciate that various features may be added to the present embodiment to improve usability, for example, the entry point of string 128 into outer surface 124 may be funnel shaped. Other features may also be added like in the previous embodiments, for example, feedback and data transmission devices, or reservoirs for therapeutic or selectively irritating substances. Further, device 118 may be manufactured from a variety of materials including a resilient plastic with localized reinforcements, or with a plastic or metal material admixed or coated with a therapeutic substance that elutes over time.

FIGS. 11A-11B illustrate a sixth embodiment of the invention that bears a number of similarities to the previous embodiment but also a few differences, some of which are described hereinafter. Referring first to FIG. 11A, device 132 (illustrated only in its proximal portion) includes a first occluding member 134 that includes (see FIG. 11B) a central hub 136 having a longitudinal lumen 154 therein, one or more struts 138, and optionally, a connecting member 140 extending distally from hub 136.

First occluding member 134 may or may not include an outer surface 142, directed distally (towards the pyloric valve) with its cusp and proximally (towards the esophagus) with its open edge. As in the previous embodiment, struts 138 extend radially from hub 136 and may be shaped like rods, in the fashion of wheels spokes, or like sheets, in the fashion of fan blades.

Outer surface 142 (or hub 136 when outer surface 142 is not present) is connected to the inner tip of the conical portion of apron member 144 by tubular member 146 that, in one embodiment, is essentially cylindrical and has a lumen running longitudinally along its length.

Connecting member 140 includes a rod portion 150 and a conical portion 152, and secures first occluding member 134 in place by extending connecting member 140 into the lumen of tubular member 146, which has a diameter narrower than the diameter of the base of conical portion 152. Therefore, conical portion 152 travels along the lumen of tubular member 146, eventually exiting it when pulled, for example by a string that is disposed around and outside device 132, and then through the lumen 154 of hub 136, then through the lumen of tubular member 146, and then through the lumen of tether 148. The pulling action on the string causes first occluding member 134 to expand from an elongated, narrower configuration suitable for introduction in the stomach through the esophagus to a wider expanded configuration suitable for maintaining apron member 144 in an expanded position.

Because conical portion 152 has a diameter narrower than the lumen of tubular member 146, conical portion 152 is prevented from traveling backwards through the lumen of tubular member 146 once it has exited that lumen, locking first occluding member 134 in a wider, expanded position. At the same time, in a manner like in the preceding embodiment, first occluding member 134 may be reverted from the wider, expanded configuration to the narrower, elongated configuration by severing a link, for example a string that couples connecting member 140 to a release member (not shown), thereby unlocking first occluding member 134. Also like in the preceding embodiments, different types of biocompatible and gastric-resistant materials may be employed to manufacture device 132, and different optional accessories, such as feedback and data controllers and substance reservoirs, may be included into device 132.

One of the advantages of the present embodiment lies in the structure of first occluding member 134, which enables an easy changeover from the elongated configuration to the expanded configurations and vice versa, and in the distal orientation of the cusp of outer surface 142 (when included), or in the shape and disposition of first occluding member 134 within apron member 144, which increases the occluding strength of device 132 against the pyloric valve.

Figure 12A:
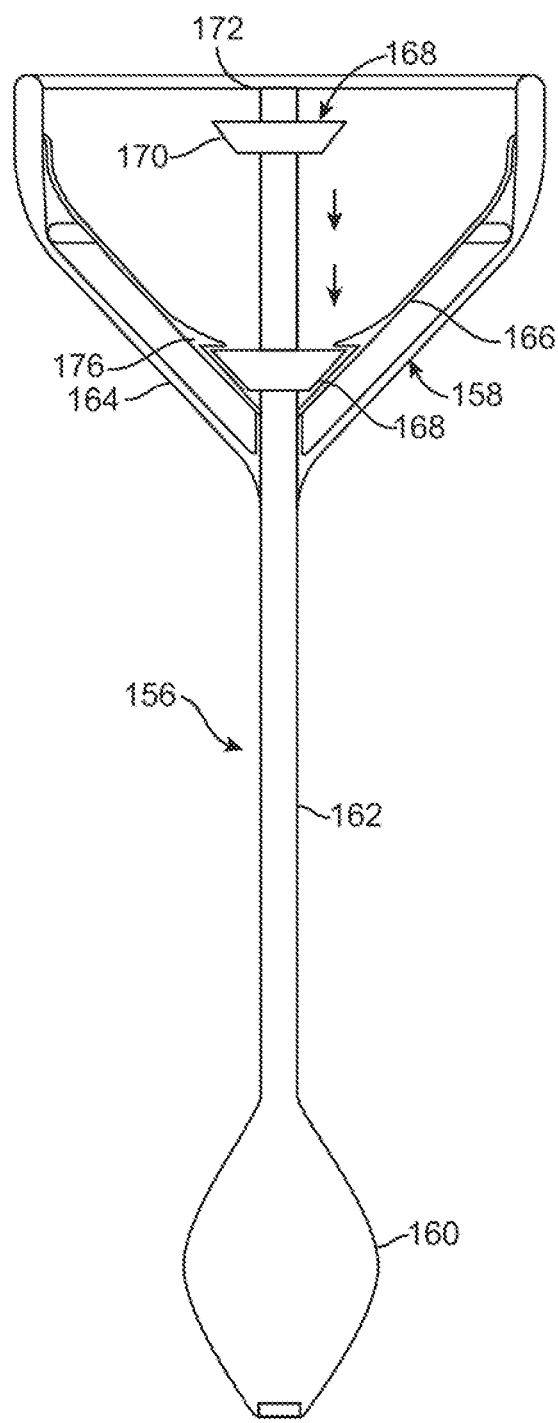
FIGS. 12A-12B are cross-sectional side views of a seventh embodiment of the invention, in a deployed state (FIG. 12A) and in a partially deployed state (FIG. 12B).
Figure 12B:
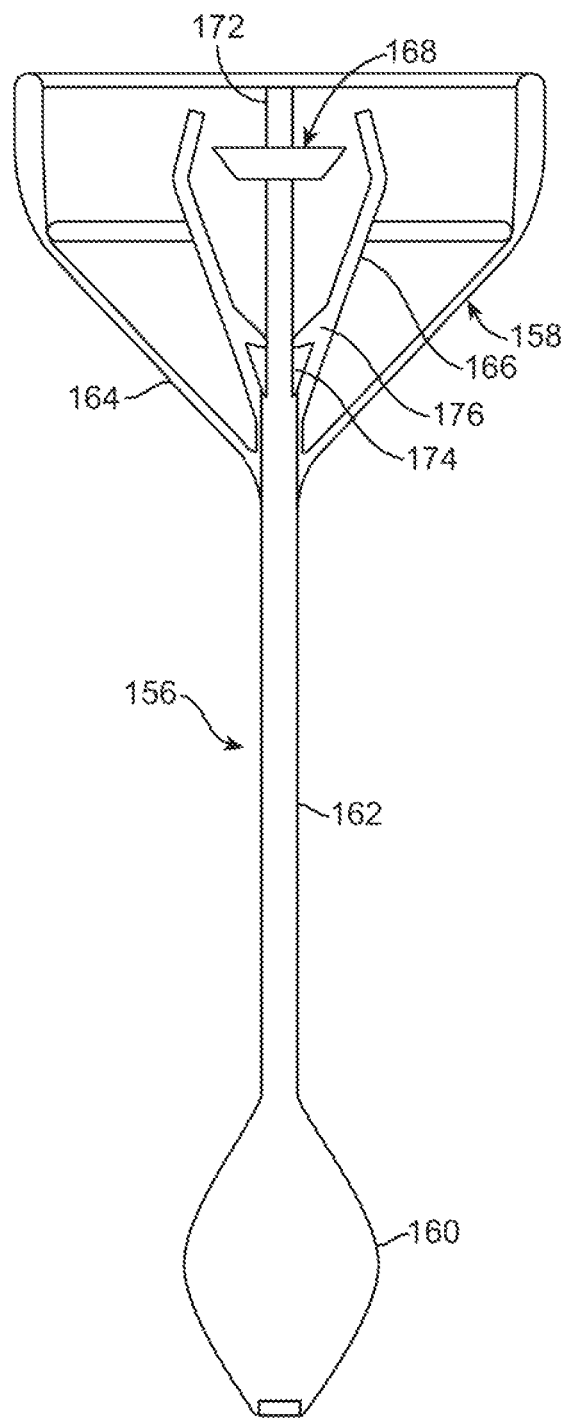

FIGS. 12A and 12B depict a seventh embodiment of the invention, in which a device 156 again includes a proximal member 158 connected to a distal member 160 by a tether 162. In turn, proximal member 158 includes an apron member 164 that surrounds struts 166, which may be shaped as spokes (in the fashion of umbrella spokes) or have a more extended, arched perimeter like longitudinal slices of a cone that encompasses at least a portion of the inner perimeter of apron member 164. More particularly, FIG. 12A shows device 156 with struts 166 in an open position, engaged by a base 168 (shown in FIG. 12A in two positions, one as it approaches struts 166 and the other as it has contacted and engaged struts 166), which has a wider portion 170 and an elongated portion 172. Base 168 has an axial lumen, extending at least through the wider portion 170, dimensioned to engage rod 174 (FIG. 12B) that extends proximally from the distal end of apron member 164, at its conical tip, into the interior of proximal member 158. As base 168 travels towards the interior of proximal member 158, in the direction of rod 174 (FIG. 12B), struts 166 are forced to diverge and provide lateral support to apron member 164, thereby causing proximal member 158 to transition from an elongated, narrower configuration suitable for introduction into the stomach from the esophagus or into another organ, to a wider, expanded configuration suitable for occluding the pyloric valve. Base 168 is retained in a position mated with rod 174 by becoming restrained by retainers 176, suitably angled to promote the movement of base 168 towards rod 174, and to restrain the translation of base 168 in the opposite direction.

Like in the previous embodiments, proximal member 158 may transition from the narrower, elongated configuration to the wider, expanded configuration by pulling on an end of a string (not shown), which travels outside and along device 156 and into the lumens of base 168, rod 174, tether 162 and distal member 160. Base 168 may also include, in its interior portion, a connecting member that engages a mating cavity (for example, by interference fit) to rod 174, or by other engagements known to a person skilled in the art.

Conversely, base member 168 may be disengaged from struts 166 by prying struts 166 open and by releasing base 168 from retainers 176. If base 168 also is retained in place by a connecting member, the disengagement of base 168 to revert device 156 to the elongated, narrower configuration involves the severing of a coupling (for example, a string) between the connecting member and a release member, in a manner similar to that described for the previous embodiments. Also as for the present embodiments, device 156 may be manufactured from a variety of materials that are biocompatible, resistant to the gastric environment and that do not cause erosions of the pyloric wall. Device 156 also may include feedback or data transmission devices or reservoirs of therapeutic or predetermined irritating substances.

Figure 13A:
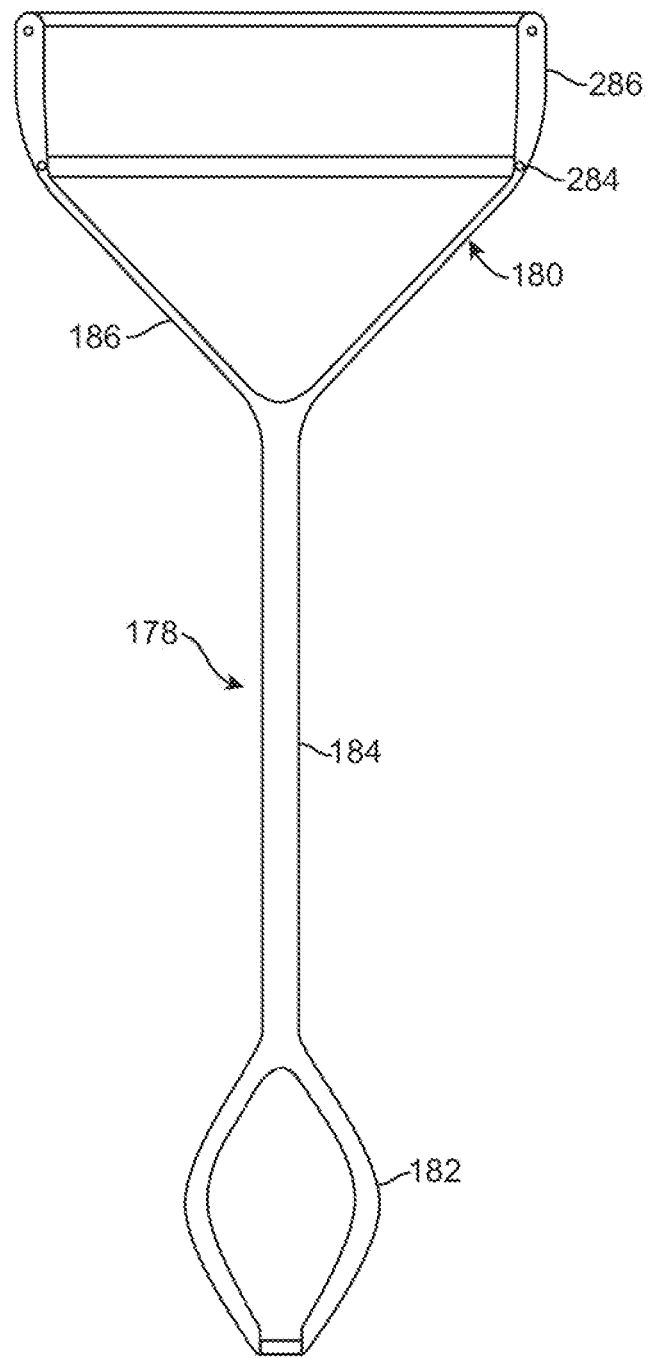
FIGS. 13A-13B are partial cross-sectional side views of an eighth embodiment of the invention.
Figure 13B:
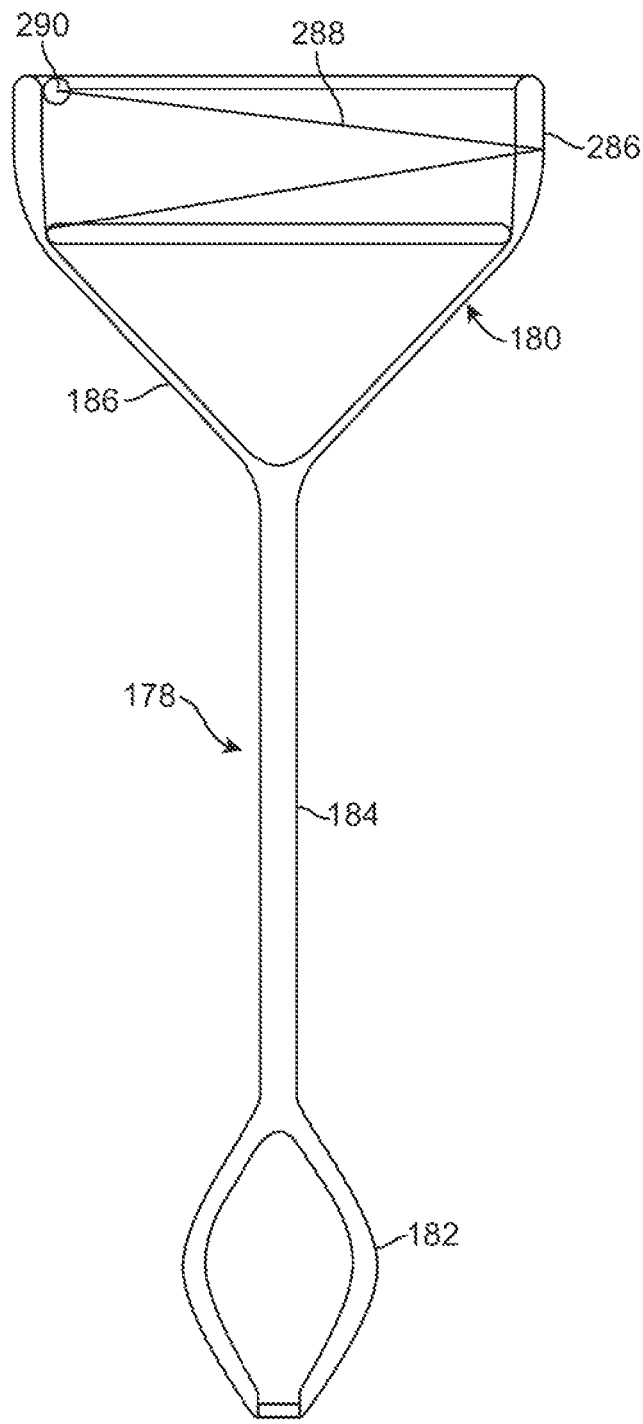

FIGS. 13A-13B depict an eighth embodiment of the invention. Device 178 includes a proximal member 180 and a distal member 182, connected by a tether 184, as in the previously described embodiments, but does not include a first occluding member within apron member 186, contrary to the previously described embodiments. Instead, apron member 186 includes a coil 284 embedded within its wall 286. Coil 284 may have a variety of configurations, for example helical, or be formed by a plurality of parallel circles connected by transversal members so that when one or more of the parallel circles is pulled on, the transverse members cause the circles to become separated one from the other longitudinally and to form a cage-like structure. The helical configuration instead may be delivered coiled on itself to provide for a narrower diameter, giving apron member 186 a narrow, elongated configuration, which may be released after introduction in the stomach to give apron member 186 a wider, expanded configuration.

Removal of device 178 from the stomach, or from another organ in which it may be disposed, requires that device 178 be collapsed to assume an elongated, narrower configuration again. Because reverting coil 284 to the configuration with a narrower diameter may be a rather complex operation if performed through the esophagus when coil 284 is provided with the helical configuration, device 178 includes a tear line 288, so that, by pulling on one end of coil 284, for example, on ring 290 attached to one end of coil 284, coil 284 rips through tear line 288 and becomes extended, enabling a clinician to remove it in essentially wire form. The remainder of device 178 can then be removed together with coil 284, for example by having the remainder of device 178 remain attached to coil 284 after coil 284 has torn tear line 288, or may be removed separately from coil 284.

Like in the previous embodiments, a variety of materials may be used to manufacture device 178 and a variety of ancillary device may also be provided, which will not be described here again for the sake of brevity. In particular, coil 284 may be manufactured from a plastic material, such as nylon or polypropylene, or from a metallic materials, such as stainless steel or a shape memory material.

Figures 14A, 14B, 14C:
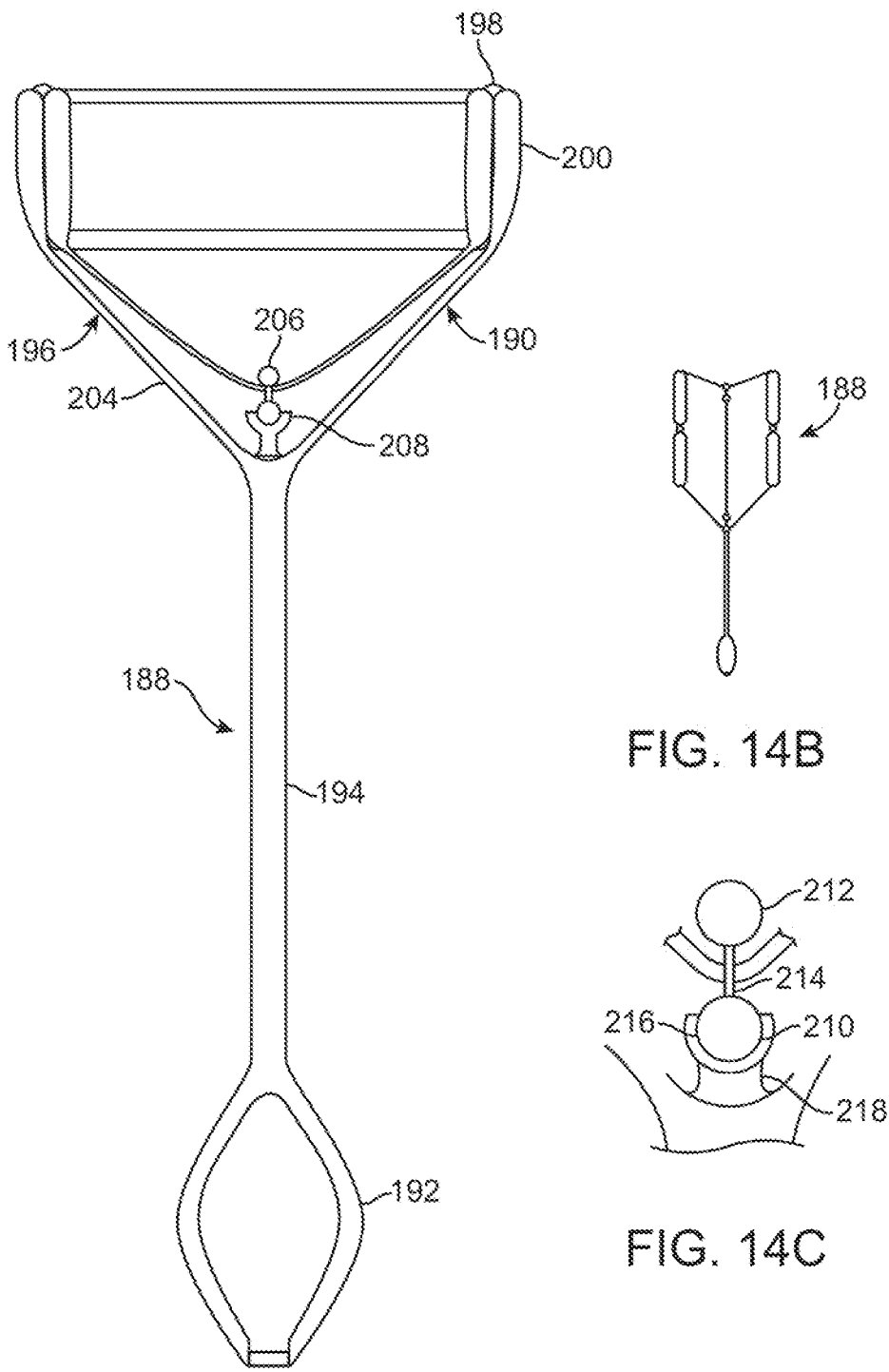

FIGS. 14A-14C and 15A-15D depict a ninth embodiment of the invention. Device 188 includes, like in the previously described embodiments, a proximal member 190 and a distal member 192 connected by a tether 194. In this embodiment, however, apron member 196 is foldable along a crease or living hinge 198 that extends along at least a portion of the circumference of the proximal, essentially cylindrical portion 200. Proximal portion 200 may have a wall of constant section, as shown in FIG. 14A, or of arched cross-section, as shown in FIG. 15A.

During delivery to a target organ, for example, through the esophagus to reach the stomach, proximal portion 200 is extended, as shown in dashed lines in FIG. 15A and in FIG. 14B. A coupling device, such as a string, is connected at one or more points to the free edge of proximal portion 200, for example, at two points 202, and travels toward the inner tip of distal (conical) portion 204 of apron member 196, where it engages connecting member 206, and then extends into lumens disposed within tether 194 and distal member 192.

FIGS. 14A and 14C and FIGS. 15A-15D illustrate different shapes and mechanisms by which connecting member 206 may become locked with mating cavity 208. More particularly, FIG. 14C illustrates connecting member 210 coupled with release member 212 by a connector, such as a string 214. Connecting member 210 is shaped to be engaged in a mating cavity 216, which is situated within support member 218 that is positioned at the internal tip of the distal (conical) portion of apron member 196. As a consequence of the engagement of connecting member 210 with mating cavity 216, apron member 196 becomes locked in place in its configuration with folded, adjacent walls in its proximal (cylindrical) portion 200. Conversely, to extract device 188 from the target organ (for example, to extract device 188 from the stomach through the esophagus), the connector between connecting member 210 and release member 212 is severed, reverting device 188 to its elongated, narrower configuration (shown in FIG. 14B) and facilitating extraction.

FIGS. 15C-15D illustrate variants of connecting member 210. More particularly, FIG. 15B illustrates a variant, in which connecting member 220 includes three annular portions disposed on a rod that become engaged with a correspondingly shaped mating cavity. FIG. 15C illustrates connecting member 222 as having two instead of three annular portions, but a person skilled in the art will appreciate that connecting members can be provided having substantially any number of annular portions. FIG. 15D illustrates connecting member 224 as having a scalloped profile, in which a number of ridges 226 are disposed on a rod member. Mating cavity 228 contains grooves 230 that have shapes matching those of ridges 226. In particular, in one variant of this embodiment, ridges 226 are inclined, so to facilitate insertion into mating cavity 228 but also to hinder removal. Instead, the walls of proximal portion 200 become released and can extend as in FIG. 14B by severing the connection between connecting member 224 and release member 232, for example, by severing string 234 in a manner similar to that of the previous embodiments.

One of the advantages of the present embodiment is that there is no first occluding member, providing for device 188 to have a lower mass than some of the previously described embodiments, and therefore to be lighter and less rigid, irritating the stomach less, and in particular, irritating the pyloric valve less. Like the preceding embodiments, device 188 may be manufactured from a variety of materials and may also be equipped with a number of accessory components for feedback and data transmission and for substance elution. Such materials and accessories will not be described again here for the sake of brevity.

Figures 16A, 16B:
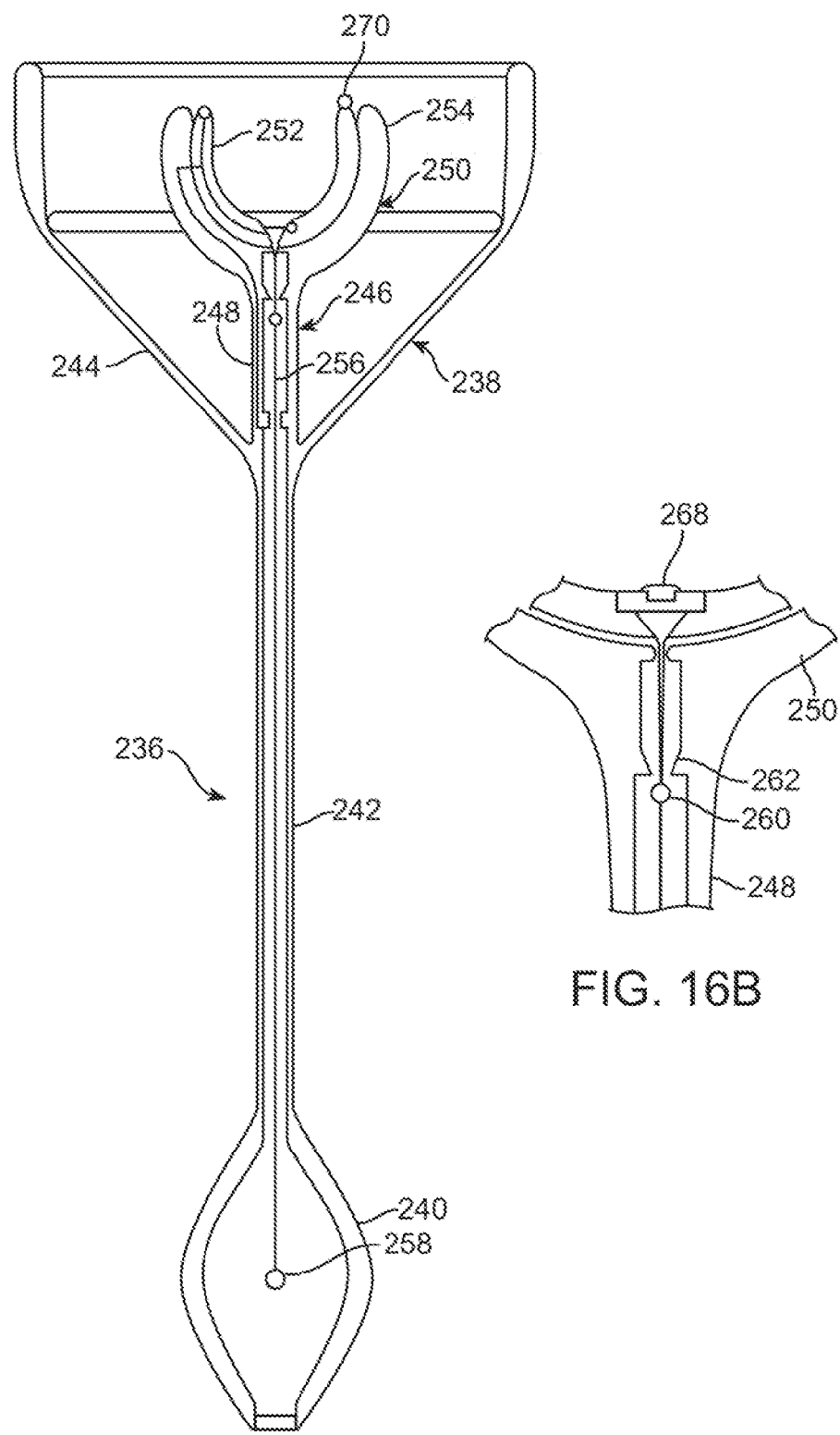
Figure 17:
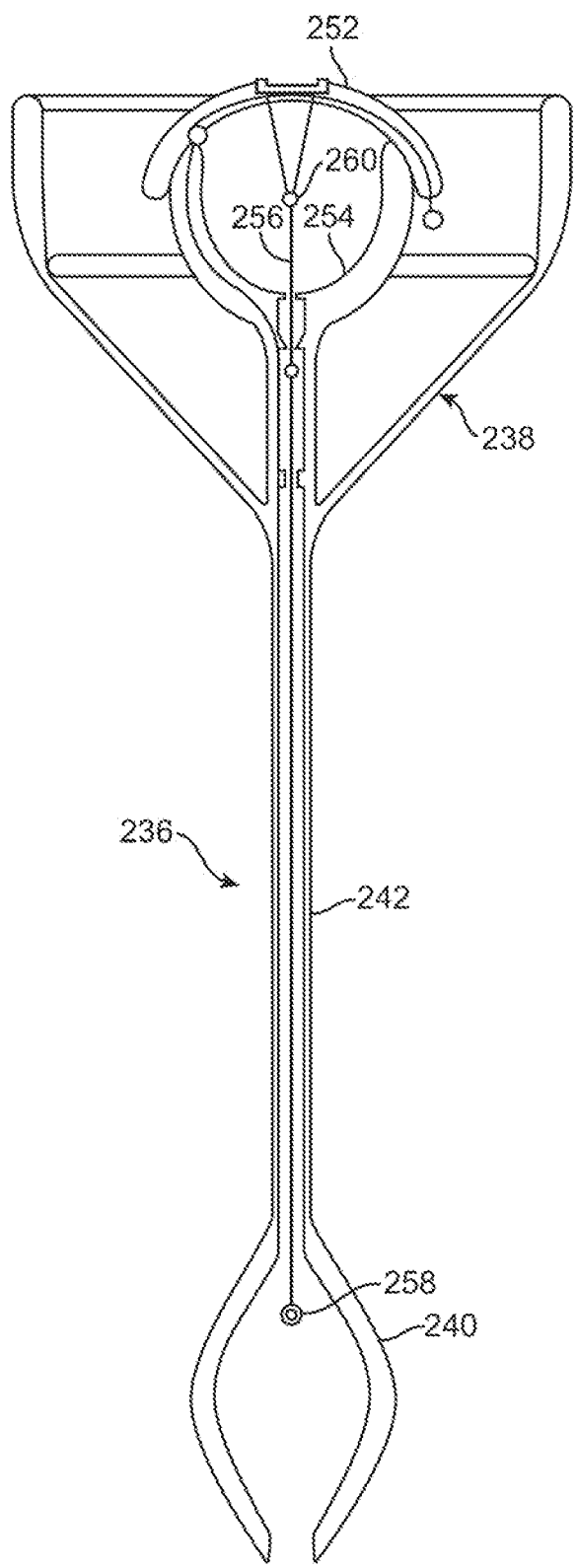
FIG. 17 is a cross-sectional side view of the embodiment of FIG. 16A in the undeployed state.

FIGS. 16A-16B and 17 depict a tenth embodiment of the invention, in which a device 236 includes a proximal member 238 and a distal member 240 connected by a tether 242. Like previously described embodiments, proximal member 238 includes an apron member 244 and a first occluding member 246, which, in the present embodiment, has a shape reminiscent of the letter "Y," in particular, has a stem portion 248 extending from the inner conical tip of apron member 244 (which corresponds to the proximal end of tether 242) to support a curved element 250, typically a semi-circular or semi-elliptical element. More particularly, FIG. 16A shows that curved element 250 has a reinforced, double-layered structure formed by having an outer layer 252 assume the curvature of a base layer 254, as shown in FIG. 17. This "cup within a cup" structure provides for an easy insertion into an organ such as an easy insertion into the stomach from the esophagus while device 236 is in the configuration of FIG. 17, but also provides for a firm, more rigid structure in the configuration of FIG. 16A, due to the layered structure of curved element 250. The changeover from the structure of FIG. 17 to that of FIG. 16 is enabled by providing a string 256, coupled to outer layer 252, to travel through lumens into stem 248, tether 242 and distal member 240. As shown in FIG. 17, string 256 may be coupled with outer layer 252 in two points, but one skilled in the art will appreciate that string 252 may be coupled in one or more points. FIGS. 16B and 17 further show that a recess is carved in outer layer 252 to house a release element, which, like in the previous embodiments, is used to unlock first occluding member 246 prior to removal from the stomach or other organ. Alternatively, string 256 may be connected to one or more loops or rings 270 at the periphery of outer layer 252 and travel through a conduit within outer layer 252, exiting that conduit in the area shown in FIGS. 16A-16B.

Figure 18:
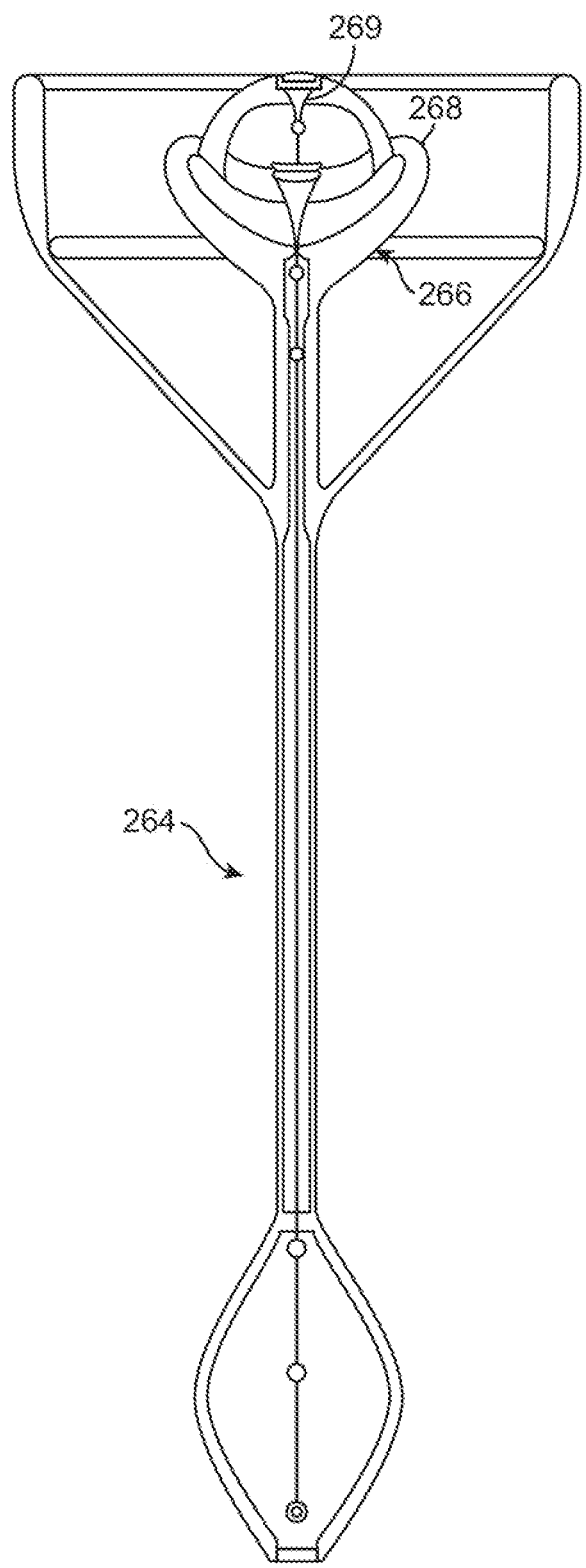
FIG. 18 is a cross-sectional side view if a variant of the embodiment of FIG. 16A.

Outer layer 252 is locked against base layer 254 by pulling on string 256 (for example, by pulling on snare ball 258), and by having protrusions 260 extending from string 256 engage a locking ring 262 disposed in the lumen either of stem 248 (as illustrated in FIGS. 16A and 16B) or of tether 242 (as illustrated in FIG. 18, in relation to a similar embodiment). Protrusions 260 are shown as spherical protrusions in the illustrated embodiment, but one skilled in the art will recognize that other shapes are also possible.

FIG. 18 depicts an eleventh embodiment of the invention, in which device 264 is constructed similarly to device 236, except that first occluding member 266 is not composed of two separate and distinct layers attached to a stem, but instead includes two layers attached to a stem that are formed by having a closed member 268 fold on itself in the manner of a deflating ball. One of the advantages of device 264 over device 236 resides in the smooth edges of first occluding member 266, as opposed to the sharper edges of curved element 250 in device 236. Living hinges or creases that facilitate the folding process may be optionally provided. Locking and unlocking mechanisms are the same as for device 236 and for both devices 236 and 264. A variety of materials and accessory components may be envisioned, in the same manner as for the preceding embodiments.

Embodiments 236 and/or 264 may be selectively reinforced in certain areas. For example, if embodiments 236 and/or 264 were made of a silicone material, a fabric insert may be inserted in the area surrounding release element 269, to decrease the risk of tear in that area.

FIG. 19 depicts a twelfth embodiment of the invention. Device 272 includes a proximal member 274 and a distal member 276, connected one to the other by a tether 278. In turn, proximal member 274 includes an apron member 280, shaped like in the previously described embodiments, and a first occluding member 282 that has a bulbous shape, made of a rolled layer in the fashion of a snail shell as described in U.S. patent application Ser. No. 11/702,888. For introduction into an organ (for example, introduction into the stomach through the esophagus), first occluding member 282 is distended (not rolled up), providing device 272 with a narrower, elongated shape. In the distended, elongated state, first occluding member 282 exhibits a wider, more bulbous base and a narrower, tongue-like extension. As shown in FIGS. 20A-20C, a string extends from the tip or an intermediate point of the tongue-like extension and may travels through an opening in and across the base so that when the string is pulled, the tongue-like extension rolls on itself and causes first occluding member 282 to assume its contracted, wider configuration shown in FIG. 19. A button-like retaining member on the tongue-like extension eventually travels through and engages the opening in the base, locking first occluding member 282 in the contracted configuration. That button-like retaining member may be severed from first occluding member 282, enabling first occluding member 282 to revert to its elongated, narrower shape.

Figures 21A, 21B:
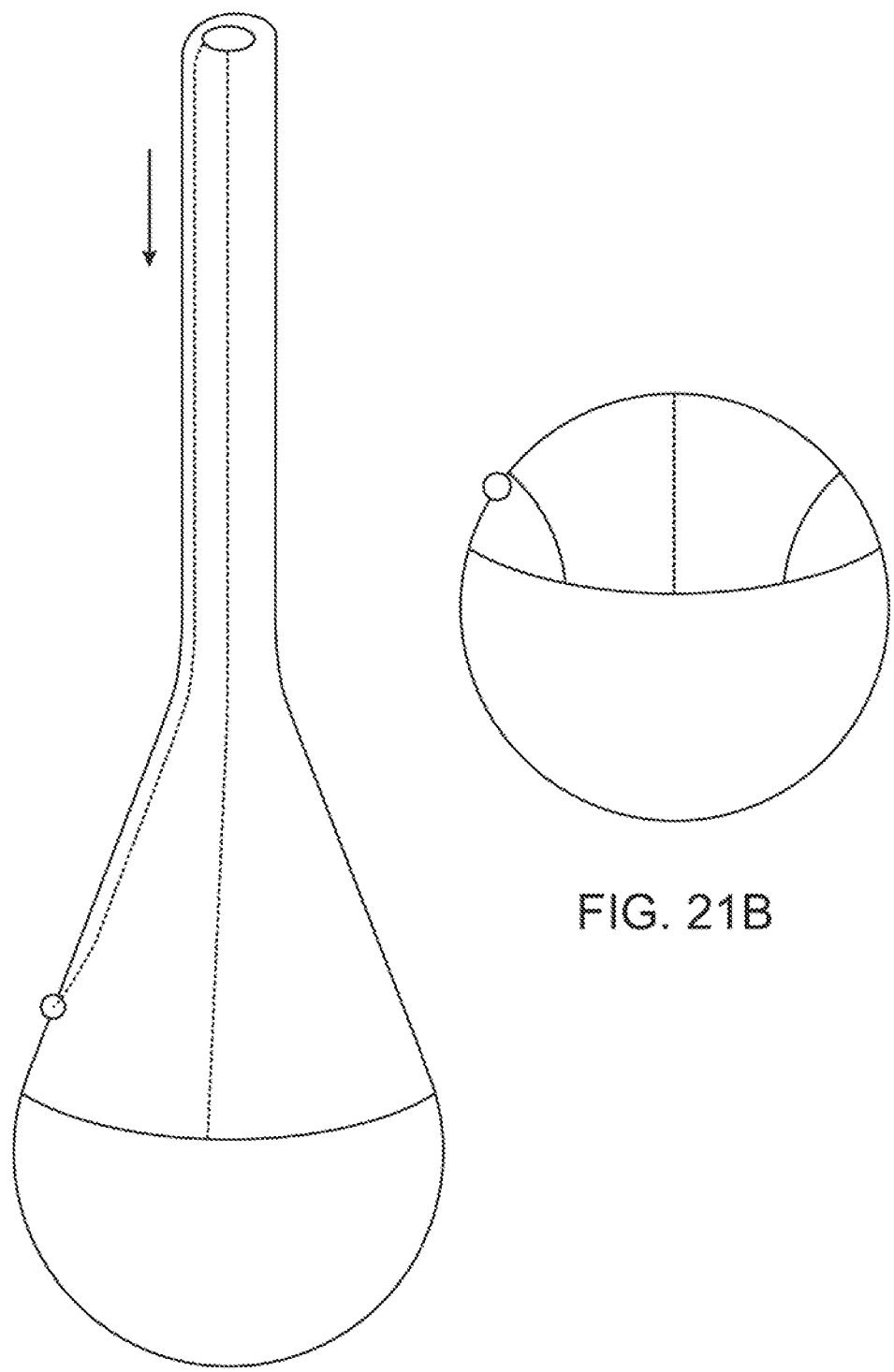
Figures 22A, 22B, 22C:
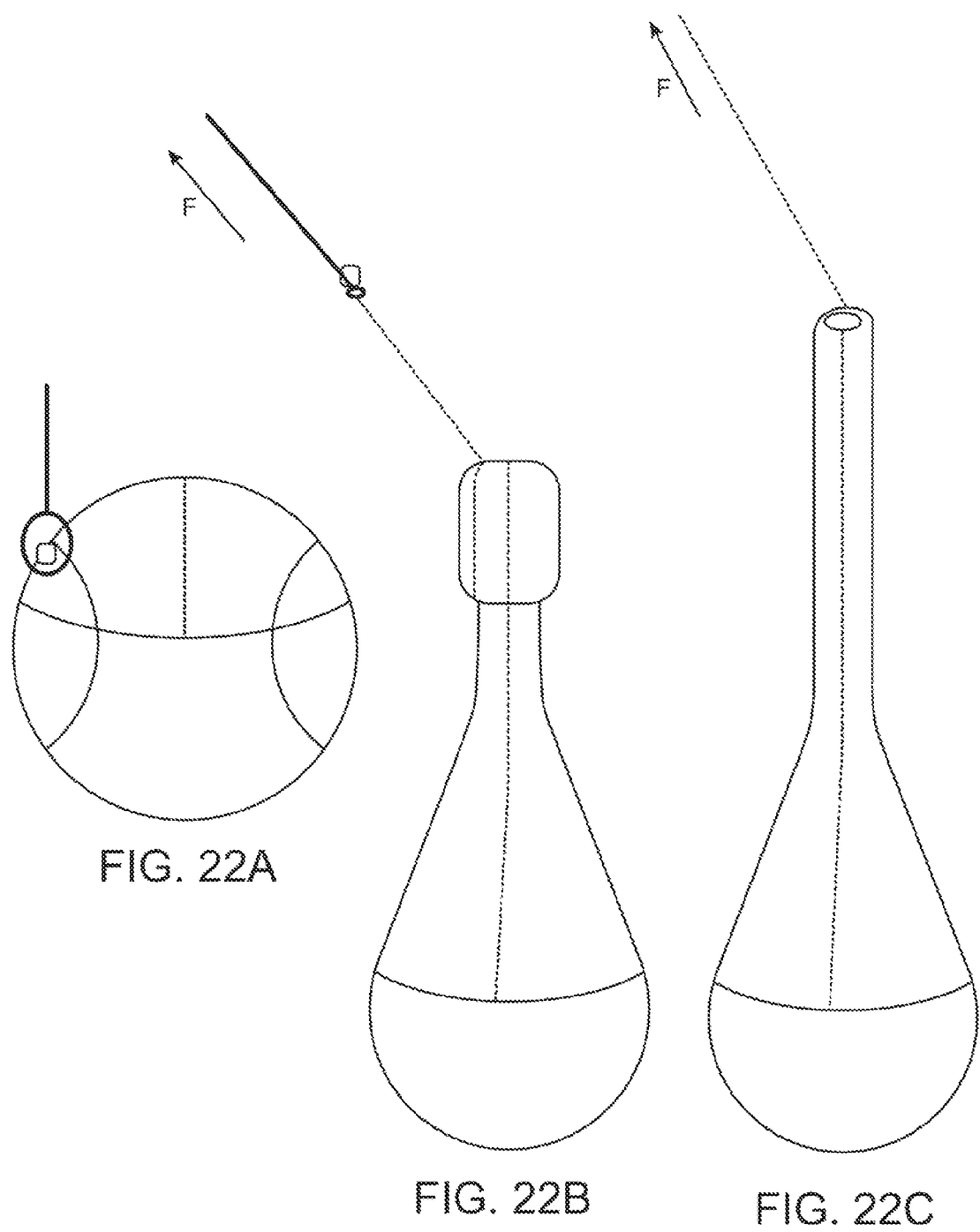

Alternatively, as shown in FIGS. 21A-21B, the string may originate from the base of first occluding member 282 and travel to exit first occluding member 282 at the tip of the tongue-like extension, so that a pulling of the string causes first occluding member 282 to roll on itself and acquire the contracted configuration, eventually securing the string to a release member. In this alternate design, first occluding member 282 may revert to the elongated, narrower configuration either by severing the release member, or by pulling on the release member and by causing the string to cut through a tear line, opening up first occluding member 282, as shown in FIGS. 22A-22C.

The following Example relates to the procedure for implanting and explanting a trans-pyloric device, such as device 30 described above, in the stomach of a dog.

TABLE I

| STEP # | DEVICE IMPLANT PROCEDURE |
|---|---|
| 1 | Anesthetize fasted dog and place on table. |
| 2 | Ensure that the long endoscope will be used (Olympus model CF Type 100 TL or equivalent). |
| 3 | Insert video tape into endoscopy equipment. |
| 4 | Place endoscope through the esophagus, and into the stomach. |
| 5 | Drain stomach contents and inflate the stomach. |
| 6 | Make sure endoscope video is recording throughout the entire procedure. |
| 7 | Perform thorough baseline endoscopic analysis of the stomach, looking for any preexisting erosions or ulcerations paying particular attention to the lower esophageal sphincter, the antral region, and the proximal pylorus. Document findings on device insertion worksheet. |
| 8 | Place the scope through the pyloric cylinder to rule out incompetent and/or patulous pylorus. Inspect the lining of the duodenum and duodenal bulb for evidence of erosion and/or ulceration. Document findings on device insertion worksheet. |
| 9 | Pull endoscope back out of pylorus to the GE junction (scope just entering the stomach). |
| 10 | Record the endoscope depth at the GE junction on the device insertion worksheet. |
| 11 | Mark depth of GE junction on the delivery device with respect to the proximal end of the pod (using colored tape). |
| 12 | Record device ID on the device insertion worksheet. |
| 13 | Lubricate the delivery device along its length with surgical jelly. |
| 14 | Insert delivery device until GE junction mark is reached. This will ensure that the pod is fully within the stomach. If necessary, insert delivery catheter until resistance is felt and remove stiff pod closure rod from half of the delivery pod length. Then advance delivery device until proximal portion of the pod is past the GE junction. |
| 15 | Insert endoscope beside delivery device - obtain image of pod in the stomach. |
| 16 | Remove the stiff pod closure rod to fully release the device from the pod. |
| 17 | Pull the pull-ring until locking indicator is visualized; this will lock the implant. |
| 18 | Cut the red fiber and pull the ring to remove pull cord. |
| 19 | Examine the stomach lining to ensure that no gross tissue damage has been caused by the placement and removal of the device and delivery system. Inspect the stomach body, antrum, and pylorus for evidence of erosion, laceration, or other forms of damage and record observations on the device placement worksheet. |
| 20 | If distal bulb remains in the proximal portion of the delivery pod, utilize the endoscope to manipulate the distal bulb clear of the delivery pod. |
| 20 | Slowly remove the endoscope. |
| 21 | Remove delivery system. |
| 22 | Awaken and recover animal. |

The animal will be then be recovered and housed. Once the veterinarian determines that the animal's recovery is complete, the animal will be moved to a housing facility in an individual run. Water will be available ad libitum. Animal feed, per scheduled feeding, may include prophylactic antibiotics to protect against respiratory infection.

TABLE II

| STEP # | DEVICE EXPLANT PROCEDURE |
|---|---|
| 1 | Anesthetize fasted dog and place on table. |
| 2 | Ensure that the long endoscope will be used (Olympus model CF Type 100 TL or equivalent). |
| 3 | Insert video tape into Fluoroscopy Equipment. |
| 4 | Insert video tape into endoscopy Equipment. |
| 5 | Place endoscope through the esophagus and into stomach. |
| 6 | Make sure endoscope video is recording. |
| 7 | Record position of device (transpyloric, fully intragastric or not visible from gastric space, on the device removal worksheet. |
| 8 | Perform thorough endoscopic analysis of gastric space looking for erosions or ulcerations paying particular attention to the lower esophageal sphincter, the proximal pylorus and the antral region of the stomach. |
| 9 | If device was not visible from gastric space in 7, enter duodenum and search for implant, if found, return to line 10, if not found, perform fluoroscopy to locate implant and go to line 22. |
| 10 | Cut the string at the top of the TPS to release the locking mechanism. Insert loop snare (240 mm) into working channel of endoscope and snare device retrieval ball. |
| 11 | Using the snare, position the retrieval ball 3-4 cm away from the distal end of the endoscope. |
| 12 | Maintain firm grip around retrieval ball with the snare. |
| 13 | Remove endoscope while maintaining the position of the snare with respect to the endoscope, such that the implant follows the endoscope out through the esophagus. As the implant is retrieved, the esophageal orifice will cause the unlocked spiral to unfurl. The shell will collapse at the lower esophageal sphincter and the entire device will be removed along with the endoscope. |

TABLE II-continued

| STEP # | DEVICE EXPLANT PROCEDURE |
|---|---|
| 14 | If device remains in animal, repeat steps 10-13. |
| 15 | Rinse the implant with water to remove any remaining stomach contents. Label the device with the animal ID number and date and time of removal, and place in Ziplock bag for analysis. Note any issues with device removal or any observations made during the removal procedure on the Device removal worksheet. |
| 16 | Place the endoscope back through the esophagus into the stomach. |
| 17 | Advance endoscope across pylorus into the duodenum. |
| 18 | Perform thorough endoscopic analysis of proximal 10 cm of duodenum looking for erosions or ulcerations paying particular attention to the distal pylorus and the duodenal bulb. |
| 19 | Remove endoscope and continue. |
| 20 | Wake animal and return to cage. |

An endoscopic evaluation procedure of the implanted device is described next.

After standard fast, with water provided ad libitum, the dog will be brought into a purpose-built operating room, which will include an operating table and anesthetic machine with $CO_2$, respiratory, a pulse rate monitor, and a ventilator. Anesthesia will be titrated to maintain the dog at the appropriate level of anesthesia for an endoscopic procedure as determined by the veterinarian. All animals studied will be monitored for end-tidal volume $CO_2$, respiratory rate, and pulse rate throughout the anesthetic procedure. After induction, the dogs will be intubated endotracheally and endoscopy will be performed.

Cursory endoscopic evaluation will be performed on animals in Control Group 4 in order to ensure similar treatment as animals in Groups 1, 2, 3 and 5. Thorough endoscopic evaluation will be completed on all animals in Groups 1, 2, 3 and 5 until they are terminated from the study according to the following protocol:

TABLE III

| STEP # | ENDOSCOPIC EVALUATION PROCEDURE |
|---|---|
| 1 | Anesthetize fasted dog and place on table. |
| 2 | Ensure that the long endoscope will be used (Olympus model CF Type 100 TL or equivalent). |
| 3 | Insert video tape into endoscopy equipment. |
| 4 | Place endoscope through the esophagus, and into the stomach. |
| 5 | Drain stomach contents and inflate the stomach. |
| 6 | Make sure endoscope video is recording throughout the entire procedure. |
| 7 | Perform thorough endoscopic analysis of the stomach, looking for any erosions, ulcerations, fibrosis, stenosis, scarring, webbing or atresia, paying particular attention to the lower esophageal sphincter, the antral region, the gastric and duodenal pyloric regions and the duodenal bulb. Document findings on endoscopic evaluation worksheet. |
| 8 | In the event of ulceration, assign the ulceration a grade and biopsy, if required. Document findings on endoscopic evaluation worksheet. |
| 9 | If a device is present, document its orientation and position on the endoscopic evaluation worksheet. |
| 10 | If a device is present, perform thorough analysis of the device including assessment of: 1) the integrity of the shell, tether, central spiral and, if visible, distal bulb, 2) the state of the snare ball including absence or presence of tension in locking cord and any protrusion of the snare ball out of the central depression. Document findings on endoscopic evaluation worksheet. |
| 11 | If a device is present, record the presence and location of any foreign materials within the device (such as trapped fibers) and any notable discoloration. Document findings on endoscopic evaluation worksheet. |
| 12 | Slowly remove the endoscope. |
| 13 | Awaken and recover animal. |

The animals will then be recovered and housed. Once the veterinarian determines that the animal's recovery is complete, animals will be moved to a housing facility in an individual run. Water will be available ad libitum. Animal feed, per scheduled feeding, may include prophylactic antibiotics to protect against respiratory infection or proton pump inhibitors to treat diagnosed ulceration.

FIGS. 23A-23C, 24A-24C, 25A-25C, 26A-26C, 27A-27C, and 28A-28D illustrate methods of implanting a device in the stomach or other organ based on inflating the device or otherwise having the device increase in size in the stomach from a smaller volume during insertion. These figures should be understood to have a generic illustrative purpose only, and that the specific shapes of the devices as disposed in the gastrointestinal tract are to be selected among those described in the previous embodiments.

More particularly, FIGS. 23A-23C illustrate a device introduced in the stomach or other part of the gastrointestinal tract in an elongated configuration (FIG. 23A), which is expanded to an intermediate (FIG. 23B) and eventually a final configuration (FIG. 23C) by injecting a foam with an appropriate catheter, causing a volume expansion.

FIGS. 24A-24C illustrate a process similar to that of FIGS. 23A-23C, except that a substance such as water, a reagent and/or a catalyst, is injected through the catheter, which upon contact with a product already present in the device causes a volume expansion of that product.

FIGS. 25A-25C illustrate schematically a mode of placement of the devices of FIGS. 23A-23C and 24A-24C through a catheter introduced through the esophagus (FIG. 25A), then used for infusing foam or a growth substance (FIG. 25B), causing the device to become fully inserted (FIG. 25C). Conversely, FIGS. 26A-26D illustrate the removal of that device by showing the device in its placed state (FIG. 26A), the attachment of a device extractor (FIG. 26B), the activation of predetermined failure points (FIG. 26C), and the extraction of the device (FIG. 26D).

FIGS. 27A-27C illustrate other embodiments, in which multiple distal bulbs (FIG. 27A) or a larger distal bulb (FIG. 27B) may be present to slow transit of food in the gastrointestinal tract, or in which no distal bulb may be present and the device can act as a space filler (FIG. 27C).

In particular, FIG. 27C illustrates device 293, which is configured as an occluding member that resides in a stomach 295. Device 293 has no tether and no second occluding member and in that respect, device 293 show a variant possible for all embodiments of the invention, namely, that while the embodiments described hereinbefore and hereinafter have been illustrated as including a proximal member, a distal member and a tether, the distal member and/or the tether may be not be included in variants of those embodiments. For example, a variant of embodiment 30 may include only proximal member 32, or proximal member 32 and distal member 34 connected one to the other without tether 36, or with a tether 36 of different lengths and configurations. For example, tether 36 may connect multiple distal members as in the structure of device 291 in FIG. 27A.

Additionally, device 293 may include one or more elements structured to alert the patient or a clinician or other attending personnel of a failure of the device, whether such failure is real or potential. For example, a signal may be transmitted that alerts the patient or other attending personnel of the breach of wall 297 of device 293, making device 293 at risk of migrating from stomach 295 and of passing into duodenum 299, both losing its functionality in the stomach and negatively affecting the functionality of the intestinal tract, typically ending up expelled from the patient's body as feces. Such a signal may be provided by the activation of an eccentric motor or of a mechanical, electric or electronic alarm system associated with the integrity of wall 297. For example, changes in pressure, mechanical shape, conductivity, capacitance, resistance, pH, or optical properties of a fluid contained in device 293, or the activation of electric or electronic monitoring systems associated thereto, may trigger such a signal.

In one variant of the present embodiment, device 293 includes a patch 301 designed to plug an inflation opening in the outer shell or wall 297 of device 293. More particularly, patch 301 defines a discrete region of increased hardness and/or thickness, through which device 293 may be inflated or filled. In this variant, an alert system 303 may interact with shell 297 of device 293 in any region of shell 297 or only with patch 301. Alert systems of this kind are disclosed in PCT patent application WO 2006/135857, which are incorporated herein by reference.

In its simplest variant, device 293 is filled with a non-conductive aqueous medium (for example, with polyethylene glycol or with another non-conductive, osmotic hydrophilic material dissolved in de-ionized water), and alerting system 303 simply monitors the conductivity or other electrical properties of the fluid, which will change dramatically when a breach occurs in shell 297 of device 293. Alternatively, device 293 may incorporate two electrodes on patch 303, one of which faces externally and the other one internally, such that a voltage applied to one electrode is only sensed by the other electrode if there is a breach in shell 297, which is built of a highly insulating material such as silicone. In this variant, device 293 may include a battery with longevity greater than implant duration, as well as an alerting system 303 (such as an eccentric motor, a radiofrequency alert system, or an acoustic generator) to alert the patient or attending personnel that a breach has occurred.

FIGS. 28A-28C further illustrate the mode of use of a gastric filling device designed to increase in volume in the stomach. In particular, FIG. 28A shows insertion of the device, FIG. 28B shows inflation of the bulbs, and FIG. 28C shows the intestinal migration of the distal bulb. FIG. 28D instead shows that obesity treatments may be enhanced by adding gastric fillers in the stomach.

FIGS. 29A-29C illustrate a thirteenth embodiment of the invention, in which device 292 includes a proximal member 294 that is connected to a distal member by a tether (both not shown) in the same manner as in the previously described embodiments. In turn, proximal member 294 is composed of an apron member 296 that surrounds a first occluding member 298, disposed in an essentially central position within apron member 296.

First occluding member 298 is structured to be formed from an elongated, single layer configuration used during the insertion process into the stomach or other organ of a patient to a telescoping, multi-layered configuration after implantation in the stomach or other organ is achieved. More particularly, first occluding member 298 includes a distal part 300, a central part 302, and a proximal part 304, which, in variants of this embodiment, may be divided one from the other by living hinges 306, or by creases, or by slots, or by localized thinnings of the wall of first occluding member 298, or may just be folded one onto the other when pressure is applied on proximal part 304.

Proximal part 304 includes a proximal protrusion 308, extending in a direction opposite to the tether, a distal protrusion 310, extending in the direction of the tether and shaped to interference fit within mating cavity 312, and a body 314, supporting proximal protrusion 308 and distal protrusion 310 at opposite ends. The interference fit between distal protrusion 310 and mating cavity 312 causes first occluding member 298 to maintain its contracted shape after the telescopic folding of proximal part 304, central part 302 and distal part 300 one onto the other. This may be achieved by compressing proximal protrusion 308 distally, for example with a catheter inserted into the stomach and pushing in the direction of the tether, or by having a connector (such as a string) run through mating cavity 312 and through a lumen in the tether and in the distal member, to enable a clinician to pull distal protrusion 310 into mating cavity 312. In a variant of the present embodiment, as well as in variants of the previously described embodiments, the string may exist device 292 not through the distal member, but from an opening situated in the tether in device 292.

When it is desired to remove device 292 from the stomach or other organ, first occluding member 298 can be unfolded to regain its elongated, narrower configuration in different ways. In one variant of the present embodiment, first occluding member 298 can be unfolded by simply pulling on proximal protrusion 308, thereby overcoming the interference fit between distal protrusion 310 and mating cavity 312. In another variant of the present embodiment, proximal protrusion 308 and distal protrusion 310 are coupled one to the other by a connector, such as a string, so that when that connector is severed (for example, by cutting the string), proximal protrusion 308 and distal protrusion 310 become uncoupled, with distal protrusion 310 remaining contained within mating cavity 312 while proximal protrusion 308 extends outwardly.

FIG. 29B illustrates the same embodiment of the invention as shown in FIG. 29A, except that distal protrusion 316 and mating cavity 318 do not have cylindrical shapes, or, more general, the shapes of a parallelepiped, as in FIG. 29A, but instead have more expanded shapes, for example, have the shape of a sphere supported by a cylinder illustrated in FIG. 29B, thereby providing for a tighter interference fit than in the embodiment shown in FIG. 29A. One skilled in the art will appreciate that distal protrusion 316 and mating cavity 318 may be shaped in a variety of other shapes as well, all which fall within the shape and scope of the present invention.

FIG. 29C further illustrates the similar embodiment of the invention as shown in FIG. 29B, except that no proximal or distal protrusions are present. More particularly, FIG. 29C illustrates the transformation of proximal member 320 from the elongated, narrower configuration shown on the left hand side to the wider, contracted configuration shown on the right hand side, and also shows how such transformation may be attained by pulling on a string 322, which may be connected in one or more points to the proximal end 324 of proximal member 320. In its low-profile delivery configuration, occluding member 342 may be attached via circular wall sections which may evert or fold upon themselves to form the deployment configuration shown. In this particular example, first wall section 330 (having an average thickness of, e.g., 2 mm) may extend at an angle to first interlockable wall section 334 (having an average thickness ranging from, e.g., 1 to 3 mm). A second interlockable wall section 338 (also having an average thickness ranging from, e.g., 1 to 3 mm) may extend from first interlockable wall section 334 with a complementary wall section 332 (having an average thickness of, e.g., 2 mm) with occluding member 342 attached thereto.

When reconfigured for deployment, occluding member 342 may be urged via string 322 towards its distal end such that second interlockable wall sections 338 may rotate and evert about hinged region 326, e.g., living hinge, such that first wall surface 336 and second wall surface 340 come into apposition relative to one another and complementary wall section 332 pivots about hinged region 328 to come into contact against first wall section 330.

The apposed first and second interlockable wall surfaces 334, 338 may be configured along their interface 344 to temporarily or permanently adhere to one another, e.g., via an adhesive, as illustrated in the cross-sectional end view of FIG. 30A. Alternatively, each of the respective surfaces may define surface features, e.g., interlocking ridges 346, which interdigitates relative to one another to prevent or inhibit the unfolding or unlocking of the device back into its low-profile configuration, as illustrated in the cross-sectional end view of FIG. 30B.

A device constructed according to the principles of the present invention (as described through a number of representative embodiments) is suited not only for the treatment of obesity, but also for treating other ailments. Examples of such treatments include treatments to restore normal glucose tolerance to a diabetic or prediabetic subject, or to delay or prevent the progression of diabetes in a subject by inhibiting fasting insulin secretion or glucose-stimulated insulin secretion. Other examples of such treatments include the treatments of patients suffering from one or more diseases characterized by obesity, including hyperphagia, dyslipidemia, Prader Willi syndrome, Froelich's syndrome, Cohen syndrome, Summit syndrome, Alstrom syndrome, Borjesen syndrome, Bardet-Biedl syndrome, or hyperlipoproteinemia, types I, II, III, and IV.

While an example of use of the present invention for the treatment of different ailments has been described with reference to the first embodiment (device 30), the other embodiments described herein are equally suitable for the treatment of those types of diseases.

Also as previously mentioned, a number of ancillary components may be included in a device constructed according to the principles of the present invention, for example sensors or transmitters that provide feedback and other data to an intra-corporeal or extra-corporeal processor. The device of the present invention may also be structured to release a therapeutic substance to treat predetermined conditions, or a mildly irritating substance that is released when an undesirable substance (for example, sugar) is detected in the stomach or in the organ where the device is disposed. Such a substance may be contained in a reservoir and be dispersed in the gastro-intestinal tract either over time, or upon opening of the reservoir by a sensor. Alternatively, such a substance may be coated on the device, or may be impregnated on the surfaces of the device or within pores on the device, admixed with the constituent materials of the device, for example with a resin, to be released over time upon contact with gastric substances.

This embodiment, as well as any other embodiment discussed herein, may be functional in the fully gastric or in the transpyloric position, and may or may not include an element designed to span the pylorus. Accordingly, any of the aforementioned functions of this or any other embodiments may be accomplished with a shape-memory, locking or inflatable structure that is designed to reside fully and solely within the gastric space.

In addition, when any of the embodiments described herein has a locking capability (for example, by using a string to engage a connecting member with a mating cavity, and/or by using a string to connect the connecting member to a release member such that a severing of the string causes the device to lose its locked, bulbous configuration), an alerting element may be employed to detect a reduction in tension of the locking string and to alert the user of such anomaly. In the embodiment depicted in FIGS. 1A-1E, an alerting element may be employed to monitor the tension of the string that causes connecting member 56 to couple with mating cavity 64, or to monitor the tension of the string that couples release member 58 to connecting member 56. Similar arrangements may be employed for all the other embodiments of the invention described herein.

More particularly, a reduction in string tension may be used as an indicator of a failure of the locking mechanism of the device, and using techniques similar to those described above with reference to FIG. 27C, this failure may be reported to the patient or to attending personnel to provide for a rapid removal of the device from the stomach.

String tension in the string may be measured in a variety of ways, for example, by tensioning a spring element in line with the string, so that two electrodes will come into contact if the string shortens unexpectedly. This string shortening may generate a local signal, for example, a vibration or an acoustic sound, or may be reported externally, for example via radio-frequency communication.

Such element for detecting string tension may be battery powered, with a power source having a usable life that spans the entire duration of the implant, or may be rechargeable, either through an endoscopically-guided catheter introduced in the stomach of the patient or wirelessly. Such detection element also may be used to ensure that the locking string has been sufficiently deployed by causing the device to provide a feedback that the device has been fully loaded once the lock has come under sufficient tension.

One method of disease treatment of particular interest based on a device according to the present invention is the release of insulin, achieved by disposing an insulin reservoir in the second occluding member (for example, in device 30, in second occluding member 34), which becomes positioned in the gastro-intestinal tract after implantation of the device. Such a release of insulin may be controlled passively, for example, by choosing an orifice of a certain size to control flow from the reservoir into the outer environment, or may be controlled actively, for example, may be timed by a time-controlled actuator as known in the art, or may be actuated by one or more sensors, for example in response to the detection of sugar in the gastro-intestinal tract. In one embodiment, insulin may be released by having the one or more sensors actuate a pump. In another embodiment, release of insulin may be actuated extra-corporeally, by the patient, by a clinician or by an automatic device upon the wireless reception of certain data from a sensor implanted in the body, for example, when sugar level in a portion of the intestine exceeds a certain level. In still another embodiment, a feedback may be provided to the patient or to attending personnel that is related to the conditions causing the release of insulin, and/or to the amount and speed of release of the insulin.

Such ability to release insulin makes a device according to the present invention suitable for the treatment of obesity, diabetes and other diseases not only by providing insulin or other compound in the gastro-intestinal tract, but also through the combination of the occluding action of the proximal member and the release of the compound stored in the device.

More particularly, diabetes may be treated not only through the dispersion of insulin in the gastro-intestinal tract (a direct therapy), but through the combination of insulin dispersion and the slowed gastric emptying causes by the present device, which reduces the requirement for insulin supply (an indirect therapy). Diabetes may also be treated by providing insulin at the required intervals to patients that are either averse to other delivery methods (for example, that are averse to injections) or that are non-compliant due to inability or lack of desire to maintain the required schedules.

Conversely, obesity may be treated by use of the present device not only by reducing food entry into the intestinal tract by the intermittent occluding action on the pyloric valve and by reducing appetite due to the feeling of satiety induced by having the present device reside in the stomach, but also by dispersing insulin in the patient's gastro-intestinal tract, especially in the more morbid cases of obesity.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A method of slowing gastric emptying comprising:
   per-orally introducing a device into a patient's stomach with a first occluding member of the device having an elongated configuration with a plurality of turns and a second occluding member connected to the first occluding member with a tether;
   forming the first occluding member from the elongated configuration into a contracted configuration which is wider than the elongated configuration by nesting the plurality of turns one adjacent to the other and forming a compact shape; and
   locking the first occluding member into the contracted configuration, wherein movements of the stomach causes the first occluding member in the contracted configuration to intermittently obstruct a gastric opening.

2. The method of claim 1, wherein the method further comprises treating a disease including obesity, hyperphagia, dyslipidemia, Prader Willi syndrome, Froelich's syndrome, Cohen syndrome, Summit syndrome, Alstrom syndrome, Borjesen syndrome, Bardet-Biedl syndrome, or hyperlipoproteinemia, types I, II, III, and IV.

3. The method of claim 1, wherein forming the first occluding member comprises forming the contracted configuration within a membrane at least partially surrounding the first occluding member.

4. The method of claim 1, wherein per-orally introducing comprises advancing the device through an esophagus and into the patient's stomach.

5. The method of claim 1, further comprising the step of dispersing a compound from the device into the patient's gastro-intestinal tract.

6. The method of claim 5, wherein dispersing the compound comprises dispersing the compound from a reservoir contained in the device.

7. The method of claim 5, wherein dispersing the compound comprises dispersing the compound from a reservoir contained in the second occluding member.

8. The method of claim 5, wherein the compound is disposed on an outer surface of the device.

9. The method of claim 5, wherein the compound is insulin.

10. The method of claim 1, further comprising unlocking the first occluding member such that the first occluding member reconfigures into the elongated configuration.

11. The method of claim 1, wherein locking further comprises locking a string member in communication with the first occluding member.

12. The method of claim 1, further comprising confirming the contracted configuration of the first occluding member by visual confirmation.

13. The method of claim 1, further comprising confirming the contracted configuration of the first occluding member by a sensor configured to detect the contracted configuration via a modality selected from the group consisting of acoustic, ultrasonic, electrical, electromagnetic, optical, chemical, and tension mechanisms.

14. A method of treating diabetes, comprising:
   per-orally introducing a device into a patient's stomach with a first occluding member of the device having an elongated configuration with a plurality of turns and a second occluding member connected to the first occluding member with a tether;
   forming the first occluding member from the elongated configuration into a contracted configuration which is wider than the elongated configuration by nesting the plurality of turns one adjacent to the other and forming a compact shape;
   locking the first occluding member into the contracted configuration, wherein movements of the stomach causes the first occluding member in the contracted configuration to intermittently obstruct a gastric opening; and
   dispersing insulin from the device into the patient's gastro-intestinal tract.

15. The method of claim 14, further comprising managing glucose peaks by configuring the first occluding member to slow gastric emptying to predetermined ratios.

16. The method of claim 14, wherein dispersing the insulin comprises dispersing the insulin from a reservoir included in the device.

17. The method of claim 14, wherein dispersing the insulin comprises dispersing the insulin from a reservoir included in the second occluding member.

18. The method of claim 14, wherein dispersing the insulin from the device comprises eluting the insulin from a surface of the device.

19. The method of claim 14, wherein dispersing the insulin comprises dispersing the insulin passively.

20. The method of claim 14, wherein dispersing the insulin comprises dispersing the insulin by actuating an insulin dispersing system.

21. The method of claim 20, wherein the insulin dispersing system is a pump.

22. The method of claim 20, wherein the insulin dispersing system is actuated in response to detection by the device of a predetermined condition.

23. The method of claim 22, wherein the predetermined condition comprises one or more of a carbohydrate level, a fat level, and a sugar level.

24. The method of claim 22, further comprising providing a feedback signal to the patient or to a clinician.

25. The method of claim 24, wherein the feedback signal provides a feedback on one or more of the predetermined condition and of an amount of dispersed insulin.

* * * * *